United States Patent
Liu et al.

(10) Patent No.: US 12,398,390 B2
(45) Date of Patent: *Aug. 26, 2025

(54) NEGATIVE SELECTION AND STRINGENCY MODULATION IN CONTINUOUS EVOLUTION SYSTEMS

(71) Applicant: President and Fellows of Harvard College, Cambridge, MA (US)

(72) Inventors: David R. Liu, Lexington, MA (US); Jacob Charles Carlson, Somerville, MA (US); Ahmed Hussein Badran, Somerville, MA (US); Kevin Michael Esvelt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1973 days.

This patent is subject to a terminal disclaimer.

(21) Appl. No.: 16/238,386

(22) Filed: Jan. 2, 2019

(65) Prior Publication Data

US 2019/0256842 A1 Aug. 22, 2019

Related U.S. Application Data

(63) Continuation of application No. 15/112,759, filed as application No. PCT/US2015/012022 on Jan. 20, 2015, now Pat. No. 10,179,911.

(60) Provisional application No. 61/929,378, filed on Jan. 20, 2014.

(51) Int. Cl.
| | |
|---|---|
| *C12N 15/10* | (2006.01) |
| *C12N 7/00* | (2006.01) |
| *C12N 15/01* | (2006.01) |
| *C12N 15/64* | (2006.01) |
| *C12N 15/70* | (2006.01) |
| *C40B 10/00* | (2006.01) |
| *C40B 50/06* | (2006.01) |

(52) U.S. Cl.
CPC ........... *C12N 15/1058* (2013.01); *C12N 7/00* (2013.01); *C12N 15/01* (2013.01); *C12N 15/1024* (2013.01); *C12N 15/1037* (2013.01); *C12N 15/1086* (2013.01); *C40B 10/00* (2013.01); *C40B 50/06* (2013.01); *C07K 2319/735* (2013.01); *C07K 2319/80* (2013.01); *C07K 2319/81* (2013.01); *C12N 15/64* (2013.01); *C12N 15/70* (2013.01); *C12N 2795/00041* (2013.01); *C12N 2795/14121* (2013.01); *C12N 2795/14152* (2013.01); *C12N 2800/101* (2013.01); *C12N 2800/40* (2013.01); *C12N 2830/002* (2013.01); *C12N 2830/60* (2013.01)

(58) Field of Classification Search
None
See application file for complete search history.

(56) References Cited

U.S. PATENT DOCUMENTS

| | | |
|---|---|---|
| 5,057,432 A | 10/1991 | Wangersky et al. |
| 5,223,409 A | 6/1993 | Ladner et al. |
| 5,658,727 A | 8/1997 | Barbas et al. |
| 5,712,089 A | 1/1998 | Borrebaeck et al. |
| 5,821,047 A | 10/1998 | Garrard et al. |
| 5,965,124 A | 10/1999 | Feinberg et al. |
| 6,156,509 A | 12/2000 | Schellenberger |
| 6,429,298 B1 | 8/2002 | Ellington et al. |
| 6,815,194 B2 | 11/2004 | Honjo et al. |
| 6,884,870 B2 | 4/2005 | Bruce et al. |
| 6,969,731 B1 | 11/2005 | Tang et al. |
| 9,023,594 B2 | 5/2015 | Liu et al. |
| 9,228,207 B2 | 1/2016 | Liu et al. |
| 9,267,127 B2 | 2/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,394,537 B2 | 7/2016 | Liu et al. |
| 9,526,784 B2 | 12/2016 | Liu et al. |
| 9,567,589 B2 | 2/2017 | Jin et al. |
| 9,737,604 B2 | 8/2017 | Jin et al. |
| 9,766,216 B2 | 9/2017 | Wada et al. |
| 9,771,574 B2 | 9/2017 | Liu et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |

(Continued)

FOREIGN PATENT DOCUMENTS

| | | |
|---|---|---|
| EP | 3115457 A1 | 1/2017 |
| JP | H0937764 A | 2/1997 |

(Continued)

OTHER PUBLICATIONS

Chibani-Chennoufi S et al. J Bacteriol. Jun. 2004; 186(12):3677-86 (Year: 2004).*
Hendel SJ et al. Nat Methods. Apr. 2021;18(4):346-357 (Year: 2021).*
Mayrhofer JE et al. Proc Natl Acad Sci U S A. Dec. 8, 2020;117(49):31105-31113 (Year: 2020).*

(Continued)

*Primary Examiner* — Kimberly Chong
*Assistant Examiner* — Douglas Charles Ryan
(74) *Attorney, Agent, or Firm* — Wolf, Greenfield & Sacks, P.C.

(57) ABSTRACT

Strategies, systems, methods, reagents, and kits for phage-assisted continuous evolution are provided herein. These include strategies, systems, methods, reagents, and kits allowing for stringency modulation to evolve weakly active or inactive biomolecule variants, negative selection of undesired properties, and/or positive selection of desired properties.

20 Claims, 15 Drawing Sheets

Specification includes a Sequence Listing.

(56) References Cited

U.S. PATENT DOCUMENTS

| | | |
|---|---|---|
| 10,612,011 B2 | 4/2020 | Liu et al. |
| 10,682,410 B2 | 6/2020 | Liu et al. |
| 10,920,208 B2 | 2/2021 | Liu et al. |
| 11,046,948 B2 | 6/2021 | Liu et al. |
| 11,078,469 B2 | 8/2021 | Liu et al. |
| 11,104,967 B2 | 8/2021 | Liu et al. |
| 11,214,792 B2 | 1/2022 | Liu et al. |
| 11,299,729 B2 | 4/2022 | Badran et al. |
| 11,447,809 B2 | 9/2022 | Bryson, Jr. et al. |
| 11,524,983 B2 | 12/2022 | Badran et al. |
| 11,624,130 B2 | 4/2023 | Liu et al. |
| 11,760,986 B2 | 9/2023 | Liu et al. |
| 11,905,623 B2 | 2/2024 | Liu et al. |
| 11,913,040 B2 | 2/2024 | Liu et al. |
| 11,913,044 B2 | 2/2024 | Liu et al. |
| 12,060,553 B2 | 8/2024 | Packer et al. |
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0186292 A1 | 10/2003 | MacNeil et al. |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2011/0318385 A1 | 12/2011 | Jackson et al. |
| 2012/0128649 A1 | 5/2012 | Chaddock et al. |
| 2012/0190825 A1 | 7/2012 | Neumann et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Brunt et al. |
| 2015/0275202 A1 | 10/2015 | Liu et al. |
| 2016/0002301 A1 | 1/2016 | Je et al. |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0057545 A9 | 3/2018 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0276816 A1 | 9/2019 | Liu et al. |
| 2019/0276873 A1 | 9/2019 | Dong et al. |
| 2020/0071722 A1 | 3/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2021/0163924 A1 | 6/2021 | Packer et al. |
| 2021/0238569 A1 | 8/2021 | Liu et al. |
| 2021/0261938 A1 | 8/2021 | Liu et al. |
| 2021/0403887 A1 | 12/2021 | Liu et al. |
| 2022/0073887 A1 | 3/2022 | Liu et al. |
| 2022/0154237 A1 | 5/2022 | Liu et al. |
| 2022/0195418 A1 | 6/2022 | Liu et al. |
| 2022/0259269 A1 | 8/2022 | Liu et al. |
| 2022/0267754 A1 | 8/2022 | Liu et al. |
| 2023/0220016 A1 | 7/2023 | Liu et al. |
| 2024/0052331 A1 | 2/2024 | Liu et al. |
| 2024/0124863 A1 | 4/2024 | Liu et al. |
| 2024/0200044 A1 | 6/2024 | Liu et al. |
| 2024/0209338 A1 | 6/2024 | Liu et al. |
| 2024/0271119 A1 | 8/2024 | Liu et al. |

FOREIGN PATENT DOCUMENTS

| | | |
|---|---|---|
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 99/23116 A1 | 5/1999 |
| WO | WO 00/71694 A1 | 11/2000 |
| WO | WO 01/05950 A2 | 1/2001 |
| WO | WO 2001/038547 A2 | 5/2001 |
| WO | WO 01/61049 A1 | 8/2001 |
| WO | WO 2005/081632 A2 | 9/2005 |
| WO | WO 07/066923 A1 | 6/2007 |
| WO | WO 08/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/125015 A2 | 10/2011 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 A1 | 4/2013 |
| WO | WO 2014/039585 A2 | 3/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A2 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2017/136792 A2 | 8/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/056002 A1 | 3/2018 |
| WO | WO 2018/109447 A1 | 6/2018 |
| WO | WO 2018/119042 A1 | 6/2018 |
| WO | WO 2018/136939 A1 | 7/2018 |
| WO | WO 2019/040935 A1 | 2/2019 |
| WO | WO 2019/067815 A2 | 4/2019 |
| WO | WO 2019/089592 A1 | 5/2019 |
| WO | WO 2019/118362 A1 | 6/2019 |
| WO | WO 2020/204836 A1 | 10/2020 |
| WO | WO 2021/080427 A1 | 4/2021 |
| WO | WO 2021/188286 A2 | 9/2021 |
| WO | WO 2022/109421 A1 | 5/2022 |

OTHER PUBLICATIONS

Polyak (Kufe DW, Pollock RE, Weichselbaum RR, et al., editors. Holland-Frei Cancer Medicine. 6th edition. Hamilton (ON): BC Decker; 2003 (Year: 2003).*

Meyer AJ et al. Nat Biotechnol. Jun. 7, 2011;29(6):502-3 (Year: 2011).*

Nakahira Y et al. Plant Cell Physiol. Oct. 2013;54(10):1724-35 (Year: 2013).*

International Preliminary Report on Patentability, mailed Aug. 1, 2019, in connection with Application No. PCT/US2018/14867.

Invitation to Pay Additional Fees, mailed Sep. 12, 2018, in connection with Application No. PCT/US2018/040692.

International Search Report and Written Opinion, mailed Nov. 15, 2018, in connection with Application No. PCT/US2018/040692.

International Preliminary Report on Patentability, mailed Jan. 16, 2020, in connection with Application No. PCT/US2018/040692.

Invitation to Pay Additional Fees, mailed Jan. 4, 2019, in connection with Application No. PCT/US2018/051557.

International Preliminary Report on Patentability, mailed Apr. 2, 2020, in connection with Application No. PCT/US2018/051557.

(56) References Cited

OTHER PUBLICATIONS

International Search Report and Written Opinion, mailed Sep. 4, 2019, in connection with Application No. PCT/US2019/037216.
International Preliminary Report on Patentability, mailed Dec. 24, 2020, in connection with Application No. PCT/US2019/037216.
Partial European Search Report for Application No. 18847527.1, mailed Apr. 21, 2021.
Extended European Search Report for Application No. 18847527.1, mailed Aug. 2, 2021.
Invitation to Pay Additional Fees, mailed Nov. 19, 2018, in connection with Application No. PCT/US18/48134.
International Search Report and Written Opinion, mailed Jan. 22, 2019, in connection with Application No. PCT/US18/48134.
International Preliminary Report on Patentability, mailed Mar. 5, 2020, in connection with Application No. PCT/US18/48134.
Invitation to Pay Additional Fees, mailed Oct. 13, 2020, in connection with Application No. PCT/US2020/042016.
International Search Report and Written Opinion, mailed Dec. 10, 2020, in connection with Application No. PCT/US2020/042016.
International Preliminary Report on Patentability mailed Jan. 27, 2022, in connection with Application No. PCT/US2020/042016.
[No Author Listed] Genbank Submission. NCBI; Accession No. WP_010869888, version WP_010869888.1. tyrosine-tRNA ligase [Methanocaldococcus jannaschii]. Jun. 1, 2019.
[No Author Listed] Ncbi Accession No. XP_015843220.1. C→U editing enzyme APOBEC-1 [Peromyscus maniculatus bairdii], XP002793540. Mar. 21, 2016.
[No Author Listed] Ncbi Accession No. XP_021505673.1. C→U editing enzyme APOBEC-1 [Meriones unguiculatus], XP002793541. Jun. 27, 2017.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Bade et al., Botulinum neurotoxin type D enables cytosolic delivery of enzymatically active cargo proteins to neurones via unfolded translocation intermediates. J Neurochem. Dec. 2004;91(6):1461-72.
Binz et al., Clostridial neurotoxins: mechanism of SNARE cleavage and outlook on potential substrate specificity reengineering. Toxins. Apr. 2010;2(4):665-82. Epub Apr. 13, 2010.
Blum et al., Phage-assisted evolution of botulinum neurotoxin proteases with reprogrammed specificity. Science. Feb. 19, 2021;371(6531):803-810. doi: 10.1126/science.abf5972.
Blum, Continuous evolution of bacterial neurotoxins for intracellular protease therapy. 2019. Poster. 1 page.
Blum, Generation of selective botulinum neurotoxin proteases with reprogrammed substrate specificity through phage-assisted directed evolution. Apr. 7, 2020. Powerpoint. 36 pages.
Blum, Generation of selective botulinum neurotoxin proteases with reprogrammed substrate specificity through phage-assisted directed evolution. Jun. 4, 2019. Powerpoint. 24 pages.
Box et al., A multi-domain protein system based on the HC fragment of tetanus toxin for targeting DNA to neuronal cells. J Drug Target. Jul. 2003;11(6):333-43. doi: 10.1080/10611863100001634667.
Burland et al., Analysis of the Escherichia coli genome VI: DNA sequence of the region from 92.8 through 100 minutes. Nucleic Acids Res. Jun. 25, 1995;23(12):2105-19. doi: 10.1093/nar/23.12.2105.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Cattaneo et al., SEL1L affects human pancreatic cancer cell cycle and invasiveness through modulation of PTEN and genes related to cell-matrix interactions. Neoplasia. 2005;7(11):1030-1038.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chen et al., Engineering botulinum neurotoxin to extend therapeutic intervention. PNAS. Jun. 2009;106(23):9180-4.
Chen et al., Mechanism of substrate recognition by botulinum neurotoxin serotype A. J Biol Chem. Mar. 30, 2007;282(13):9621-9627. doi: 10.1074/jbc.M611211200. Epub Jan. 23, 2007.
Chen et al., Multiple pocket recognition of SNAP25 by botulinum neurotoxin serotype E. J Biol Chem. Aug. 31, 2007;282(35):25540-7. doi: 10.1074/jbc.M701922200. Epub Jul. 3, 2007.
Chen et al., SNARE-mediated membrane fusion. Nat Rev Mol Cell Biol. Feb. 2001;2(2):98-106.
Chen et al., VAMP8 facilitates cellular proliferation and temozolomide resistance in human glioma cells. Neuro-Oncology. 2015;17(3):407-18. Epub Sep. 10, 2014.
Chen, Clinical uses of botulinum neurotoxins: current indications, limitations and future developments. Toxins (Basel). 2012;4(10):913-939.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. 2013; 339: 819-23.
Craik et al., Proteases as therapeutics. Biochem J. Apr. 2011;435(1):16 pages.
Deltcheva et al., CRISPR RNA maturation by trans-encoded small RNA and host factor RNase III. Nature. Mar. 31, 2011;471(7340):602-7. doi: 10.1038/nature09886.
Deribe, Mechanistic insights into the role of truncating PREX2 mutations in melanoma. Mol Cell Oncol. 2016;3(3):e1160174.
Dicarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dong et al., Using fluorescent sensors to detect botulinum neurotoxin activity in vitro and in living cells. Proc Natl Acad Sci U S A. Oct. 12, 2004;101(41):14701-6. doi: 10.1073/pnas.0404107101. Epub Oct. 1, 2004.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Esvelt et al., A system for the continuous directed evolution of biomolecules. Nature. Apr. 28, 2011;472(7344):499-503. doi: 10.1038/nature09929. Epub Apr. 10, 2011.
Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., Exo1: A new chemical inhibitor of the exocytic pathway. PNAS. May 2003;100(11):6469-74.
Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fu et al., Promises and Pitfalls of Intracellular Delivery of Proteins. Bioconjugate Chemistry. Aug. 2014;25:1602-8.
Genbank Submission. NCBI; Accession No. WP_011033391, version WP_011033391.1. pyrrolysine-tRNA(Pyl) ligase [Methanosarcina mazei]. Polycarpo et al.; Nov. 29, 2019.

(56) References Cited

OTHER PUBLICATIONS

Genbank Submission. NCBI; Accession No. WP_011305865, version WP_011305865.1. pyrrolysine-tRNA(Pyl) ligase [Methanosarcina barkeri]. Polycarpo et al.; Nov. 29, 2019.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.
Guzman et al., Tight regulation, modulation, and high-level expression by vectors containing the arabinose PBAD promoter. J Bacteriol. 1995;177(14):4121-4130.
Harris et al., Measurement of enzyme activity. Methods Enzymol. 2009;463:57-71.
Hedstrom et al., Converting trypsin to chymotrypsin: the role of surface loops. Science. Mar. 1992;255(5049):1249-53.
Hendricks et al., The S. cerevisiae Mag1 3-methyladenine DNA glycosylase modulates susceptibility to homologous recombination. DNA Repair (Amst). 2002;1(8):645-659.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jankovic et al., Direct selection and phage display of a Gram-positive secretome. Genome Biology. Dec. 13, 2007; 8(266):1-15.
Jiang et al., Py1Sn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jones et al., Phage-Assisted Continuous Evolution and Selection of Enzymes for Chemical Synthesis. ACS Cent Sci. Sep. 22, 2021;7(9):1581-1590. doi: 10.1021/acscentsci.1c00811. Epub Sep. 13, 2021.
Kasai et al., Distinct initial SNARE configurations underlying the diversity of exocytosis. Physiol Rev. Oct. 2012;92(4):1915-64. doi: 10.1152/physrev.00007.2012.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.
Kim et al., DJ-1, a novel regulator of the tumor suppressor PTEN. Cancer Cell. 2005;7(3):263-273.
Kim et al., Increasing the genome-targeting scope and precision of base editing with engineered Cas9-cytidine deaminase fusions. Nature Biotechnology; Feb. 13, 2007; 35(4): 371-376.
Köhler, A yeast-based growth assay for the analysis of site-specific proteases. Nucleic Acids Res. 2003;31(4):e16. 5 pages.
Laskowska et al., IbpA and IbpB, the new heat-shock proteins, bind to endogenous *Escherichia coli* proteins aggregated intracellularly by heat shock. Biochimie. 1996;78(2):117- 22.
Lebeda et al., The Zinc-Dependent Protease Activity of the Botulinum Neurotoxins. Toxins. May 2010;2:978-97.
Lee et al., Enhanced production of human full-length immunoglobulin G1 in the periplasm of *Escherichia coli*. Appl Microbiol Biotechnol. Feb. 2014;98(3):1237-46. doi: 10.1007/s00253- 01-5390-z. Epub Nov. 26, 2013.
Liu et al., Adding new chemistries to the genetic code. Annu Rev Biochem. 2010;79:413-44. doi: 10.1146/annurev.biochem.052308.105824.
Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.
Lu, The destructive effect of botulinum neurotoxins on the SNARE protein: SNAP-25 and synaptic membrane fusion. PeerJ. 2015;3:e1065. Published Jun. 30, 2015.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.
Mali et al., RNA-guided human genome engineering via Cas9. Science. 2013; 339:823-26.
Manta et al., Disulfide Bond Formation in the Periplasm of *Escherichia coli*. EcoSal Plus. Feb. 2019;8(2). doi: 10.1128/ecosalplus.ESP-0012-2018.
Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.
Masuyer et al., Engineered botulinum neurotoxins as new therapeutics. Annu Rev Pharmacol Toxicol. 2014;54:27-51.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.
Mihai et al., PTEN inhibition improves wound healing in lung epithelia through changes in cellular mechanics that enhance migration. Am J Physiol Lung Cell Mol Physiol. 2012;302(3):L287-L299.
Miller et al., A TALE nuclease architecture for efficient genome editing. Nat Biotechnol. Feb. 2011;29(2):143-8. doi:10.1038/nbt.1755. Epub Dec. 22, 2010.
Morrison et al., Disulfide-compatible phage-assisted continuous evolution in the periplasmic space. Nat Commun. Oct. 13, 2021;12(1):5959. doi: 10.1038/s41467-021-26279-8.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Ngo et al., Computational Complexity, Protein Structure Prediction, and the Levinthal Paradox in the Protein Folding Problem and Tertiary Structure Prediction. Merz et al., Eds. 1994. pp. 433 and 492-495.
Nicholson-Fish et al., VAMP4 Is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.
Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

(56) References Cited

OTHER PUBLICATIONS

O'Donoghue et al., Upgrading protein synthesis for synthetic biology. Nat Chem Biol. Oct. 2013;9(10):594-8. doi: 10.1038/nchembio. 1339.
Oeemig et al., Solution structure of DnaE intein from Nostoc punctiforme: structural basis for the design of a new split intein suitable for site-specific chemical modification. FEBS Lett. May 6, 2009;583(9):1451-6.
Pickett et al., Towards New Uses of Botulinum Toxin as a Novel Therapeutic Tool. Toxins. Jan. 2011;3:63-81.
Pogson et al., Engineering Next Generation Proteases. Curr Opin Biotechnol. Aug. 2009;20(4):390-7.
Popa et al., Phage-Assisted Continuous Evolution (PACE): A Guide Focused on Evolving Protein-DNA Interactions. ACS Omega. Oct. 16, 2020;5(42):26957-26966. doi: 10.1021/acsomega.0c03508. eCollection Oct. 27, 2020.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Raingo et al., VAMP4 directs synaptic vesicles to a pool that selectively maintains asynchronous neurotransmission. Nat Neurosci. Mar. 1, 20121;15(5):738-45. doi: 10.1038/nn.3067.
Rawlings et al., MEROPS: the database of proteolytic enzymes, their substrates and inhibitors. Nucleic Acids Res. Jan. 2014;42(Database issue):D503-9.
Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.
Ruiz-Martinez et al., YKT6 expression, exosome release, and survival in non-small cell lung cancer. Oncotarget. Aug. 9, 2016;7(32):51515-51524. doi: 10.18632/oncotarget.9862.
Sikorra et al., Identification and Characterization of Botulinum Neurotoxin A Substrate Binding Pockets and Their Re-Engineering for Human SNAP-23. J Mol Biol. Jan. 29, 2016;428(2 Pt A):372-384. doi: 10.1016/j.jmb.2015.10.024. Epub Oct. 30, 2015.
Sikorra et al., Identification of the amino acid residues rendering TI-VAMP insensitive toward botulinum neurotoxin B. J Mol Biol. Mar. 24, 2006;357(2):574-82. doi: 10.1016/j.jmb.2005.12.075. Epub Jan. 18, 2006.
Sikorra et al., Substrate Recognition Mechanism of VAMP/Synaptobrevin-cleaving Clostridial Neurotoxins. Journal of Biological Chemistry. 2008;283:21145-52. Epub May 29, 2008.
Somm et al., A botulinum toxin-drived targeted secretion inihibitor downregulates the GH/IGF1 axis. The Journal of Clinical Investigation. Sep. 2012;122(9):3295-306.
Steffen et al., MT1-MMP-Dependent Invasion Is Regulated by TI-VAMP/VAMP7. Current Biology. Jun. 2008;18:926-31.
Tsai et al., Targeting botulinum neurotoxin persistence by the ubiquitin-proteasome system. PNAS. Sep. 2010;107(38):16554-9.
Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.
Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.
Varadarajan et al., Engineering of protease variants exhibiting high catalytic activity and exquisite substrate selectivity. PNAS. May 2005;102(19):6855-60.
Varadarajan et al., Highly active and selective endopeptidases with programmed substrate specificities. Nat Chem Biol. May 2008;4(5):290-4.
Vincenzeti et al., Functional properties of subunit interactions in human cytidine deaminase. Protein Engi. Dec. 2003;16(12):1055-61. doi: 10.1093/protein/gzg117.
Vincenzeti et al., Possible role of two phenylalanine residues in the active site of human cytidine deaminase. Protein Eng. Nov. 2000;13(11):791-9. doi: 10.1093/protein/13.11.791.
Wang et al., Continuous directed evolutions of proteins with improved soluble expression. Nature Chemical Biology. Nat Publishing Group. Aug. 20, 2018; 14(10):972-980.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.
Yamamoto et al., Virological and immunological bases for HIV-1 vaccine design. Uirusu 2007;57(2):133-139. https://doi.org/10.2222/jsv.57.133.
Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.
Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.
Yeh et al., Retargeted Clostridial neurotoxins as Novel Agents for Treating Chronic Diseases. Biochemistry. Nov. 2011;50:10419-21.
Yi et al., Engineering of TEV protease variants by yeast ER sequestration screening (YESS) of combinatorial libraries. PNAS. Apr. 2013;110(18):7229-34.
Zhang et al., Identification and characterization of a novel botulinum neurotoxin. Nat Commun. Aug. 3, 2017;8:14130. doi: 10.1038/ncomms14130.
Ziemann et al., Gene name errors are widespread in the scientific literature. Genome Biol. Aug. 23, 2016;17(1):177. doi: 10.1186/s13059-016-1044-7.
Extended European Search Report for EP 09812363, mailed Mar. 30, 2012.
Extended European Search Report for EP 16 20 3684, mailed May 26, 2017.
International Search Report and Written Opinion for PCT/US2009/056194 mailed Jun. 21, 2010.
International Preliminary Report on Patentability for PCT/US2009/056194 mailed Mar. 17, 2011.
Extended European Search Report for EP 17 16 0955, mailed May 16, 2017.
Invitation to Pay Additional Fees for PCT/US2011/066747, mailed Aug. 30, 2012.
International Search Report and Written Opinion for PCT/US2011/066747, mailed Oct. 30, 2012.
International Preliminary Report on Patentability for PCT/US2011/066747, mailed Jul. 4, 2013.
International Search Report and Written Opinion for PCT/US2015/012022, mailed Sep. 25, 2015.
International Preliminary Report on Patentability for PCT/US2015/012022, mailed Aug. 4, 2016.
Invitation to Pay Additional Fees for PCT/US/2016/043559, mailed Jan. 12, 2017.
International Search Report and Written Opinion for PCT/US/2016/043559, mailed Mar. 10, 2017.
International Search Report and Written Opinion for PCT/US2015/057012, mailed Jun. 10, 2016.
International Preliminary Report on Patentability for PCT/US2015/057012, mailed May 4, 2017.
International Search Report and Written Opinion for PCT/US2016/027795, mailed Aug. 11, 2016.
International Preliminary Report on Patentability for PCT/US2016/027795, mailed Oct. 26, 2017.
Invitation to Pay Additional Fees for PCT/US2016/044546, mailed Oct. 12, 2016.

(56) References Cited

OTHER PUBLICATIONS

International Search Report and Written Opinion for PCT/US2016/044546, mailed Dec. 28, 2016.
International Search Report and Written Opinion for PCT/US2016/043513, mailed Nov. 30, 2016.
International Preliminary Report on Patentability for PCT/US/2016/043559, mailed Feb. 1, 2018.
International Preliminary Report on Patentability for PCT/US/2016/044546, mailed Feb. 8, 2018.
International Preliminary Report on Patentability for PCT/US2016/043513, mailed Feb. 1, 2018.
Invitation to Pay Additional Fees for PCT/US2018/14867, mailed Apr. 5, 2018.
International Search Report and Written Opinion for PCT/US2018/14867, mailed May 23, 2018.
International Search Report and Written Opinion for PCT/US2018/044242, mailed Nov. 21, 2018.
International Search Report and Written Opinion for PCT/US2018/051557, mailed Feb. 25, 2019.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. 2014;1-10.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase- promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 1, 19915;352(6336):624-8.
Click et al., Filamentous phage infection: required interactions with the TolA protein. J Bacteriol. Oct. 1997; 179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in Escherichia coli K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 2, 19995;274(26):18218-30.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci USA. Aug. 15, 1991;88(16):7160-4.

(56) References Cited

OTHER PUBLICATIONS

Durai et al., A bacterial one-hybrid selection system for interrogating zinc finger-DNA interactions. Comb Chem High Throughput Screen. May 2006;9(4):301-11.
Durniak et al., The structure of a transcribing T7 Rna polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993; 12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and Escherichia coli expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., Escherichia coli one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015; 12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat-a continuous culture system of a bacteriophage for the study of the mutation rate and the selection process of the DNA level. Rev Sci Instrum. Apr. 1982;53(4):517-22.

Husimi, Selection and evolution of bacteriophages in cellstat. Adv Biophys. 1989;25:1-43.
Ichetovkin et al., Substrate recognition by the leucyl/phenylalanyl-tRNA-protein transferase. Conservation within the enzyme family and localization to the trypsin-resistant domain. J Biol Chem. Dec. 26, 19976;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Komor et al., Programmable editing of a target base in genomic DNA without double-stranded DNA cleavage. Nature. May 19, 2016;533(7603):420-4. doi: 10.1038/nature17946. Epub Apr. 20, 2016.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Latimer et al., Specificity of monoclonal antibodies produced against phosphorothioate and ribo modified DNAs. Mol Immunol. Oct. 1995;32(14-15):1057-64.
Leconte et al., A population-based experimental model for protein evolution: effects of mutation rate and selection stringency on evolutionary outcomes. Biochemistry. Feb. 26, 2013; 52(8): 1490-1499.
Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.
Lincoln et al., Self-sustained replication of an RNA enzyme. Science. Feb. 2, 20097;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Lutz et al., Creating multiple-crossover DNA libraries independent of sequence identity. Proc Natl Acad Sci U S A. Sep. 25, 2001;98(20):11248-53. Epub Sep. 18, 2001.

(56) References Cited

OTHER PUBLICATIONS

Maeder et al., Robust, synergistic regulation of human gene expression using TALE activators. Nat Methods. Mar. 2013;10(3):243-5. doi: 10.1038/nmeth.2366. Epub Feb. 10, 2013.

Makeyev et al., Evolutionary potential of an RNA virus. J Virol. Feb. 2004;78(4):2114-20.

Malmborg et al., Selective phage infection mediated by epitope expression on F pilus. J Mol Biol. Oct. 31, 1997;273(3):544-51.

Martin et al., Kinetic analysis of T7 RNA polymerase-promoter interactions with small synthetic promoters. Biochemistry. May 19, 1987;26(10):2690-6.

McCafferty et al., Phage antibodies: filamentous phage displaying antibody variable domains. Nature. Dec. 6, 1990;348(6301):552-4.

McConnell et al., Constrained peptide libraries as a tool for finding mimotopes. Gene. Dec. 30, 1994;151(1-2):115-8.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Nelson et al., Filamentous phage DNA cloning vectors: a noninfective mutant with a nonpolar deletion in gene III. Virology. Jan. 30, 1981;108(2):338-50.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

O'Maille et al., Structure-based combinatorial protein engineering (Scope). J Mol Biol. Aug. 23, 2002;321(4):677-91.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier e al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Rakonjac et al., Filamentous phage are released from the bacterial membrane by a two-step mechanism involving a short C-terminal fragment of pIII. J Mol Biol. Jun. 25, 1999;289(5):1253-65.

Rakonjac et al., Filamentous phage infection-mediated gene expression: construction and propagation of the gIII deletion mutant helper phage R408d3. Gene. Oct. 1, 1997;198(1-2):99-103.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the Escherichia coli DNA polymerase V requires assembly of a RecA nucleoprotein filament. J Biol Chem. Feb. 23, 2001;276(8):5511-7. Epub Nov. 17, 2000.

Riechmann et al., The C-terminal domain of TolA is the coreceptor for filamentous phage infection of *E. coli*. Cell. Jul. 25, 1997;90(2):351-60.

Ringquist et al., Translation initiation in *Escherichia coli:* equences within the ribosome-binding site. Mol Microbiol. May 1992;6(9):1219-29.

Rosenberg et al., T7 Select® Phage Display System: A Powerful new protein display system based on bacteriophage T7. Innovations. 1996;6:1-6.

Santini et al., Efficient display of an HCV cDNA expression library as C-terminal fusion to the capsid protein D of bacteriophage lambda. J Mol Biol. Sep. 11, 1998;282(1):125-35.

Santoro et al., Directed evolution of the site specificity of Cre recombinase. Proc Natl Acad Sci U S A. Apr. 2, 2002;99(7):4185-90. Epub Mar. 19, 2002.

Schultz et al., Oligo-2'-fluoro-2'-deoxynucleotide N3'→P5' phosphoramidates: synthesis and properties. Nucleic Acids Res. Aug. 1, 1996;24(15):2966-73.

Scott et al., Searching for peptide ligands with an epitope library. Science. Jul. 27, 1990;249(4967):386-90.

Sices et al., A genetic screen for the isolation and characterization of site-specific proteases. Proc Natl Acad Sci U S A. Mar. 17, 1998;95(6):2828-33.

Sices et al., Rapid genetic selection of inhibitor-resistant protease mutants: clinically relevant and novel mutants of the HIV protease. AIDS Res Hum Retroviruses. Sep. 1, 2001;17(13):1249-55.

Sieber et al., Libraries of hybrid proteins from distantly related sequences. Nat Biotechnol. May 2001;19(5):456-60.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Smith, Filamentous fusion phage: novel expression vectors that display cloned antigens on the virion surface. Science. Jun. 14, 1985;228(4705):1315-7.

Stemmer, Rapid evolution of a protein in vitro by DNA shuffling. Nature. Aug. 4, 1994;370(6488):389-91.

Sutter et al., Non-replicating vaccinia vector efficiently expresses bacteriophage T7 RNA polymerase. FEBS Lett. Aug. 28, 1995;371(1):9-12.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tsuji et al., Random multi-recombinant PCR for the construction of combinatorial protein libraries. Nucleic Acids Res. Oct. 15, 2001;29(20):E97.

Tzagoloff et al., The Initial Steps In Infection With Coliphage M13. Virology. Nov. 1964;24:372-80.

Vidal et al., Yeast forward and reverse 'n'-hybrid systems. Nucleic Acids Res. Feb. 15, 1999;27(4):919-29.

Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.

Voigt et al., Rational evolutionary design: the theory of in vitro protein evolution. Adv Protein Chem. 2000;55:79-160.

Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.

Wang et al., Evolution of new nonantibody proteins via iterative somatic hypermutation. Proc Natl Acad Sci U S A. Nov. 30, 2004;101(48):16745-9. Epub Nov. 19, 2004.

Wang et al., Programming cells by multiplex genome engineering and accelerated evolution. Nature. Aug. 13, 2009;460(7257):894-8. Epub Jul. 26, 2009.

Wharton et al., A new-specificity mutant of 434 repressor that defines an amino acid-base pair contact. Nature. Apr. 30-May 6, 1987;326(6116):888-91.

(56) References Cited

OTHER PUBLICATIONS

Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
Chappell et al., Generation and characterization of proteolytically active and highly stable truncated and full-length recombinant West Nile virus NS3. Protein Expr Purif. May 2007;53(1):87-96. doi: 10.1016/j.pep.2006.10.022. Epub Nov. 7, 2006.
Jan et al., Reversible ON- and OFF-switch chimeric antigen receptors controlled by lenalidomide. Sci Transl Med. Jan. 6, 2021;13(575):eabb6295. doi: 10.1126/scitranslmed.abb6295.
Jan et al., Reversible ON- and OFF-switch chimeric antigen receptors controlled by lenalidomide. Sci Transl Med. 2021. Supplemental info. 12 pages.
Miller et al., Phage-assisted continuous and non-continuous evolution. Nat Protoc. Dec. 2020;15(12):4101-4127. doi: 10.1038/s41596-020-00410-3. Epub Nov. 16, 2020.
Morrison et al., Chapter 4: Future directions and potential applications of this work. Thesis for Harvard University. 2021. 29 pages.
Morrison et al., Disulfide-compatible phage-assisted continuous evolution in the periplasmic space. Author Manuscript with Supplementary information. Broad Institute of Harvard and MIT and Harvard University. 2022. 75 pages.
Xie et al., Contingency and chance erase necessity in the experimental evolution of ancestral proteins. Elife. Jun. 1, 2021;10:e67336. doi: 10.7554/eLife.67336.
U.S. Appl. No. 16/410,767, filed May 13, 2019, Liu et al.
U.S. Appl. No. 17/541,848, filed Dec. 3, 2021, Liu et al.
U.S. Appl. No. 18/050,014, filed Oct. 26, 2022, Liu et al.
U.S. Appl. No. 17/123,632, filed Dec. 16, 2020, Liu et al.
U.S. Appl. No. 18/365,105, filed Aug. 3, 2023, Liu et al.
U.S. Appl. No. 17/581,235, filed Jan. 21, 2022, Badran et al.
U.S. Appl. No. 16/804,228, filed Feb. 28, 2020, Liu et al.
U.S. Appl. No. 17/355,735, filed Jun. 23, 2021, Liu et al.
U.S. Appl. No. 16/521,371, filed Jul. 24, 2019, Liu et al.
U.S. Appl. No. 17/398,870, filed Aug. 10, 2021, Liu et al.
U.S. Appl. No. 16/628,456, filed Jan. 3, 2020, Liu et al.
U.S. Appl. No. 16/648,162, filed Mar. 17, 2020, Liu et al.
U.S. Appl. No. 18/178,780, filed Mar. 6, 2023, Liu et al.
U.S. Appl. No. 17/251,276, filed Dec. 11, 2020, Liu et al.
U.S. Appl. No. 16/641,630, filed Feb. 24, 2020, Liu et al.
U.S. Appl. No. 17/627,035, filed Jan. 13, 2022, Liu et al.
PCT/US2018/14867, Aug. 1, 2019, International Preliminary Report on Patentability.
PCT/US2018/040692, Sep. 12, 2018, Invitation to Pay Additional Fees.
PCT/US2018/040692, Nov. 15, 2018, International Search Report and Written Opinion.
PCT/US2018/040692, Jan. 16, 2020, International Preliminary Report on Patentability.
PCT/US2018/051557, Jan. 4, 2019, Invitation to Pay Additional Fees.
PCT/US2018/051557, Apr. 2, 2020, International Preliminary Report on Patentability.
PCT/US2019/037216, Sep. 4, 2019, International Search Report and Written Opinion.
PCT/US2019/037216, Dec. 24, 2020, International Preliminary Report on Patentability.
EP18847527.1, Apr. 21, 2021, Partial European Search Report.
EP18847527.1, Aug. 2, 2021, Extended European Search Report.
PCT/US18/481134, Nov. 19, 2018, Invitation to Pay Additional Fees.
PCT/US18/481134, Jan. 22, 2019, International Search Report and Written Opinion.
PCT/US18/481134, Mar. 5, 2020, International Preliminary Report on Patentability.
PCT/US2020/042016, Oct. 13, 2020, Invitation to Pay Additional Fees.
PCT/US2020/042016, Dec. 10, 2020, International Search Report and Written Opinion.
PCT/US2020/042016, Jan. 27, 2022, International Preliminary Report on Patentability.

\* cited by examiner

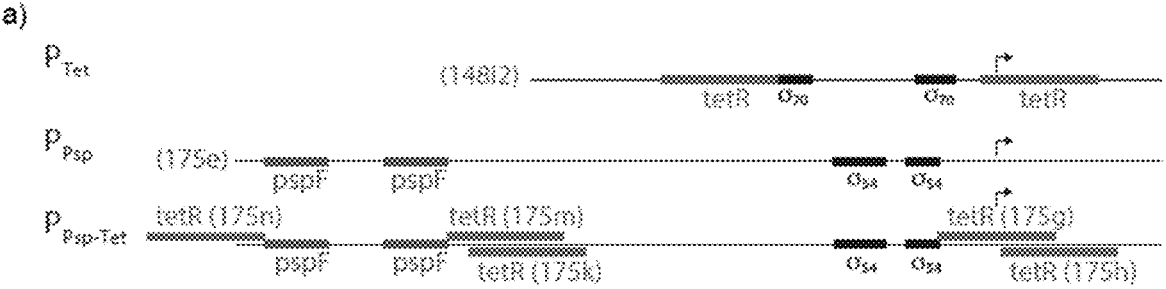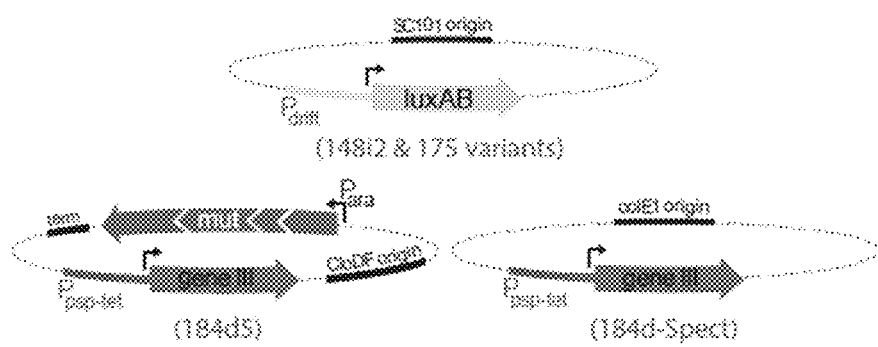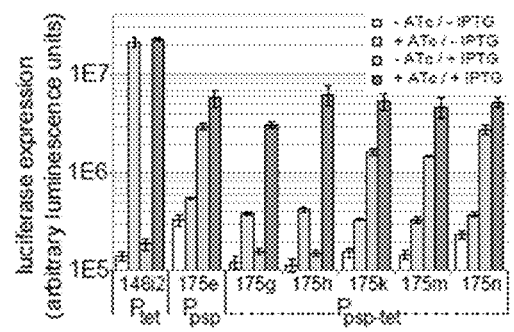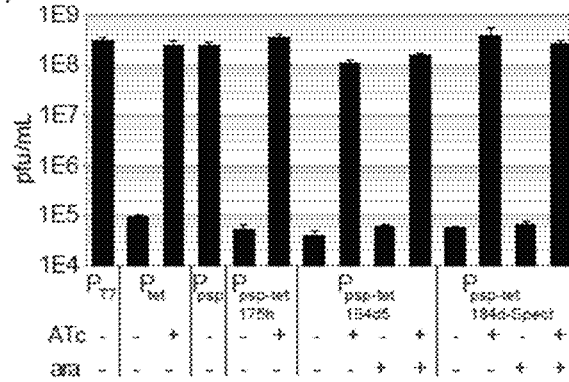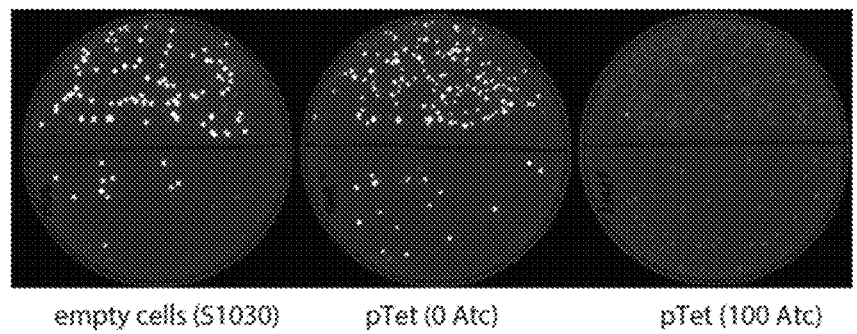
FIGURE 2

```
wt pIII     MKKLLFAIPLVVPFYSHSAETVESCLAKPHTENSFTNVWKDDKTLDRYANYEGCLWNATG  60
N-C83       MKKLLFAIPLVVPFYSHSAETVESCLAKPHTENSFTNVWKDDKTLDRYANYEGCLWNATG  60
N*-C83      MKKLLFAIPLVVPFYSHSAETVESCLAKPHTENSFTNVWKDDKTLDRYANYEGCLWNATG  60
N2-C83      MKKLLFAIPLVVPFYSHSAETVG-------------------------------------  23
C-domain    MKKLLFAIPLVVPFYSHSAETVD-------------------------------------  23
C83         MKKLLFAIPLVVPFYSHSAETVS-------------------------------------  23
            ********************** wt pIII     VVVCTGDETQCYGTWVPIGLAIPENEGGGSEGGGSEGGGSEGGGTKPPEYGDTPIPGYTY  120
N-C83       VVVCTGDETQCYGTWVPIGLAIPENEGGGSEGGGSEGGGSEGGGTKPPEYGDTPIPGYTY  120
N*-C83      VVVCTGDETQCW---VPIGLAIPENEGGGSEGGGSEGGGSEGGGTKPPEYGDTPIPGYTY  117
N2-C83      ----------------------------------GGSEGGGTKPPEYGDTPIPGYTY    46
C-domain    ------------------------------------------------------------
C83         ------------------------------------------------------------ wt pIII     INPLDGTYPPGTEQNPANPNPSLEESQPLNTFMFQNNRFRNRQGALTVYTGTVTQGTDPV  180
N-C83       INPLDGTYPPGTEQNPANPNPSLEESQPLNTFMFQNNRFRNRQGALTVYTGTVTQGTDPV  180
N*-C83      INPLDGTYPPGTEQNPANPNPSLEESQPLNTFMFQNNRFRNRQGALTVYTGTVTQGTDPV  177
N2-C83      INPLDGTYPPGTEQNPANPNPSLEESQPLNTFMFQNNRFRNRQGALTVYTGTVTQGTDPV  106
C-domain    ------------------------------------------------------------
C83         ------------------------------------------------------------ wt pIII     KTYYQYTPVSSKAMYDAYWNGKFRDCAFHSGFNEDPFVCEYQGQSSDLPQPPVNAGGGSG  240
N-C83       KTYYQYTPVSSKAMYDAYWNGKFRDCAFHSGFNEDPFVCEYQGQSSDLPQPPVNAGGGSG  240
N*-C83      KTYYQYTPVSSKAMYDAYWNGKFRDCAFHSGFNEDPFVCEYQGQSSDLPQPPVNAGGGSG  237
N2-C83      KTYYQYTPVSSKAMYDAYWNGKFRDCAFHSGFNEDPFVCEYQGQSSDLPQPPVNAGGGSG  166
C-domain    ------------------------------------------------------------
C83         ------------------------------------------------------------ wt pIII     GGSGGGSEGGGSEGGGSEGGGSEGGGSEGGGSGSGDFDYEKMANANKGAMTENADENALQS  300
N-C83       GGSGGGSEGGGSEGGGSEGGGSEGGGSGGGS-----------------------------  271
N*-C83      GGSGGGSEGGGSEGGGSEGGGSEGGGSGGGS-----------------------------  268
N2-C83      GGSGGGSEGGGSEGGGSEGGGSEGGGSGGGS-----------------------------  197
C-domain    ------------------------------------FDYEKMANANKGAMTENADENALQS   48
C83         ------------------------------------------------------------ wt pIII     DAKGKLDSVATDYGAAIDGFIGDVSGLANGNGATGDFAGSNSQMAQVGDGDNSPLMNNFR  360
N-C83       ---------------------------------------SQMAQVGDGDNSPLMNNFR  290
N*-C83      ---------------------------------------SQMAQVGDGDNSPLMNNFR  287
N2-C83      ---------------------------------------SQMAQVGDGDNSPLMNNFR  216
C-domain    DAKGKLDSVATDYGAAIDGFIGDVSGLANGNGATGDFAGSNSQMAQVGDGDNSPLMNNFR  108
C83         ----------------------------------------QMAQVGDGDNSPLMNNFR   41
                                                     ****************** wt pIII     QYLPSLPQSVECRPFVFGAGKPYEFSIDCDKINLFRGVFAFLLYVATFMYVFSTFANILR  420
N-C83       QYLPSLPQSVECRPFVFGAGKPYEFSIDCDKINLFRGVFAFLLYVATFMYVFSTFANILR  350
N*-C83      QYLPSLPQSVECRPFVFGAGKPYEFSIDCDKINLFRGVFAFLLYVATFMYVFSTFANILR  347
N2-C83      QYLPSLPQSVECRPFVFGAGKPYEFSIDCDKINLFRGVFAFLLYVATFMYVFSTFANILR  276
C-domain    QYLPSLPQSVECRPFVFGAGKPYEFSIDCDKINLFRGVFAFLLYVATFMYVFSTFANILR  168
C83         QYLPSLPQSVECRPFVFGAGKPYEFSIDCDKINLFRGVFAFLLYVATFMYVFSTFANILR  101
            ************************************************************ wt pIII     NKES  424(SEQ ID NO: 9)
N-C83       NKES  354(SEQ ID NO: 10)
N*-C83      NKES  351(SEQ ID NO: 11)
N2-C83      NKES  280(SEQ ID NO: 12)
C-domain    NKES  172(SEQ ID NO: 13)
C83         NKES  105(SEQ ID NO: 14)
            ****
```

FIGURE 5

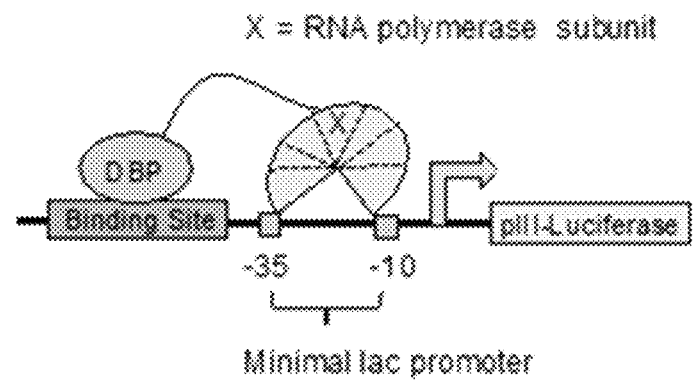
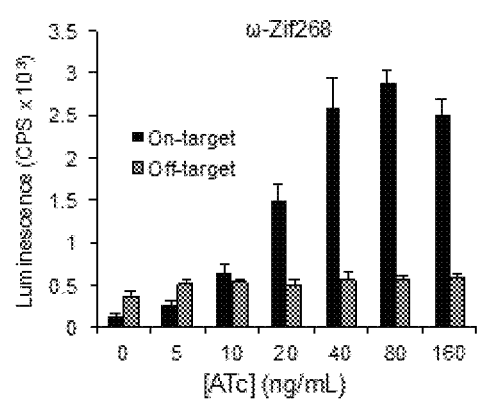
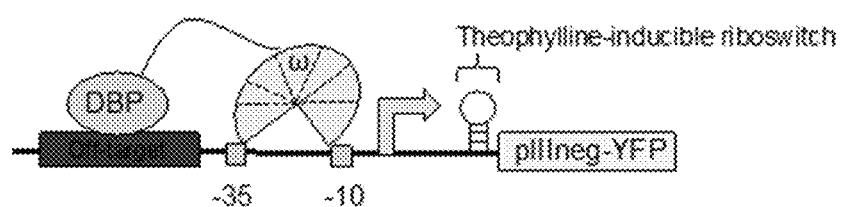
FIGURE 12

NEGATIVE SELECTION AND STRINGENCY MODULATION IN CONTINUOUS EVOLUTION SYSTEMS

RELATED APPLICATIONS

This application is a continuation of and claims priority under 35 U.S.C. § 120 to U.S. non-provisional application, U.S. Ser. No. 15/112,759, filed on Jul. 20, 2016, which is a national stage filing under 35 U.S.C. § 371 of international PCT application, PCT/US2015/012022, filed Jan. 20, 2015, which claims priority under 35 U.S.C. § 119 (e) to U.S. provisional patent application, U.S. Ser. No. 61/929,378, filed Jan. 20, 2014, the entire contents of each of which are incorporated herein by reference.

GOVERNMENT SUPPORT

This invention was made with government support under HR0011-11-2-0003 awarded by the Department of Defense/Defense Advanced Research Projects Agency; and N66001-12-C-4207 awarded by the National Institutes of Health. The government has certain rights in the invention.

REFERENCE TO AN ELECTRONIC SEQUENCE LISTING

The contents of the electronic sequence listing (H082470169US02-SEQ-KZM.txt; Size: 28,679 bytes; and Date of Creation: May 7, 2019) is herein incorporated by reference in its entirety.

BACKGROUND OF THE INVENTION

Proteins and nucleic acids employ only a small fraction of the available functionality of these types of molecules. There is currently considerable interest in modifying proteins and nucleic acids to diversify their functionality. Molecular evolution efforts include in vitro diversification of a starting molecule into related variants from which desired molecules are chosen. Methods used to generate diversity in nucleic acid and protein libraries include whole genome mutagenesis (Hart et al., *Amer. Chem. Soc.* (1999), 121:9887-9888), random cassette mutagenesis (Reidhaar-Olson et al., *Meth. Enzymol.* (1991), 208:564-86), error-prone PCR (Caldwell et al., *PCR Methods Applic.* (1992), 2:28-33) and DNA shuffling using homologous recombination (Stemmer, *Nature* (1994), 370:389-391). After diversification, molecules with novel or enhanced properties can be selected.

Conventional directed evolution involves discrete cycles of mutagenesis, transformation or in vitro expression, screening or selection, and gene harvesting and manipulation.[1,2] In contrast, evolution in nature occurs in a continuous, asynchronous format in which mutation, selection, and replication occur simultaneously. Although successful evolution is strongly dependent on the total number of rounds performed, the labor- and time-intensive nature of discrete directed evolution cycles limit many laboratory evolution efforts to a modest number of rounds.

In contrast, continuous directed evolution has the potential to dramatically enhance the effectiveness of directed evolution efforts by enabling an enormous number of rounds of evolution to take place in a single experiment with minimal researcher time or effort. While laboratories have explored various aspects of continuous evolution, no generalizable, continuous directed evolution system has been reported. In a landmark experiment, Joyce and co-workers engineered a ribozyme self-replication cycle in vitro and used this cycle to continuously evolve a ribozyme with RNA ligase activity (Wright, M. C. & Joyce, G. F. (1997) *Science* 276, 614-617). However, the foregoing example of continuous directed evolution cannot be easily adapted to evolve other biomolecules.

Continuous directed evolution minimally requires (i) continuous mutagenesis of the gene(s) of interest, and (ii) continuous selective replication of genes encoding molecules with a desired (on-target) activity. Several groups have developed methods to achieve continuous or rapid non-continuous cycles of mutagenesis. For example, Church and coworkers recently developed multiplex automated genome engineering (MAGE), a system capable of generating targeted diversity in *E. coli* through automated cycles of transformation and recombination (Wang, H. H. et al. (2009) *Nature* 460, 894-898). While these advances are capable of very efficiently creating gene libraries, they have not been linked to a rapid and general continuous selection and consequently have not enabled continuous directed evolution.

SUMMARY OF THE INVENTION

Many biomolecules, such as nucleic acids and proteins, have been generated in the laboratory with desired properties using continuous directed evolution. Continuous directed evolution strategies have been described in, for example, International Patent Application No. PCT/US2009/056194 and PCT/US2011/066747 and elsewhere[1,6,7], each of which is hereby incorporated by reference in its entirety. Described herein are strategies, systems, methods, reagents, and kits to expand the scope and capabilities of continuous directed evolution and address the needs of previously described laboratory evolution experiments. Generally, the continuous directed evolution of gene-encoded molecules can be linked to protein production in a host cell, for example, in an *E. coli* cell. Methods have been described for evolving a gene of interest by linking an activity of a molecule encoded by the gene of interest to the transfer of the gene of interest from cell to cell. The evolving gene of interest is transferred from host cell to host cell through a modified viral life cycle in a manner that is dependent on the activity of the molecule of interest. The gene of interest is replicated and mutated in a flow of host cells. The desired function of the gene of interest drives expression of a gene in the host cells that is essential for transfer of the gene from one cell to another, thus providing a selective advantage for those viral vectors in which the gene of interest has acquired a relevant gain-of-function mutation. Dozens of cycles of viral replication, mutation, and selection can occur in a single day of directed continuous evolution without human intervention.

In some embodiments, the continuous directed evolution method is phage-assisted continuous evolution (PACE). During PACE, a population of bacteriophage, each encoding a library member of an evolving gene, selectively replicates in a "lagoon" of continuously replenished host cells in a manner that depends on an activity of interest (FIGS. 1a and 1b).[1] A gene encoding a phage protein required for the production of infectious phage particles is under the control of a conditional promoter the activity of which depends on a gene product encoded by the gene of interest. Since phage life cycles are generally short (e.g., in the range of 10-20 minutes), many phage life cycles can occur in a single day of directed continuous evolution without human intervention.

Previous efforts of continuous directed evolution, such as PACE, utilized relatively high selection stringency to evolve biomolecules with desired properties such as broadened specificity. Improvements described herein include the ability to modulate the selection stringency to also allow weakly active or inactive biomolecule variants to access favorable mutations that enable their propagation under subsequent higher selection/stringency conditions. In addition, strategies included herein are for explicit negative selection against an undesired (off-target) property, which allows evolution of biomolecules with one or more altered properties (e.g., altered activity, specificity, stability and/or enantioselectivity). Thus, the combination of stringency modulation and negative selection enables the continuous directed evolution of biomolecules with a broader scope of evolved properties such as altered and highly specific new activities.

The continuous directed evolution methods herein utilize either or both of the following: 1) general modulation of selection stringency to enable otherwise inaccessible properties of biomolecules to be evolved directly from weakly active or inactive starting genetic libraries through a period of evolutionary drift that is independent of the activity being evolved; and/or 2) general negative selection to provide for continuous counter-selection against undesired properties of biomolecule variants.

In one aspect, general modulation of selection stringency to enable otherwise inaccessible properties of biomolecules to be evolved directly from weakly active or inactive starting genes through a period of evolutionary drift is controlled using a concentration of a small molecule in a manner independent of the activity being evolved. In some embodiments, the continuous directed evolution methods are performed using reduced or low selection stringency conditions. In some embodiments, the continuous directed evolution methods are performed using higher selection stringency conditions. In other embodiments, the continuous directed evolution methods are performed using conditions which combine reduced and higher selection stringency conditions. In some embodiments, low selection stringency conditions are used followed by high selection stringency conditions. In some embodiments, the methods optionally further use reduce or relatively more reduce selection stringency conditions or further use high or relatively higher selection stringency. In some embodiments, a set of conditions is used until an evolved product with certain properties is achieved or the level of a certain evolved product has been stabilized. In some embodiments, the method can optionally use one or more different sets of conditions to achieve the final desired evolved product or intermediate product.

In some embodiments, provided are methods for viral-assisted evolution of a gene product, the method comprising introducing a selection viral vector (such as a phagemid) comprising a gene to be evolved into a flow of host cells through a lagoon, wherein the host cells comprise viral genes required to package the selection viral vector into infectious viral particles, wherein at least one gene required to package the selection viral vector into infectious viral particles is expressed in response to a desired property of a gene product encoded by the gene to be evolved or an evolution product thereof; further wherein the host cells comprise a second copy of viral genes required to package the selection viral vector into infectious viral particles, wherein at least one gene required to package the selection viral vector into infectious viral particles is expressed in response to the concentration of a small molecule.

In some embodiments, provided are methods for viral-assisted evolution of a gene product, the method comprising introducing a selection viral vector (e.g., a selection phagemid) comprising a gene to be evolved into a flow of host cells through a lagoon, wherein the host cells contain a low selection stringency plasmid and a high selection stringency plasmid, wherein the concentration of a small molecule is used to control the level of selection stringency that dominates. The low selection stringency plasmid contains viral genes required to package the selection viral vector into infectious viral particles, wherein the viral gene is controlled by a small-molecule inducible promoter to allow evolutionary drift to occur. The high selection stringency plasmid contains viral genes required to package the selection viral vector into infectious viral particles, wherein the viral gene is controlled by an activity-dependent promoter, wherein the activity is the activity of the gene product being evolved. In some embodiments, the selection stringency is inversely proportional to the concentration of the small molecule. In some embodiments, the low selection stringency plasmid is dominant over the high selection stringency plasmid using a saturating or high concentration of the small molecule. In some embodiments, the high selection stringency plasmid is dominant over the low selection stringency plasmid using zero or a low concentration of the small molecule. In some embodiments, low selection stringency conditions allows evolutionary drift to occur, thereby allowing the propagation of weakly active or inactive starting genes. In some embodiments, high selection stringency enables the evolution of active starting genes.

One aspect provided herein is a drift promoter that is induced by the combination of prior viral infection and the presence of a small molecule inducer. The drift promoter is found on a drift plasmid in the host cell and enables evolutionary drift to occur. The drift promoter is used to support propagation of the selection viral vector by driving expression of a viral gene required to package the selection viral vector into infectious viral particles in a manner that is independent of the activity being evolved. In some embodiments, the drift promoter drives expression of a gene that encodes the pIII protein. In some embodiments, the low selection stringency plasmid contains the drift promoter. In some embodiments, the drift promoter reduces the host cell's resistance to viral infection. In some embodiments, the drift promoter supports activity-independent viral propagation (i.e., support viral propagation in a manner that is independent of the desired evolving activity from the selection viral vector). In some embodiments, the prior viral infection is a prior phage infection. In some embodiments, the viral propagation is phage propagation. In some embodiments, the small molecule inducer is a tetracycline or tetracycline analog. In some embodiments, the small molecule inducer is the tetracycline analog, anhydrotetracycline (ATc). In one embodiment, the small molecule is doxycycline. In one embodiment, the drift promoter is a combination of promoters comprising a tetracycline-inducible promoter ($P_{tet}$), which natively drives expression of the TetR repressor and TetA, the protein that pumps tetracycline out of the cell. In one embodiment, the drift promoter is a combination of promoters comprising an *E. coli* phage shock promoter ($P_{psp}$). In one embodiments, the drift promoter is $P_{psp\text{-}tet}$, which is a combination of a *E. coli* phage shock promoter ($P_{psp}$) with TetR operators installed at the position adjacent to the +1 transcription initiation site.

One aspect provided herein is a vector system in a host cell wherein one of the vectors is controlled by a small molecule inducer to evolve products from either the active or weakly active/inactive starting gene or genetic libraries cloned into the viral genome of a selection viral vector. In some embodiments, a vector system in a host cell contains a vector that is a drift plasmid encoding a viral gene required to package the selection viral vector into infectious viral particles, wherein the viral gene on the drift plasmid is under the control of a host cell drift promoter that is induced by the combination of prior viral infection and the presence of a small molecule inducer. In some embodiments, induction of the drift plasmid allows evolved products to be generated from weakly active or inactive starting genetic libraries. In one embodiment, host cell drift promoter comprises the Ppsp-tet promoter. In some embodiments, the drift plasmid contains a mutagenesis cassette under the control of a second small molecule inducible promoter. In some embodiments, the second small molecule inducible promoter is induced by arabinose.

In one aspect, the vector system further includes another vector that is an accessory plasmid encoding a viral gene required to package the selection viral vector into infectious viral particles, wherein the viral gene on the accessory plasmid is under the control of the desired evolving activity, wherein the desired evolving activity is produced from a selection viral vector.

In another aspect, a general negative selection against an undesired property is used in the continuous evolution system described. In some embodiments, the negative selection alters the activity, specificity, stability, or enantioselectivity of a biomolecule such as an enzyme. In some embodiments, the negative selection alters the specificity of a biomolecule such as an enzyme. In some embodiments, the evolved property resulting from negative selection or from both positive and negative selection is altered and/or broadened biomolecule specificity. For example, negative selection can be used to select an enzyme that is specific for a both the natural substrate and a non-natural substrate or select an enzyme that is specific for the non-natural substrate over the natural substrate. In some embodiments, negative selection is used to evolve the gene of interest. In some embodiments, a combination of selection stringency modulation and negative selection is used to generate an evolved product. In certain embodiments, the continuous evolution strategies utilize both negative and positive selection to evolve the gene of interest.

In another aspect, general negative selection to enable continuous counter-selection against undesired properties of biomolecules is accomplished using a dominant negative mutant gene of a viral gene required to package the selection viral vector into infectious viral particles, wherein the expression of the dominant negative mutant gene is controlled using, for example, a promoter inducible by a small molecule. In another embodiment, the expression of the dominant negative mutant gene is controlled using a promoter comprising an undesired DNA-binding site for the gene product. In some embodiments, the dominant negative mutant gene is expressed in response to an undesired activity of the gene being evolved or a product of the gene being evolved. In some embodiments, the dominant negative mutant gene, or expression product thereof, decreases or abolishes the ability of the selection viral vector to generate infectious viral particles. In some embodiments, the dominant negative mutant gene prevents or inhibits the detachment of nascent phage from the host cell membrane.

The above embodiments are useful in the various continuous directed evolution systems and methods described herein and in International Patent Applications, No. PCT/US2009/056194 and No. PCT/US2011/066747. In some of the above embodiments, the virus is a phage or phagemid.

In some embodiments, the viral-assisted continuous evolution is phage-assisted continuous evolution (PACE), further described herein. In some embodiments, the selection viral vector is a selection phage or phagemid (SP). In some embodiments, the selection phagemid is an M13 phagemid. In some embodiments, the viral genes required to package the selection viral vector into infectious viral particles is a phage gene required to package the selection phage into infectious phage particles, wherein at least one phage gene required to package the selection phage into phage particles is expressed in response to a desired property of a gene product encoded by the gene to be evolved or an evolution product thereof. In some embodiments, the host cells comprises a second copy of a phage gene required to package the selection phage vector into infectious phage particles, wherein at least one gene required to package the selection phage into phage particles is expressed in response to the concentration of a small molecule. In some embodiments, the phage gene required to package the selection phage vector is one or more genes selected from the gene which encodes the pII protein, the pIII protein, or the pVI protein. In some embodiments, the gene is one or more genes selected from gene II, gene III, or gene VI. In some embodiments, the phage gene required to package the selection phage vector into infectious phage particles is a gene which encodes the pIII protein. In some embodiments, the gene is gene III. In some embodiments, the dominant negative mutant gene encodes a dominant negative mutant protein of the pII protein (i.e., pII-neg protein), pIII protein (i.e, pIII-neg protein), or the pVI protein (i.e., pVI-neg protein). In some embodiments, the dominant negative mutant gene encodes a dominant negative mutant protein of the pIII protein (i.e, pIII-neg protein). In some embodiments, the dominant negative mutant gene is gene II-neg, gene III-neg, or gene VI-neg In some embodiments, the dominant negative mutant gene is gene III-neg.

In some embodiments, the dominant negative pIII protein comprises a mutant C domain, wherein the amino acids in the C-domain have been truncated. In some embodiments, the dominant negative pIII protein comprises an N-C83 domain, which has an internal deletion of 70 amino acids (i.e., amino acids 1-70) from the C-terminal domain of the pIII protein.[16]

Some aspects of this disclosure provide negative viral selection constructs. Such constructs are useful in the vector systems described herein. The negative viral selection constructs can be used with positive viral selection constructs. In some embodiments, the negative and positive viral selection constructs are located on different plasmids. In some embodiments, the negative viral selection construct is a negative phage selection construct. In some embodiments, the positive viral selection construct is a positive phage selection construct. In some embodiments, the negative selection construct comprises a nucleic acid encoding a dominant negative mutant of a viral gene product that decreases or abolishes the ability of the selection phagemids to generate infectious phage particles and a promoter driving expression of the encoded dominant negative mutant gene product, wherein the promoter comprises a DNA target site for an undesired property of a gene to be evolved. In some embodiments, the stringency of the negative and/or positive selection can be modified by decreasing or increasing the strength of a ribosome binding site upstream of the phage gene required to package the selection phage vector (such as a gene encoding pIII) and/or using a low or high copy number plasmid.

Another aspect provided herein is a vector system in one or more host cells comprising negative and positive viral selection constructs. In some embodiments, one or both the viral genes are controlled by small molecule inducers to evolve products toward the desired activity and away from the undesired activity. In some embodiments, one of the viral genes is driven by a promoter induced by the desired activity. In some embodiments, one viral gene is driven by a promoter induced by the desired activity and another viral gene is controlled by small molecule inducers. In some embodiments, the negative viral selection construct is driven by a promoter induced by a small molecule and the positive viral selection construct is driven by a promoter induced by the desired activity.

In a further aspect provided herein, a gene to be evolved encodes a DNA-binding gene product (e.g., polymerases, transcription factors, nucleases, or methylases). In some embodiments, expression of the gene required to package the selection phagemid into infectious particles is driven by a promoter comprising a desired DNA binding site for the DNA-binding gene product. In some embodiments, the DNA-binding gene product is a T7 RNA polymerase (T7 RNAP). In some embodiments, the promoter comprising a desired DNA binding site for the gene product is a T7 promoter ($P_{T7}$) or a T3 promoter ($P_{T3}$). In some embodiments, the evolved product is an evolved T7 RNA polymerase which has activity on the $P_{T3}$. In some embodiments the evolved product is a T7 RNA polymerase which is specific for the $P_{T3}$ over the $P_{T7}$. In some embodiments, the specificity for the evolved product for the non-native DNA-binding site exceeds the specificity for the product of the original gene to be evolved for the native DNA-binding site. In one embodiment, the specificity of an evolved T7 RNA polymerase for $P_{T3}$ over $P_{T7}$ exceeds the specificity of a wild-type T7 RNA polymerase for $P_{T7}$ over $P_{T3}$. In some embodiments, the T7 RNA polymerase is at least about 1.5-fold, 2-fold, 5-fold, 10-fold, 20-fold, 50-fold, 80-fold, 100-fold, 500-fold, 800-fold, 1000-fold, 3,000-fold, 5,000-fold, 8,000-fold, 10,000-fold, 12,000-fold, or 15,000-fold more specific for the $P_{T3}$ over the $P_{T7}$. In some embodiments, the T7 RNA polymerase is at least about 1.5-fold to 10-fold, 10-fold to 50-fold, 50-fold to 80-fold, 80-fold to 100-fold, 100-fold to 300-fold, 300-fold to 500-fold, 500-fold to 800-fold, 1000-fold to 3,000-fold, 3,000-fold to 5,000-fold, 5,000-fold to 8,000-fold, 8,000-fold to 10,000-fold, 10,000-fold to 12,000-fold, or 12,000-fold to 15,000-fold more specific for the $P_{T3}$ over the $P_{T7}$.

In some embodiments, the evolved product is a T7 RNA polymerase evolved from a T7 RNAP that is substrate-specific for $P_{T7}$ rather than from a T7 RNAP that is promiscuous. In some embodiments, expression of the dominant negative mutant gene is driven by a promoter comprising an undesired DNA-binding site for the DNA-binding gene product. In some embodiments, the undesired DNA binding site is an off-target DNA binding site. In some embodiments, the promoter is a T3 promoter ($P_{T3}$).

Further, some aspects of this invention provide kits comprising reagents, vectors, cells, software, systems, and/or apparatuses for carrying out the methods provided herein. For example, in some embodiments, a kit for controlling the selection stringency in a continuous directed evolution in a bacterial system is provided that includes a selection phage or phagemid; a drift plasmid; an accessory plasmid; optionally, a mutagenesis plasmid and/or a mutagen; and a host cell capable of producing infectious phage and amenable to phage infection. In some embodiments, a kit is provided that comprises a two-plasmid PACE vector system, as described in more detail elsewhere herein, for example, comprising a selection phage, a drift plasmid, an accessory plasmid, optionally, a mutagenesis plasmid, but no helper phage. In some embodiments, the kit further contains negative and/or positive selection constructs and optionally, a mutagenesis plasmid and/or a mutagen. In some embodiments, the kit optionally contains small molecule inducers. The kit typically also includes instructions for its use.

Other advantages, features, and uses of the invention will be apparent from the Detailed Description of Certain Embodiments, the Drawings, the Examples, and the Claims.

BRIEF DESCRIPTION OF THE DRAWINGS

FIG. 2A-E. Characterization of candidate gene III cassettes for modulating stringency and enabling drift. (a) Architecture of $P_{tet}$ (top; 14812), $P_{psp}$ (middle; 175e), and $P_{psp-tet}$ candidates (bottom; 175 g, h, k, m, and n variants). For the $P_{psp-tet}$ candidates, the numbers shown in parentheses refer to the constructs that contain the tetR-binding sites at the positions shown by the orange bar. tetR:tetR-binding sites, pspF:pspF-binding sites, σ70: *E. coli* sigma 70 RNAP promoter, σ54: *E. coli* sigma 54 RNAP promoter. (b) Architecture of plasmids highlighted in this figure. (c) Luciferase gene expression measurements of candidate drift cassettes in the presence and absence of ATc (which de-represses TetR) and IPTG (which de-represses lacI and induces pIV expression). pIV expression is used for these experiments to emulate filamentous phage infection and drive the $P_{psp}$ response. (d) Phage production from discrete cultures containing various drift constructs and SP-T7$_{WT}$ in the presence and absence of ATc (to induce gene III expression) and arabinose (to induce mutagenesis). Robust phage titers are produced regardless of drift cassette copy number or mutagenesis induction. (e) Assay for infection of recipient cells carrying the pTet-pIII cassette. A low proportion of yellow colonies indicates resistance to infection, as seen for recipient cells carrying the induced pTet construct.

FIG. 5. Sequence alignment of pIII-neg candidates and wild-type pIII. ClustalW2 (ebi.ac.uk/Tools/msa/clustalw2/) was used to align all pIII-neg candidates against full-length pIII. Sequences from top to bottom correspond to SEQ ID NOs: 9-14.

FIG. 12. Development of a DNA-binding continuous evolution system. Evaluation of a reporter system used to couple DNA binding to induction of gene III-luciferase expression and a reporter system used to couple DNA binding to an off-target sequence to production of pIIIneg-YFP.

DEFINITIONS

Figure 1:
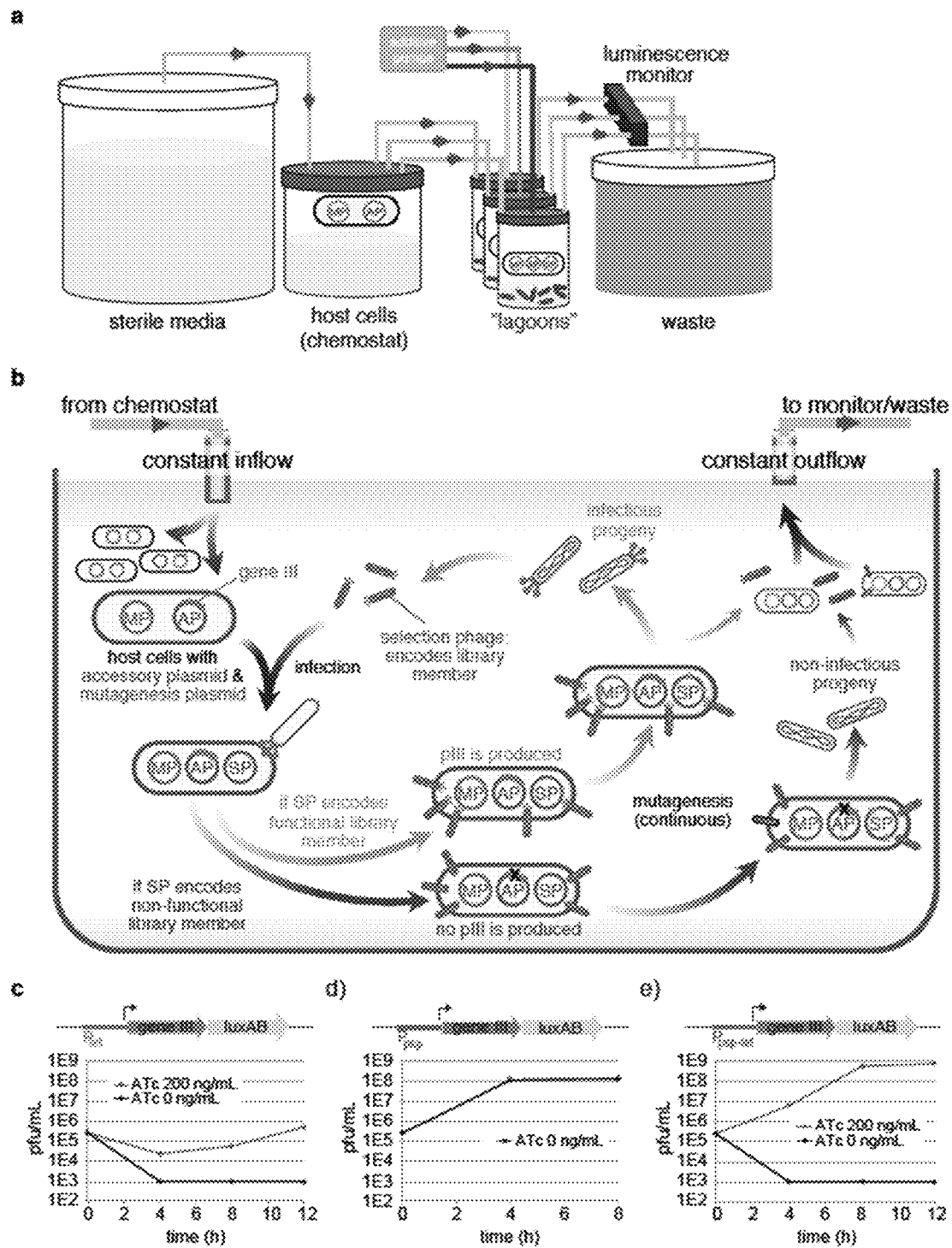
FIG. 1A-E. PACE overview and development of a gene III expression cassette that enables drift during continuous phage propagation. (a-b) During PACE, host *E. coli* cells continuously dilute an evolving population of filamentous bacteriophages in a fixed-volume vessel (a "lagoon", detailed in (b)). The lagoon is continuously drained to a waste container after passing through an in-line luminescence monitor that measures expression from a gene III-luciferase cassette on the AP. Dilution occurs faster than cell division but slower than phage replication. Each phage carries a protein encoding gene to be evolved instead of a phage gene (gene III) that is required for infection. Phage encoding active variants trigger gene III expression in proportion to the desired activity and consequently produce infectious progeny, while phage encoding less active variants produce fewer infectious progeny and are diluted out of the lagoon. (c-e) Cells harboring the indicated accessory plasmids (APs) with the indicated gene III-luxAB expression cassettes were used as recipients for phage propagation experiments using selection phages encoding the wild-type T7 RNA polymerase (SP-T7$_{WT}$). Data show representative single measurements of phage concentrations (n=1). (c) Using the tetracycline-inducible promoter, $P_{tet}$, to induce gene III expression with anhydrotetracycline (ATc) prior to phage infection inhibits infection and results in minimal phage propagation and low phage titers. (d) Using $P_{psp}$, an *E. coli* phage shock promoter, to express gene III only after infection takes place results in robust activity-independent phage propagation and high phage titers. (e) Infection- and ATc-dependent gene III expression using $P_{psp-tet}$ enables robust, activity-independent propagation.

The term "agent," as used herein, refers to any molecule, entity, or moiety. For example, an agent may be a protein, an amino acid, a peptide, a polynucleotide, a carbohydrate, a lipid, a detectable label, a binding agent, a tag, a metal atom, a contrast agent, a catalyst, a non-polypeptide polymer, a synthetic polymer, a recognition element, a linker, or chemical compound, such as a small molecule. In some embodiments, the agent is a binding agent, for example, a ligand, a ligand-binding molecule, an antibody, or an antibody fragment. Additional agents suitable for use in embodiments of the present invention will be apparent to the skilled artisan. The invention is not limited in this respect.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In general, a detectable label can fall into any one (or more) of five classes: I) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-$^{99}$m), $^{111}$In, $^{123}$I, $^{125}$I, $^{131}$I, $^{153}$Gd, $^{169}$Yb, and $^{186}$Re; II) a label which contains an immune moiety, which may be antibodies or antigens, which may be bound to enzymes (e.g., such as horseradish peroxidase); III) a label which is a colored, luminescent, phosphorescent, or fluorescent moieties (e.g., such as the fluorescent label fluorescein-isothiocyanate (FITC); IV) a label which has one or more photo affinity moieties; and V) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, SR (eds.) Green fluorescent protein: properties, applications, and protocols Methods of biochemical analysis, v. 47 Wiley-Interscience, Hoboken, N.J., 2006; and Chudakov, D M, et al., Physiol Rev. 90 (3): 1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue.

Continuous Evolution Concept

The term "continuous evolution," as used herein, refers to an evolution procedure, in which a population of nucleic acids is subjected to multiple rounds of (a) replication, (b) mutation, and (c) selection to produce a desired evolved product, for example, a nucleic acid encoding a protein with a desired activity, wherein the multiple rounds can be performed without investigator interaction and wherein the processes under (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired mutation in the gene of interest. Continuous evolution has been previously described in International Patent Application No. PCT/US2009/056194 and PCT/US2011/066747 and elsewhere[1,6,7], each of which is hereby incorporated by reference in its entirety. An example of a continuous evolution experiment is PACE, as further summarized herein The term "flow", as used herein in the context of host cells, refers to a stream of host cells, wherein fresh host cells are being introduced into a host cell population, for example, a host cell population in a lagoon, remain within the population for a limited time and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon.

Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "phage-assisted continuous evolution (PACE)," as used herein, refers to continuous evolution that employs selection phage as selection viral vectors.

The term "high selection stringency" refers to conditions which favor relatively active genetic variants and disfavor relatively weakly active or inactive genetic variants. By performing the continuous evolution conditions at a relatively high selection stringency, the bar for the activity level required to pass the selection conditions is set at a level that can exclude genetic variants that have low activity but high potential to evolve greater activity in subsequent rounds of continuous evolution. Alternatively, relatively high selection stringency encompasses the presence of a relatively high amount of the expression product of a viral gene required to package a selection viral vector into an infectious viral particle (e.g., pIII protein) and its effect on infectivity.

The term "low selection stringency" refers to conditions which favor relatively weakly active or inactive genetic variants and disfavor active genetic variants.

The term "gene variant thereof" refers to a variant that is at least about 50%, 60%, 70%, 80%, 90%, or 99% homologous to the original gene.

The term "dominant negative mutant" refers to a gene or gene variant thereof that encodes a gene product that antagonizes the gene product of a phage gene that decreases or abolishes packaging of the selection phagemids into infectious phage particles. Examples of a dominant negative mutant is the N-C83 variant which is a pIII protein comprising an N-C83 domain, which has an internal deletion of 70 amino acids (i.e., amino acids 1-70) from the C-terminal domain of the pIII protein. The amino acid sequence of the N-C83 variant is shown in FIG. 5, which includes other examples of pIII-neg variants. Other examples include the dominant negative mutant of the pIV protein (pIVneg) and other non-phage conventional counter selection genes. Alternative methods to a dominant negative mutant include, for example, overexpression of phage proteins which, for example, bridge multiple interactions in phage packaging. For example, overexpression of pVI prevents pIII from being incorporated in to the phage particle or overexpression of pIX/pVII may reduce the ability of pVIII to get incorporated into the phage particle.

The term "negative selection," as used herein, refers to the removal of undesired mutations from the gene of interest.

The term "positive selection," as used herein, refers to the retention of desired mutations in the gene of interest.

The term "evolutionary drift," as used herein, refers to the accumulation of sequence differences that have minimal or no impact on the fitness of an organism; such neutral mutations are random and are not being actively selected or accumulation of mutations in the gene of interest that do not dramatically affect the activity or function of said gene. For example, sequence polymorphisms arise randomly in a population, most of which have no effect on function. Stochastic processes allow a small fraction of these to increase in frequency until they are fixed in a population; these are detectable as neutral substitutions in interspecies comparisons. In some embodiments, a drift plasmid is used as described herein and the expression of a viral gene required to package the selection viral vector into infectious viral particles is driven by a small molecule. Thus, evolutionary drift is allowed to occur by making the expression of a viral gene required to package the selection viral vector into infectious viral particles to be independent of the desired activity being evolved. A period of drift has reduced (possibly to zero) selection stringency that allows evolving sequences to "drift", or mutate without regard to the selection consequences. Accumulation of mutations in the gene of interest in a way that is independent of activity gene product of the gene of interest.

Viral Vectors

The term "viral vector," as used herein, refers to a nucleic acid comprising a viral genome that, when introduced into a suitable host cell, can be replicated and packaged into infectious viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "nucleic acid," as used herein, refers to a polymer of nucleotides. The polymer may include natural nucleosides (i.e, adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "protein," as used herein refers to a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "gene to be evolved," "gene of interest," or "gene of interest to be evolved," as used herein, are used interchangeably and refers to a nucleic acid construct comprising a nucleotide sequence encoding a gene product of interest, for example, a gene product to be evolved in a continuous evolution process as provided herein. In some embodiments, the gene product to be evolved has an evolved property such as activity, specificity, stability, or enantioselectivity. The term includes any variations of a gene of interest that are the result of a continuous evolution process according to methods provided herein. For example, in some embodiments, a gene of interest is a nucleic acid construct comprising a nucleotide sequence encoding a protein to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protein to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome.

The term "function of a gene of interest," as interchangeably used with the term "property of a gene of interest," refers to a property of a gene product, for example, a nucleic acid or a protein, encoded by the gene of interest. For example, a function of a gene of interest may be an enzymatic activity (e.g., an enzymatic activity resulting in the generation of a reaction product, phosphorylation activity, phosphatase activity, nuclease activity, methylase activity, glycosylation activity, etc.), altered and/or broadened substrate specificity, stability such as thermostability, enantioselectivity, an ability to activate transcription (e.g., transcriptional activation activity targeted to a specific promoter sequence), a bond-forming activity, (e.g., an enzymatic activity resulting in the formation of a covalent bond), or a binding activity (e.g., a protein, DNA, or RNA binding activity).

The terms "evolved product" and "evolution product" refer to a resulting gene product that was evolved from a gene of interest in a laboratory evolution experiment. The resulting gene product can also be an intermediate gene product that will be subjected to further evolution experiments. A gene product can be an RNA or protein. For example, a T7 RNAP that was evolved in a PACE experiment to be specific for the $P_{T3}$ would be an evolution product.

The term "starting gene" or "starting genetic library," as used herein, refers to a gene or library of one or more original starting gene(s) which are cloned into a viral genome (such as a phage genome) in the selection viral vector (such as a selection phage). Continuous evolution strategies are then used to evolve the starting genetic library into a library of evolved genes encoding evolution products. For example, the viral genome contains the gene of interest to be evolved, which may or may not contain one or more mutations to begin with. A starting genetic library can be a clonal population of single starting gene, or a library prepared by conventional methods, or a population from a previous round of PACE. For example, the starting library can be generated by any means of DNA manipulations, including but not limited to error-prone PCR, saturation mutagenesis, bacterial mutator strains or moderately modified libraries based on prior knowledge of the biomolecule to be evolved.

The term "viral particle," as used herein, refers to a viral genome, for example, a DNA or RNA genome, that is associated with a coat of a viral protein or proteins, and, in some cases, with an envelope of lipids. In some embodiments, the viral particle is a phage particle. For example, a phage particle comprises a phage genome encapsulated by one or more coat proteins encoded by the wild-type phage genome.

The term "infectious viral particle," as used herein, refers to a viral particle able to transport its viral genome into a suitable host cell. Not all viral particles are able to transfer the viral genome to a suitable host cell. Particles unable to accomplish this are referred to as a non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles. In some embodiments, an infectious viral particle is an infectious phage particle. In some embodiments, an infectious phage particle is an infectious M13 phage particle.

The term "viral life cycle," as used herein, refers to the viral reproduction cycle comprising insertion of the viral genome into a host cell, replication of the viral genome in the host cell, and packaging of a replication product of the viral genome into a viral particle by the host cell. In some embodiments, a viral life cycle is a "phage life cycle."

In some embodiments, the viral vector provided is a phage. The terms "phage" and "bacteriophage" refer to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art, and non-limiting examples of phages that are useful for carrying out the methods provided herein are 2 (Lysogen), T2, T4, T7, T12, R17, M13, MS2, G4, P1, P2, P4, Phi X174, N4, Φ6, and Φ29. In certain embodiments, the phage utilized in the present invention is M13 phage. Additional suitable phages and host cells will be apparent to those of skill in the art, and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; 1st edition (December 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

In some embodiments, the phage is a filamentous phage. In some embodiments, the phage is an M13 phage. M13 phages are well known to those skilled in the art, and the biology of M13 phages has been studied extensively. A schematic representation of the wild-type M13 genome is provided in International Application No. PCT/US2011/066747, filed Dec. 22, 2011, published as WO2012/088381., Wild-type M13 phage particles comprise a circular, single-stranded genome of approximately 6.4 kb. The wild-type genome includes eleven genes, gI-gXI, which, in turn, encode the eleven M13 proteins, pI-pXI, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the conjugative pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild-type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all eleven genes proceeds in same direction. One of the phage-encode proteins, pII, initiates the generation of linear, single-stranded phage genomes in the host cells, which are subsequently circularized, and bound and stabilized by pV.

The circularized, single-stranded M13 genomes are then bound by pVIII at the inner bacterial membrane, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild-type genes, and/or inserting a heterologous nucleic acid construct into the genome.

The M13 phage has been well characterized and the genomic sequence of M13 has been reported. Representative M13 genomic sequences can be retrieved from public databases and an exemplary sequence is provided in entry V00604 of the National Center for Biotechnology Information (NCBI) database (ncbi.nlm.nih.gov). For example, an exemplary phage M13 genome can be found under the GI number 56713234. The protein product for gI, gII, gIII, gIV, gV, gVI, gVII, VIII, gIX, gX, and gXI are also known.

The term "selection phage," as used herein interchangeably with the term "selection plasmid," refers to a modified phage that comprises a gene of interest to be evolved and lacks a full-length gene encoding a protein required for the generation of infective phage particles. For example, some M13 selection phage provided herein comprise a nucleic acid sequence encoding a protein to be evolved, e.g., under the control of an M13 promoter, and lack all or part of a phage gene encoding a protein required for the generation of infective phage particles, e.g., gI, gII, gIII, gIV, gV, gVI, gVII, VIII, gIX, gX, or gXI, or any combination thereof. For example, some M13 selection phage provided herein comprise a nucleic acid sequence encoding a protein to be evolved, e.g., under the control of an M13 promoter, and lack all or part of a gene encoding a protein required for the generation of infective phage particles, e.g., the gIII gene encoding the pIII protein.

The term "helper phage," as used herein interchangeable with the terms "helper phagemid" and "helper plasmid," refers to an optional nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes required for the generation of phage particles. Helper phages are useful to allow modified phages that lack a gene required for the generation of phage particles to complete the phage life cycle in a host cell. Typically, a helper phage will comprise the genes required for the generation of phage particles that are lacking in the phage genome, thus complementing the phage genome. In the continuous evolution context, the helper phage typically complements the selection phage, but both lack a phage gene required for the production of infectious phage particles.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

Accessory Plasmids, Drift Plasmids, and Helper Constructs

The term "accessory plasmid," as used herein, refers to a plasmid comprising a gene required for the generation of infectious viral particles under the control of a conditional promoter. In one embodiment of the context of continuous evolution described herein, the conditional promoter of the accessory plasmid is typically activated by a function of the gene of interest to be evolved. Accordingly, the accessory plasmid serves the function of conveying a competitive advantage to those viral vectors in a given population of viral vectors that carry a gene of interest able to activate the conditional promoter. Only viral vectors carrying an "activating" gene of interest will be able to induce expression of the gene required to generate infectious viral particles in the host cell, and, thus, allow for packaging and propagation of the viral genome in the flow of host cells. Vectors carrying non-activating versions of the gene of interest, on the other hand, will not induce expression of the gene required to generate infectious viral vectors, and, thus, will not be packaged into infectious viral particles that can infect host cells. In another embodiment, the conditional promoter is activated by a small molecule inducer and its activation is independent of the gene of interest.

In some embodiments, the conditional promoter of the accessory plasmid is a activated by the transcriptional activity of which can be regulated over a wide range, for example, over 2, 3, 4, 5, 6, 7, 8, 9, or 10 orders of magnitude by the activating function, for example, function of a protein encoded by the gene of interest. In some embodiments, the level of transcriptional activity of the conditional promoter depends directly on the desired function of the gene of interest. This allows for starting a continuous evolution process with a viral vector population comprising versions of the gene of interest that only show minimal activation of the conditional promoter. In the process of continuous evolution, any mutation in the gene of interest that increases activity of the conditional promoter directly translates into higher expression levels of the gene required for the generation of infectious viral particles, and, thus, into a competitive advantage over other viral vectors carrying minimally active or loss-of-function versions of the gene of interest.

The stringency of selective pressure imposed by the accessory plasmid in a continuous evolution procedure as provided herein can be modulated. In some embodiments, the use of low copy number accessory plasmids results in an elevated stringency of selection for versions of the gene of interest that activate the conditional promoter on the accessory plasmid, while the use of high copy number accessory plasmids results in a lower stringency of selection. The terms "high copy number plasmid" and "low copy number plasmid" are art-recognized, and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000. The copy number of an accessory plasmid will depend to a large part on the origin of replication employed. Those of skill in the art will be able to determine suitable origins of replication in order to achieve a desired copy number. The following table lists some non-limiting examples of vectors of different copy numbers and with different origins of replication.

| Plasmids | | | |
|---|---|---|---|
| pUC vectors | pMB1* | 500-700 | high copy |
| pBluescript ® vectors | ColE1 | 300-500 | high copy |
| pGEM ® vectors | pMB1* | 300-400 | high copy |
| pTZ vectors | pMB* | >1000 | high copy |
| pBR322 and derivatives | pMB1* | 15-20 | low copy |
| pACYC and derivatives | p15A | 10-12 | low copy |
| pSC101 and derivatives | pSC101 | ~5 | very low copy |

*The pMB1 origin of replication is closely related to that of ColE1 and falls in the same incompatibility group. The high-copy plasmids listed here contain mutated versions of this origin.

It should be understood that the function of the accessory plasmid, namely to provide a gene required for the generation of viral particles under the control of a conditional promoter the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using an different vector, for example, a phagemid, a cosmid, a phage, a virus, or an artificial chromosome. Additional ways to confer accessory plasmid function to host cells will be evident to those of skill in the art, and the invention is not limited in this respect.

The term "drift plasmid," as used herein refers to an accessory plasmid that allows evolutionary drift to occur in response to a concentration of a small molecule inducer. In some embodiments, the drift plasmid contains a mutagenesis cassette under the control of another small molecule. In an embodiment, the drift plasmid contains a gene required to package the selection viral vector into an infectious viral particle such as gene III or a gene variant thereof.

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, lactose-inducible promoters (e.g., $P_{lac}$), arabinose-inducible promoters ($P_{bad}$), homoserine lactone-inducible promoters (e.g., $P_{lux}$), tetracycline-inducible promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "riboswitch" refers to regions of mRNA that adopt well defined secondary and tertiary structures. They directly bind certain small molecules with high affinity and selectivity. Their cellular function is to repress or activate essential genes (for example those involved in biosynthesis and transport of metabolites) in response to the intracellular level of their ligand. Ligand binding stabilizes either an "on" or "off" conformation which alters mRNA transcription, protein translation or mRNA splicing. Riboswitch can control gene expression at the transcriptional or translational stage. In some embodiments, the expression of a gene described herein, such as gene III, gene III-neg, is controlled through small molecule-RNA interactions. For example, gene expression is controlled by a regulatable gene expression construct comprising a nucleic acid molecule encoding an RNA comprising a riboswitch operably linked to a gene described herein, wherein the riboswitch comprises an aptamer domain and an expression platform domain, wherein the riboswitch regulates expression of the gene described herein. For example, riboswitches are composed of an RNA aptamer domain which acts as a selective receptor for the binding of a specific metabolite or small-molecule ligand. The binding of the ligand to aptamer induces a conformational change of the riboswitch that is able to adopt one of two possible conformations in response to ligand binding leading to either an increase or decrease in the expression of the RNA transcript. Riboswitches can be naturally-occurring or synthetic. Riboswitch can be responsive to various small molecules or metabolites. For example, binding of hypoxanthine, guanine, or xanthine to a particular riboswitch can control transcription of genes. The small molecule can be endogenous or non-endogenous. For example, theophylline-activated riboswitches are useful for controlling the translation of a dominant negative mutant gene as described further herein.

Mutagens and Mutagenesis-Promoting Expression Constructs

The term "mutagen," as used herein, refers to an agent that induces mutations or increases the rate of mutation in a given biological system, for example, a host cell, to a level above the naturally-occurring level of mutation in that system. Some exemplary mutagens useful for continuous evolution procedures are provided elsewhere herein and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene, 3-Chloro-4-(dichloromethyl)-5-hydroxy-2 (5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl) acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9) and t-butyl hydroperoxide (BHP) (CAS no. 75-91-2). Additional mutagens can be used in continuous evolution procedures as provided herein, and the invention is not limited in this respect.

Ideally, a mutagen is used at a concentration or level of exposure that induces a desired mutation rate in a given host cell or viral vector population, but is not significantly toxic to the host cells used within the average time frame a host cell is exposed to the mutagen or the time a host cell is present in the host cell flow before being replaced by a fresh host cell.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene.

Host Cells

The term "host cell," as used herein, refers to a cell that can host a viral vector useful for a continuous evolution process as provided herein. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage and the host cell is a bacterial cell. In some embodiments, the host cell is an $E.$ $coli$ cell. Suitable $E.$ $coli$ host strains will be apparent to those of skill in the art, and include, but are not limited to, New England Biolabs (NEB) Turbo, Top10F', DH12S, ER2738, ER2267, and XL1-Blue MRF'. These strain names are recognized in the art, and the genotype of these strains has been well characterized. It should be understood that the above strains are exemplary only and that the invention is not limited in this respect.

The term "fresh," as used herein interchangeably with the terms "non-infected" or "uninfected" in the context of host cells, refers to a host cell that has not been infected by a viral vector comprising a gene of interest as used in a continuous evolution process provided herein. A fresh host cell can, however, have been infected by a viral vector unrelated to the vector to be evolved or by a vector of the same or a similar type but not carrying the gene of interest.

In some embodiments, the host cell is a prokaryotic cell, for example, a bacterial cell. In some embodiments, the host cell is an $E.$ $coli$ cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some PACE embodiments, for example, in embodiments employing an M13 selection phage, the host cells are $E.$ $coli$ cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of $E.$ $coli$ cells with certain phage, for example, with M13 phage. For example, in some embodiments, the host cells for M13-PACE are from the S109 strain with the genotype F'proA$^+$B$^+$ Δ(lacIZY) zzf:: Tn10 (TetR)/endA1 recA1 galE15 galK16 nupG rpsL ΔlacIZYA araD139 Δ(ara,leu) 7697 mcrA Δ(mrr-hsdRMS-mcrBC) proBA::pir116 λ$^-$. In another example, the host cells are from the S1030 strain.

Lagoons, Cellstats, Turbidostats, Chemostats

The term "lagoon," used herein interchangeably with the term "cell stat," as used herein, refers to a vessel through which a flow of host cells is directed. When used for a continuous evolution process as provided herein, a lagoon typically holds a population of host cells and a population of viral vectors replicating within the host cell population, wherein the lagoon comprises an outflow through which host cells are removed from the lagoon and an inflow through which fresh host cells are introduced into the lagoon, thus replenishing the host cell population. In some embodiments, the flow of cells through the lagoon is regulated to result in an essentially constant number of host cells within the lagoon. In some embodiments, the flow of cells through the lagoon is regulated to result in an essentially constant number of fresh host cells within the lagoon.

The term "turbidostat," as used herein, refers to a culture vessel comprising host cells in suspension culture, in which the turbidity of the culture medium is substantially essentially constant over time. In some embodiments, the turbidity of a suspension culture, for example, of bacterial cells, is a measure for the cell density in the culture medium. In some embodiments, a turbidostat comprises an inflow of fresh media and an outflow, and a controller that regulates the flow into and/or out of the turbidostat based on the turbidity of the suspension culture in the turbidostat.

The term "chemostat," as used herein, refers to a host cell culture system maintained at constant nutrient flow rate as opposed to a host cell culture system maintained at constant turbidity (turbidostats). Chemostats also do not require turbidity monitoring as turbidostats require.

DETAILED DESCRIPTION OF CERTAIN EMBODIMENTS OF THE INVENTION

Some aspects of this invention provide methods for the continuous evolution of a biomolecule, for example, of a gene of interest (or gene to be evolved) or a gene product. Some aspects of this invention provide experimental configurations, systems, apparatuses, reagents, software, and materials for the continuous evolution methods described herein. Vectors, vector systems, and kits for continuous evolution as described herein are also provided. The continuous directed evolution methods provided herein utilize the following: 1) general modulation of selection stringency to enable otherwise inaccessible properties of biomolecules to be evolved directly from weakly active/inactive starting genes through a period of evolutionary drift; and/or 2) general negative selection to enable counter-selection against undesired activities of biomolecules.

The foregoing new aspects related to selection stringency and negative selection are useful because they expand the scope and capabilities of continuous directed evolution strategies and address the needs of previously described laboratory evolution experiments. For example, the new aspects of continuous evolution methods described generally enables the evolution of enzymes with broadened and/or altered specificities. Prior strategies for continuous directed evolution, such as PACE described below, have used relatively high selection stringency to evolve biomolecules with desired properties such as produce biomolecules with broadened specificity. Several needs were identified through these early efforts. First, it was observed that the use of high selection stringency was not well suited for weakly active or inactive biomolecule variants to be evolved. For example, previous PACE experiments evolved T7 RNA polymerase (T7 RNAP) mutants that initiate transcription at the T3 promoter ($P_{T3}$), which differed from the T7 promoter ($P_{T7}$) at six of 17 base positions.[1,6,7] When wild-type T7 RNA polymerase was challenged to evolve activity directly on $P_{T3}$, active mutants did not emerge, and the phage in the lagoon washed out, indicating that the stringency of this initial selection was too high.[1,6,7] The successful evolution of activity on $P_{T3}$ instead required initial selection on a hybrid T7/T3 promoter ($P_{T7/T3}$) that served as an evolutionary stepping-stone toward the $P_{T3}$ selection. For many potential applications of PACE such as protein-protein interactions and biosynthesis applications, suitable intermediate substrates may not be obvious or accessible. In addition, the methods herein may be useful for substrates in which the subcomponents are not simple, modular building blocks (e.g., small molecule substrates). To address this need, a general modulator of selection stringency was developed in which continuous directed evolution such as PACE is initiated under reduced selection stringency to allow weakly active or inactive variants to access favorable mutations that enable propagation under subsequent higher-selection stringency conditions. In some embodiments, the selection stringency is modulated by a small molecule inducer.

Second, it was further observed that the T7 RNAPs evolved to recognize $P_{T3}$ retained most or all of their activity on $P_{T7}$. In the absence of explicit negative selection against undesired activity, the evolution of novel substrate recognition often results in enzymes with broadened, rather than truly altered specificity.[8,9] For many potential targets of PACE, including proteases, binding proteins, and genome engineering enzymes, evolved proteins will require exceptional substrate specificity to function in complex cellular environments containing many potential off-target substrates. To address this need, a general negative selection for PACE in which selection viral vectors such as a selection phage (SP) encoding variants with undesired activities, such as off-target substrate recognition, incur a replicative penalty.

Accordingly, provided herein are solutions that address the foregoing needs associated with continuous directed evolution methods. Described herein are strategies, systems, methods, reagents, and kits to expand the scope and capabilities of continuous directed evolution and address the needs of previously described laboratory evolution experiments. One solution is to allow evolutionary drift to take place using reduced selection stringency. Another solution is to negatively select away from undesired properties.

As further described in the Examples, T7 RNAP mutants that have wild-type like activity on $P_{T3}$ and remarkable specificity for $P_{T3}$ over $P_{T7}$ have been evolved in a single PACE experiment. This evolved degree of specificity exceeds that of wild-type T7 RNAP for $P_{T7}$ over $P_{T3}$, as well as that of wild-type T3 RNAP for $P_{T3}$ over $P_{T7}$. The combination of stringency modulation and negative selection enabled the evolution of polymerases with ~10,000-fold changes in specificity in a total time of three days. Together, these developments bring to PACE two capabilities recognized to be important in certain laboratory evolution efforts. These capabilities also expand the scope of PACE to include the evolution of biomolecules that possess radically altered properties such as altered and highly specific new activities. For example, biomolecules to be evolved include, e.g., nucleic acid binding proteins, proteases, recombinases, protein-protein interactions, genome engineering enzymes, biosynthetic clusters, endoribonucleases, and polymerases.

Overview of PACE Components

Phage-assisted continuous evolution (PACE), which has been previously described.[1,6,7] Briefly, host cells continuously dilute an evolving population of bacteriophages in a fixed volume vessel (a "lagoon") wherein each bacteriophage encodes a library member of an evolving gene. In general, dilution of the lagoon occurs faster than host cell division but slower than phage replication, ensuring that the phage accumulate mutations. Each phage, referred to as a selection phage (SP), carries a protein-encoding gene to be evolved instead of a phage gene (e.g., gene III) that is required for infection. The phage gene required for infection has been moved from the phage genome to an accessory plasmid (AP) carried by the host cells. Gene III encodes the phage protein pIII, which is essential for infectious phage production. Phage encoding active variants trigger host-cell expression of gene III in proportion to the desired property (or "property of interest") such that only SP encoding active library members induce the expression of pIII and the production of infectious progeny phage. Infectious progeny are consequently produced, but phage encoding less-active variants produce less infectious progeny that are diluted out of the lagoon. A mutagenesis cassette is also provided to allow the gene of interest to be mutated and evolved. In an embodiment, mutagenesis plasmid (MP), which contains a gene expression cassette encoding a mutagenesis-promoting gene product, enables small-molecule control over the mutation rate during phage replication. In another embodiment, the mutagenesis cassette is found on the drift plasmid, as further described herein. The host cell is contacted with the inducer, for example, in the lagoon, which induces expression of the mutagenesis promoting gene in the host cells. Infectious progeny phage can infect fresh host cells flowing into the lagoon and thereby continue to undergo additional cycles of selection, replication, and mutation. A mutated replication product of the viral vector, encoding an evolved protein, is isolated from the population of host cells.

In some embodiments, the bacteriophage is an M13 filamentous bacteriophage. The pIII expression construct contains a conditional promoter regulating the expression of the pIII gene (i.e, gene III). In some embodiments, the activity of the conditional promoter depends on a desired function of a gene product encoded by the gene of interest. In some embodiments, the conditional promoter's activity can also depends on the presence of an inducer. For example, the conditional promoter is any inducible promoter known in the art such as an arabinose-inducible promoter, wherein the inducer is arabinose.

The desired or undesired property of a gene product can be, for example, a binding activity or an enzymatic activity (such as a polymerase activity, a recombinase activity, a phosphotransferase activity, a kinase activity, a phosphatase activity, or a protease activity). For example, in certain embodiments, it is the activity of the wild-type gene product such as cleavage of a wild-type protease cleavage site, phosphorylation of a wild-type site, recognition of substrate recognized by the wild-type enzyme, etc. It could also be activity of the gene product of interest to a site/substrate that is similar/homologous to the wild-type site/substrate or a site/substrate that is similar/homologous to the target site/substrate of the evolution itself.

While selection phages (SP) and helper phages (HP) are described in the context of the PACE embodiment, it should be noted herein that SP and HP can also refer to the corresponding counterparts for the viral-assisted continuous evolution experiments. The counterpart to SP is viral vectors, and the counterpart to HP is a helper plasmid.

In some embodiments, a gene of interest (or gene to be evolved) is transferred from cell to cell in a manner dependent on the activity of the gene of interest. In some embodiments, the gene of interest is transferred in a manner independent on the activity of the gene of interest. In some embodiments, the transfer vector is a virus or infectious virus, for example, a bacteriophage. In some embodiments, the viral vector is a phage vector that infects bacterial host cells. In some embodiments, the transfer vector is a retroviral vector, for example, a lentiviral vector or a vesicular stomatitis virus vector that infects human or mouse cells. In some embodiments, the transfer vector is a conjugative plasmid transferred from a donor bacterial cell to a recipient bacterial cell.

In some embodiments, the nucleic acid vector comprising the gene of interest is a phage, a viral vector, or naked DNA (e.g., a mobilization plasmid). In some embodiments, transfer of the gene of interest from cell to cell is via infection, transfect ion, transduction, conjugation, or uptake of naked DNA, and efficiency of cell-to-cell transfer (e.g., transfer rate) is dependent on an activity of a product encoded by the gene of interest. For example, in some embodiments, the nucleic acid vector is a phage harboring the gene of interest, and the efficiency of phage transfer (via infection) is dependent on an activity of the gene of interest in that a protein required for the generation of phage particles (e.g., pIII for M13 phage) is expressed in the host cells only in the presence of the desired activity of the gene of interest. In another example, the nucleic acid vector is a retroviral vector, for example, a lentiviral or vesicular stomatitis virus vector harboring the gene of interest, and the efficiency of viral transfer from cell to cell is dependent on an activity of the gene of interest in that a protein required for the generation of viral particles (e.g., an envelope protein, such as VSV-g) is expressed in the host cells only in the presence of the desired activity of the gene of interest. In another example, the nucleic acid vector is a DNA vector, for example, in the form of a mobilizable plasmid DNA, comprising the gene of interest, that is transferred between bacterial host cells via conjugation, and the efficiency of conjugation-mediated transfer from cell to cell is dependent on an activity of the gene of interest in that a protein required for conjugation-mediated transfer (e.g., traA or traQ) is expressed in the host cells only in the presence of the desired activity of the gene of interest. Host cells contain F plasmid lacking one or both of those genes.

For example, some embodiments provide a continuous evolution system, in which a population of viral vectors comprising a gene of interest to be evolved replicates in a flow of host cells, e.g., a flow through a lagoon, wherein the viral vectors are deficient in a gene encoding a protein that is essential for the generation of infectious viral particles, and wherein that gene is comprised in the host cell under the control of a conditional promoter that can be activated by a gene product encoded by the gene of interest, or a mutated version thereof. In some embodiments, the activity of the conditional promoter depends on a desired function of a gene product encoded by the gene of interest. Viral vectors, in which the gene of interest has not acquired a mutation conferring the desired function, will not activate the conditional promoter, or only achieve minimal activation, while any mutation in the gene of interest that confers the desired mutation will result in activation of the conditional promoter. Since the conditional promoter controls an essential protein for the viral life cycle, activation of this promoter directly corresponds to an advantage in viral spread and replication for those vectors that have acquired an advantageous mutation.

Modulation of Selection Stringency

Provided herein is a method for modulating the selection stringency in viral-assisted continuous evolution experiments. In some embodiments, the selection stringency is modulated by regulating the expression of a gene required for the generation of infectious viral particles (e.g., infectious phages). Generally, the gene required for the generation of infectious viral particles is on an accessory plasmid (AP) or on a drift plasmid (DP). A drift plasmid allows evolutionary drift to take place to evolve weakly active or inactive gene variants. The expression of a gene required for the generation of infectious viral particles produces a protein required for the generation of infectious viral particles. In some embodiments, the gene required for the generation of infectious viral particles is gene III, which expresses the protein pIII needed to generate infections phage. In some embodiments, the modulation of the selection stringency is independent of the desired activity to be evolved. In some embodiments, regulation of the expression of the gene required for the generation of infectious viral particles is under the control of a small molecule inducible promoter (i.e., chemically-regulated promoters) and therefore, is dependent on the concentration of a small molecule. Examples of small molecule inducible promoters are known in the scientific literature (see, e.g., Yamamoto et. al., 2001, Neurobiology of Disease, 8:923-932). Non-limiting examples of small molecule inducible promoters include lux promoters (e.g. $P_{lux}$ from *vibrio fishceri* induced by N-(3-oxohexanoyl)-L-homoserine lactone (OHHL)); alcohol-regulated promoters (e.g., alcohol dehydrogenase I promoter (alcA), lac promoter (e.g., $P_{lac}$), arabinose-inducible promoters (e.g., Para), tetracycline-inducible promoters (e.g., $P_{tet}$), steroid-inducible promoters, and tamoxifen-inducible promoters. In some embodiments, the small molecule inducible promoter is a TetA promoter ($P_{tet}$). In some embodiments, the small molecule is tetracycline or tetracycline analogs. In some embodiments, the small molecule is anhydrotetracycline (ATc). In one embodiment, the small molecule is doxycycline. In one embodiment, the host cell drift promoter is partly a tetracycline-inducible promoter ($P_{tet}$), which drives expression of the TetR repressor and TetA, the protein that pumps tetracycline out of the cell. In the absence of tetracycline or its analogs, TetR binds to the TetR operator sites and prevents transcription. In the presence of tetracycline or its analogs, TetR binds to tetracycline or a tetracycline analog, which induces a conformational change, making it unable to interact with the operator, so that target gene expression can occur.

In some embodiments, the host cell becomes viral infection-resistant prior to encountering the viral particle, thereby preventing viral propagation. For example, low levels of pIII, such as the levels expressed at the beginning of a PACE experiment, have been shown to render cells resistant to filamentous phage infection.[10] Accordingly, for situations where low levels of the protein (e.g., pIII) required for the generation of infectious viral particles renders host cells resistant to viral infection, it may be desirable to make the expression of the protein (e.g., pIII) required for the generation of infectious viral particles to be dependent on the condition that there be a prior viral infection of the host cells. In some embodiments, an *E. coli* phage shock promoter ($P_{psp}$) is used to require prior viral infection. Transcription from $P_{psp}$ is induced by infection with filamentous phage via a pIV-dependent signaling cascade[11] or by overexpression of a plasmid-encoded phage pIV gene.

To produce a system in which protein expression requires both the presence of the small molecule and prior viral infection, provided herein is a drift promoter. The drift promoter is located on a drift plasmid in the host cell. In some embodiments, the drift promoter is produced from a $P_{psp}$ variant with a TetR operator installed at a position to disrupt either PspF or *E. coli* RNA polymerase binding. In some embodiments, the TetR operator is placed adjacent to the +1 transcription initiation site to produce a host cell drift promoter called $P_{psp-tet}$, which is induced only with the combination of phage infection and ATc. In some embodiments, the $P_{psp-tet}$ is placed upstream of the gene encoding the pIII protein. In some embodiments, propagation of the viral vector (e.g., SP) proceeds without activity-dependent gene III expression. In some embodiments, SPs can propagate in a small-molecule-dependent, activity-independent manner using the host cell drft promoter. In some embodiments, the drift promoter is produced from one that is activated upon pspF release after phage infection. In some embodiments, the host cell drift promoter is produced from another promoter such as ones upstream of pal or hyfR.

In some embodiments, provided is a method of tuning the selection stringency in continuous directed evolution methods. For example, to tune the selection stringency, a host cell can use the following plasmids: an activity-dependent AP, such as a $P_{T7}$-gene III AP, in which gene III is controlled by an activity-dependent promoter; and a drift plasmid (DP) with a host cell drift promoter-gene III cassette, such as a $P_{psp-tet}$-gene III. In some embodiments, the AP additionally contains a reporter gene such as a luciferase gene. In some embodiments, the selection stringency is inversely proportional to the concentration of the small molecule used. In some embodiments, low selection stringency conditions are used. For example, saturating amounts of a small molecule inducer (e.g., ATc) allows the $P_{psp-tet}$-gene III cassette in the DP to provide sufficient pIII to maximize phage propagation, regardless of the SP-encoded property (such as activity), thus enabling genetic drift of the SP (low stringency). In some embodiments, an intermediate selection stringency is used. For example, at intermediate concentrations of a small molecule inducer (e.g., ATc), SPs encoding active library members have a replicative advantage over an SP encoding a weakly active/inactive variant by inducing additional pIII expression from an activity-dependent manner. An intermediate concentration is determined by sampling a number of concentrations of the small molecule by using a plasmid the carries the native $P_{tet}$ promoter driving bacterial luciferase. Intermediate concentrations are typically considered those around the inflection point of a sigmoidal graph. In some embodiments, high selection stringency conditions are used. For example, a zero or low amount of a small molecule inducer (e.g., ATc) allows the selection stringency to be determined by the activity-dependent AP with no assistance from the $P_{psp-tet}$-gene III cassette (high stringency).

In some embodiments, the evolution experiments uses a ratio of SPs with active starting genetic libraries to SPs with weakly active/inactive starting genetic libraries of about 1:1, 1:5, 1:10, 1:20, 1:40, 1:60, 1:80, 1:100, 1:120, 1:60, or 1:200. In one embodiment, the ratio of SPs with active to weakly active/inactive starting libraries is 1:100. In some embodiments, phage population is generally followed over time using a detectable label or directly via standard techniques. For example, the phage population can be followed using a combination of restriction endonuclease digests and/or real-time measurements of luminescence monitoring of promoter transcriptional activity (e.g., $P_{T7}$ transcriptional activity), as further described herein. Additional methods are PCR, plaque assays, analysis by gel electrophoresis, or analytical digestion. In some embodiments, an accessory plasmid carrying the gene III and a gene encoding a co-expressed reporter fluorescent protein (such as the luciferase gene, GFP, or other fluorescent protein described herein) under the control of a conditional promoter (such as a $P_{T7}$ or $P_{T3}$) would produce luminescence from the translated luciferase when there is promoter transcriptional activity.

Selection stringency modulation can be used at any point in the continuous evolution process. In some embodiments, selection stringency modulation is used towards the end of the continuous evolution process. In some embodiments, selection stringency modulation is used towards the beginning of the continuous evolution process. In some embodiments, the selection stringency modulation is combined with negative selection.

In an embodiment, provided is a method for modulating the selection stringency during viral-assisted evolution of a gene product, the method comprising: (a) introducing host cells into a lagoon, wherein the host cell comprises a low selection stringency plasmid and a high selection stringency plasmid, wherein the low selection stringency plasmid comprises a viral gene required to package the selection viral vector into an infectious viral particles, wherein at least one gene required to package the selection viral vector into an infectious viral particles is expressed in response to the a concentration of a small molecule, and wherein the high selection stringency plasmid comprises a second copy of the viral gene required to package the selection viral vector into the infectious viral particles, wherein at least one viral gene required to package the selection viral vector into an infectious viral particles is expressed in response to a desired activity property of a gene product encoded by the gene to be evolved or an evolution product thereof; (b) introducing a selection viral vector comprising a gene to be evolved into a flow of host cells through a lagoon, wherein the gene to be evolved produces an active gene product or a weakly active or inactive gene product, wherein the active gene product has an activity that drives the expression of the viral gene required to package the selection viral vector into infectious viral particles in the high selection stringency plasmid and wherein the weakly active or inactive gene product has a relatively lower activity than the activity of the active gene product; and (c) mutating the gene to be evolved within the flow of host cells, wherein the host cells are introduced through the lagoon at a flow rate that is faster than the replication rate of the host cells and slower than the replication rate of the virus thereby permitting replication of the selection viral vector in the lagoon. In an embodiment, the host cells are fed from a chemostat into the lagoon.

In an embodiment, the method further comprising isolating the selection viral vector comprising an evolved product from the flow of cells and determining one or more properties of the evolved product. In one embodiment, the low selection stringency plasmid contains a drift promoter that is activated by a concentration of a small molecule inducer and/or prior viral infection. In one embodiment, the high selection stringency plasmid contains a promoter that is activated by a desired property of a gene product encoded by the gene to be evolved or an evolution product thereof. In yet another embodiment, the low selection stringency plasmid comprises a mutagenesis cassette under the control of a small-molecule inducible promoter. In another embodiment, the low selection stringency plasmid allows a high level of evolutionary drift to occur when the drift promoter is activated in response to a concentration of a small molecule inducer and/or prior viral infection. In one embodiment, the high selection stringency plasmid allows a low level of evolutionary drift to occur when the promoter is activated in response to a desired activity property of a gene product encoded by the gene to be evolved or an evolution product thereof.

In one embodiment, the property of the gene to be evolved originated from a weakly active or inactive starting gene. In one embodiment, the property of the gene to be evolved originated from an active starting gene. In an embodiment, the high selection stringency comprises a T7 promoter. In another embodiment, the low selection stringency comprises a drift promoter that is activated by a small-molecule inducer and/or prior viral infection. In one embodiment, the drift promoter is a Ppsp-tet promoter.

In one embodiment, the method of modulating the selection stringency further comprises the use of negative selection and/or positive selection.

Negative Selection

Selecting solely for activity on a new target substrate without counter-selection against activity on non-target substrates is likely to result in enzymes with broadened, rather than altered, specificity. Negative selection strategies that exert evolutionary pressure against undesired activities, including poor specificity, are useful to avoid or minimize undesired (off-target) activity, and allow the evolution of enzymes with high specificity, by linking undesired activities to the inhibition of viral or phage propagation or the inhibition of viral or phage infection.

Provided herein is a negative selection strategy which inhibits infectious viral production (e.g., phage production) in a manner that is tunable and proportional to the ratio of undesired (off-target) to desired (on-target) activity. The selection is not dependent on the absolute level of the undesired activity. In some embodiments, undesired activity induces expression of a protein that antagonizes the protein product of a viral gene required for the generation of infectious viral particles induced in a positive selection. In one embodiment, undesired activity induces expression of a protein that antagonizes the wild-type pIII protein induced in a positive selection. In some embodiments, undesired activity induces expression of a protein such as the dominant negative variant of the pIV protein, or another specific phage gene such as the pII and pVI proteins. In some embodiments, undesired activity induces expression of a protein that reduces the ability of a viral particle (e.g., phage) to be infectious. For example, a protein that reduces the ability of a viral particle to be infectious is a dominant negative protein. In some embodiments, expression of a dominant negative form of pIII inhibits infectious phage production by blocking the release of phage from the host cell.

Negative selection strategy for PACE in which undesired activities of evolved products are penalized have been described in International Application No. PCT/US2011/066747, filed Dec. 22, 2011, published as WO2012/088381, which is incorporated herein by reference. In some embodiments, this is achieved by causing the undesired activity to interfere with pIII production. For example, expression of an antisense RNA complementary to the gIII RBS and/or start codon is one way of applying negative selection, while expressing a protease (e.g., TEV) and engineering the protease recognition sites into pIII is another. Negative selection is useful, for example, if the desired evolved product is an enzyme with high specificity, for example, a transcription factor or protease with altered, but not broadened, specificity. In some embodiments, negative selection of an undesired activity is achieved by causing the undesired activity to interfere with pIII production, thus inhibiting the propagation of phage genomes encoding gene products with an undesired activity. In some embodiments, expression of a dominant-negative version of pIII or expression of an antisense RNA complementary to the gIII ribosome binding site (RBS) and/or gIII start codon is linked to the presence of an undesired activity. In some embodiments, a nuclease or protease cleavage site, the recognition or cleavage of which is undesired, is inserted into a pIII transcript sequence or a pIII amino acid sequence, respectively. In some embodiments, a transcriptional or translational repressor is used that represses expression of a dominant negative variant of pIII and comprises a protease cleavage site the recognition or cleavage of which is undesired.

In some embodiments, counter-selection against activity on non-target substrates is achieved by linking undesired evolved product activities to the inhibition of phage propagation. For example, in some embodiments, in which a transcription factor is evolved to recognize a specific target sequence, but not an undesired off-target sequence, a negative selection cassette is employed, comprising a nucleic acid sequence encoding a dominant-negative version of pIII (pIII-neg) under the control of a promoter comprising the off-target sequence. If an evolution product recognizes the off-target sequence, the resulting phage particles will incorporate pIII-neg, which results in inhibition of phage infective potency and phage propagation, thus constituting a selective disadvantage for any phage genomes encoding an evolution product exhibiting the undesired, off-target activity, as compared to evolved products not exhibiting such an activity. In some embodiments, a dual selection strategy is applied during a continuous evolution experiment, in which both positive selection and negative selection constructs are present in the host cells. In some such embodiments, the positive and negative selection constructs are situated on the same plasmid, also referred to as a dual selection accessory plasmid. In some such embodiments, the positive and negative selection constructs are situated on two different accessory plasmids within a host cell. The use of two separate accessory plasmids gives the ability to modulate the positive and negative selection aspects independently, thereby yielding, for example, highly selective variants of the gene of interest.

For example, in some embodiments, a dual selection accessory plasmid is employed comprising a positive selection cassette, comprising a pIII-encoding sequence under the control of a promoter comprising a target nucleic acid sequence, and a negative selection cassette, comprising a pIII-neg encoding cassette under the control of a promoter comprising an off-target nucleic acid sequence. In other embodiments, a first accessory plasmid (i.e, a positive selection AP) is employed comprising a positive selection cassette, comprising a pIII-encoding sequence under the control of a promoter comprising a target nucleic acid sequence, and a second accessory plasmid (i.e, a negative selection AP) is employed comprising a negative selection cassette, comprising a pIII-neg encoding cassette under the control of a promoter comprising an off-target nucleic acid sequence. One advantage of using a simultaneous dual selection strategy is that the selection stringency can be fine-tuned based on the activity or expression level of the negative selection construct as compared to the positive selection construct. Another advantage of a dual selection strategy is the selection is not dependent on the presence or the absence of a desired or an undesired activity, but on the ratio of desired and undesired activities, and, thus, the resulting ratio of pIII and pIII-neg that is incorporated into the respective phage particle.

Some aspects of this invention provide or utilize a dominant negative variant of pIII (pIII-neg), previously described in International Application No. PCT/US2011/066747, filed Dec. 22, 2011, published as WO2012/088381, which is incorporated herein by reference. These aspects are based on the discovery that a pIII variant (N-C83) that comprises the two N-terminal domains of pIII and a truncated, termination-incompetent C-terminal domain is not only inactive but is a dominant-negative variant of pIII. The mutated C domain has an internal deletion of 70 amino acids. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. Without wishing to be bound by theory, some aspects of this invention are based in part on the discovery that a pIII-neg variant as provided herein is sufficient to mediate attachment to a phage particle but cannot catalyze the detachment of nascent phage from the host cell membrane during phage particle synthesis. Accordingly, such pIII-neg variants are useful for devising a negative selection strategy in the context of PACE, for example, by providing an expression construct comprising a nucleic acid sequence encoding a pIII-neg variant under the control of, for example, a promoter comprising a recognition motif, the recognition of which is undesired. In other embodiments, the undesired substrate or undirected substrate recognition is tethered upstream of a dominant negative mutant such as pIII-neg.

In some embodiments, multiple undesired activities, e.g., off-target DNA-binding activities, of a gene product to be evolved are selected against using the negative selection strategies provided herein. A negative selection against multiple off-target DNA-binding activities can be achieved in different ways. For example, a selection phage may be propagated initially in host cells carrying an accessory plasmid linking activity towards a first undesired off-target site to negative selection, and subsequently in host cells carrying different accessory plasmids creating negative selective pressure against different off-target sites. In addition to such sequential approaches, this disclosure also provides strategies featuring a combination of different negative selection constructs to create negative selective pressure against multiple off-target activities. For example, in some embodiments, a selection phage is propagated during a PACE experiment in host cells comprising two or more accessory plasmids, each one containing a negative selection construct linking DNA-binding to a different undesired off-target site to negative selection, thus resulting in selective pressure against two or more different off-target sites. In some embodiments, a selection phage is propagated in a population of host cells in which different host cells carry different accessory plasmids, e.g., linking activity towards different undesired off-target sites to negative selection. While each host cell in such a population will only create negative selective pressure against a single off-target activity, the propagation in a population of host cells carrying different accessory plasmids results in a selective pressure against multiple off-target activities.

In other embodiments, pIII-neg is used in a positive selection strategy, for example, by providing an expression construct in which a pIII-neg encoding sequence is controlled by a promoter comprising a nuclease target site or a repressor recognition site, the recognition of either one of which is desired.

The methods herein can also use positive and negative selection strategies which can be used alternately with one another or used simultaneously. The positive and negative selection schemes would be identical for a PACE application of interest, with the only difference being the positive selection results in the synthesis of pIII and the negative selection results in the synthesis of pIII-neg. For example, the expression of one or the other is dependent upon the selection scheme.

Positive and negative selection strategies can further be designed to link non-DNA directed activities to phage propagation efficiency. For example, protease activity towards a desired target protease cleavage site can be linked to pIII expression by devising a repressor of gene expression that can be inactivated by a protease recognizing the target site. In some embodiments, pIII expression is driven by a promoter comprising a binding site for such a repressor. Suitable transcriptional repressors are known to those in the art, and one exemplary repressor is the lambda repressor protein that efficiently represses the lambda promoter pR and can be modified to include a desired protease cleavage site (see, e.g., Sices, H. J.; Kristie, T. M., A genetic screen for the isolation and characterization of site-specific proteases. *Proc Natl Acad Sci USA* 1998, 95 (6), 2828-33; and Sices, H. J.; Leusink, M. D.; Pacheco, A.; Kristie, T. M., Rapid genetic selection of inhibitor-resistant protease mutants: clinically relevant and novel mutants of the HIV protease. *AIDS Res Hum Retroviruses* 2001, 17 (13), 1249-55, the entire contents of each of which are incorporated herein by reference). The lambda repressor (cI) contains an N-terminal DNA binding domain and a C-terminal dimerization domain. These two domains are connected by a flexible linker. Efficient transcriptional repression requires the dimerization of cI, and, thus, cleavage of the linker connecting dimerization and binding domains results in abolishing the repressor activity of cI.

Some embodiments provide a pIII expression construct that comprises a pR promoter (containing cI binding sites) driving expression of pIII. When expressed together with a modified cI comprising a desired protease cleavage site in the linker sequence connecting dimerization and binding domains, the cI molecules will repress pIII transcription in the absence of the desired protease activity, and this repression will be abolished in the presence of such activity, thus providing a linkage between protease cleavage activity and an increase in pIII expression that is useful for positive PACE protease selection. Some embodiments provide a negative selection strategy against undesired protease activity in PACE evolution products. In some embodiments, the negative selection is conferred by an expression cassette comprising a pIII-neg encoding nucleic acid under the control of a cI-repressed promoter. When co-expressed with a cI repressor protein comprising an undesired protease cleavage site, expression of pIII-neg will occur in a cell harboring phage expressing a protease exhibiting protease activity towards the undesired target site, thus negatively selecting against phage encoding such undesired evolved products. A dual selection for protease target specificity can be achieved by co-expressing cI-repressible pIII and pIII-neg encoding expression constructs with orthogonal cI variants recognizing different DNA target sequences, and thus allowing for simultaneous expression without interfering with each other. Orthogonal cI variants in both dimerization specificity and DNA-binding specificity are known to those of skill in the art (see, e.g., Wharton, R. P.; Ptashne, M., Changing the binding specificity of a repressor by redesigning an alphahelix. *Nature* 1985, 316 (6029), 601-5; and Wharton, R. P.; Ptashne, M., A new-specificity mutant of 434 repressor that defines an amino acid-base pair contact. *Nature* 1987, 326 (6116), 888-91, the entire contents of each of which are incorporated herein by reference).

Provided herein is negative selection of a biomolecule with an undesired activity in combination with positive selection of a biomolecule with desired activity, wherein enrichment of the biomolecule with a desired activity is controlled by, for example, the concentration of a small molecule. In some embodiments, a host cell contains both a positive selection AP and a negative selection AP, wherein the positive selection AP contains a viral gene required for the generation of infectious viral particles (e.g., phage gene such as gene III) and wherein the negative selection AP contains a dominant negative mutant of the viral gene (e.g., gene III-neg). In some embodiments, the viral gene required for the generation of infectious viral particles contained in the positive selection AP is under the control of a first small molecule inducible promoter and the dominant negative mutant of the viral gene contained in the negative selection AP is under the control of a second small molecule inducible promoter, wherein a first small molecule is used to induce the first small molecule inducible promoter, and wherein a second small molecule is used to induce the second small molecule inducible promoter. In one embodiment, the first small molecule inducible promoter is a TetA promoter ($P_{tet}$). In one embodiment, the small molecule used to induce transcription of genes under the control of $P_{tet}$ is ATc. In one embodiment, the second small molecule inducible promoter is a promoter of the lac operon ($P_{lac}$). In one embodiment, the small molecule used to induce transcription of genes under the $P_{lac}$ is isopropyl β-D-1-thiogalactopyranoside (IPTG). In some embodiments, the negative selection AP containing a dominant negative mutant of a phage gene is under the control of a riboswitch. Non-limiting examples of riboswitches include, for example, the lysine riboswitch from *Bacillus subtilis*, the glycine riboswitch from *Bacillus subtilis*, the adenine riboswitch from *Bacillus subtilis* or the TPP tandem riboswitch from *Bacillus anthracia*. In addition to the foregoing naturally occurring riboswitch elements, synthetic riboswitch elements can also be used, such as, for example, the theophylline riboswitch, the biotin riboswitch or the Tet riboswitch. In some embodiments, the riboswitch is activated by theophylline. In some embodiments, the rate of enrichment of the biomolecule with desired activity is dependent on the concentration of the small molecule used to control translation of the dominant negative protein. In some embodiments, the phage gene is gene III. In some embodiments, the dominate negative mutant of a phage gene is a gene encoding a dominant negative pIII protein. In some embodiments, the dominant negative pIII protein contains a mutant C domain. In some embodiments, the dominant negative pIII protein is the N-C83 variant, wherein the C domain of the pIII protein has an internal deletion of a certain number of 70 amino acids.

In some embodiments, the viral gene required for the generation of infectious viral particles contained in the positive selection AP is under the control of a promoter comprising a desired DNA binding site for the gene product. In some embodiments, following initial negative selection, high-stringency host cells are used to further enhance the desired activity, wherein the positive selection construct has been modified to reduce the translation of pIII from the AP and wherein the negative selection construct has been modified to enhance the translation of pIII-neg from the $AP_{neg}$. For example, the RBS on the positive selection AP is weakened; a strong RBS replaces the riboswitch on the negative selection AP; or the negative selection AP has been modified to be a high copy plasmid.

In negative and positive selection methods herein, the wild-type pIII and pIII-neg compete for incorporation into a progeny phage particle, thus making the potency of inhibition sensitive to the ratio of the desired or undesired activities.

The ratio of the SPs containing desired and undesired activity can be varied in the evolution experiments. In some embodiments, the ratio of a SP containing a gene encoding a biomolecule with desired activity to a SP containing a gene encoding a biomolecule with undesired activity is about 1:1, 1:100, $1:10^3$, $1:10^4$, $1:10^5$, $1:10^6$, $1:10^9$ or $1:10^{10}$. In one embodiment, the ratio of desired SP to undesired SP is about $1:10^6$.

In some embodiments, the number of hours of PACE with negative selection to evolve a biomolecule with desired activity is about 3 hours, 4 hours, 5 hours, 6 hours, 8 hours, 10 hours, 15 hours, 20 hours, 30 hours, or 40 hours. In some embodiments, the number of hours of PACE with negative selection to evolve a biomolecule with desired activity is about 4 to about 8 hours.

Negative selection can be used at any point in the continuous evolution process. In some embodiments, negative selection is used towards the end of the continuous evolution process. In some embodiments, negative selection is used towards the beginning of the continuous evolution process. In some embodiments, the negative selection is combined with selection stringency modulations.

In an embodiment, provided is a method of using negative selection during viral-assisted evolution of a gene product, the method comprising: (a) introducing host cells into a lagoon, wherein the host cell comprises a negative selection gene and a dominant negative mutant gene of a phage gene that decreases or abolishes packaging of the selection viral vector into infectious viral particles, wherein the dominant negative gene is expressed in response to an undesired activity of the gene to be evolved or an evolution product thereof or in response to a concentration of a small molecule inducer; (b) introducing a mixture of selection viral vectors into a flow of host cells through a lagoon, wherein one type of selection viral vector comprises a negative selection gene comprising an undesired gene or gene encoding an undesired property of the gene to be evolved and wherein another type of selection viral vector comprises a positive selection gene comprising a desired gene or gene encoding a desired property of the gene to be evolved; and (c) mutating the gene to be evolved within the flow of host cells, wherein the host cells are introduced through the lagoon at a flow rate that is faster than the replication rate of the host cells and slower than the replication rate of the virus thereby permitting replication of the selection viral vector in the lagoon. In one embodiment, the negative selection gene and dominant negative mutant gene is found on an negative selection accessory plasmid. In an embodiment, the negative selection accessory plasmid further comprises a sequence encoding for a riboswitch. In another embodiment, the transcribed riboswitch is activated by a small-molecule. In an embodiment, the small-molecule is theophylline.

In one embodiment, the negative selection accessory plasmid comprises a high-copy origin of replication. In an embodiment, the negative selection accessory plasmid comprises a modulation of the ribosome-binding site driving translation of the dominant negative mutant gene, wherein modulation is weakening or strengthening. In another embodiment, the negative selection accessory plasmid further comprises a gene encoding for a detectable label. In an embodiment, the detectable label is a fluorescent protein. In a specific embodiment, the fluorescent protein is luciferase.

In another embodiment, the dominant negative mutant gene is expressed under the control of a theophylline-activated riboswitch. In an embodiment, the negative selection gene is a promoter. In one embodiment, the negative selection promoter is a T3 or T7 promoter.

In one embodiment, the method of negative selection further comprises a method of positive selection, the method comprising a positive selection gene comprising a gene that decreases or abolishes packaging of the selection phagemids into infectious phage particles. In an embodiment, the positive selection gene is found on a positive selection accessory plasmid. In one embodiment, the positive selection accessory plasmid comprises modulation of the ribosome binding site, wherein modulation is weakening or strengthening. In another embodiment, the positive selection accessory plasmid further comprises a sequence encoding for a riboswitch. In one embodiment, the transcribed riboswitch is activated by a small-molecule. In an embodiment, the small-molecule is theophylline.

In one embodiment, the positive selection accessory plasmid further comprises a gene encoding for a detectable label. In another embodiment, the detectable label is a fluorescent protein. In one embodiment, the fluorescent protein is luciferase.

In an embodiment, the positive selection accessary plasmid and negative selection plasmid are on the same or different plasmids. In an embodiment, the positive selection gene is a promoter. In another embodiment, the positive selection promoter is a T7 or T3 promoter.

In one embodiment, the host cells further comprises a mutagenesis cassette located on a mutagenesis plasmid and is under control of a small-molecule inducible promoter. In one embodiment, the host cells introduced into the lagoon are from a chemostat.

In an embodiment, wherein the small molecule inducer that drives expression of a positive selection gene is different from the small molecule inducer that drives expression of a dominant negative mutant gene. In an embodiment, the selection viral vector comprising a negative selection gene and the selection viral vector comprising a positive selection gene is found in a ratio of about 1:1 to about $10^9$:1.

In one embodiment, the dominant negative mutant is found on an accessory plasmid. In an embodiment, the positive selection gene is found on the same or different accessory plasmid as the accessory plasmid comprising the dominant negative mutant. In one embodiment, the dominant negative mutant gene encodes a dominant negative mutant protein that antagonizes the gene product of a phage gene that decreases or abolishes packaging of the selection phagemids into infectious phage particles. In one embodiment, the dominant negative mutant gene is a dominant negative mutant of a gene encoding a dominant negative pIII protein. In one embodiment, the dominant negative pIII protein comprises a mutant C-domain. In one embodiment, the dominant negative pIII protein comprises a deletion of amino acids 1-70 from the C-domain. In an embodiment, the dominant negative pIII protein is the N-C83 variant. In another embodiment, the positive selection gene is a gene encoding a pIII protein.

Methods and Vector Systems for Modulation of Selection Stringency and Negative Selection Provided herein is a method of rapidly evolving biomolecules, such as enzymes, polymerases, and transcription factors, with altered properties, such as altered substrate specificity or activity, using the tunable selection stringency and negative selection methods described herein. In some embodiments, selection stringency strategies are used to generate an initial evolved product prior to using negative selection methods to generate enhanced evolved product. Provided herein are also vector systems which combine the selection stringency modulation and negative selection strategies described herein.

In one embodiment, provided is a method of modulating the selection stringency and using negative selection and/or positive selection during viral-assisted evolution of a gene product, the method comprising the foregoing methods described. In an embodiment, modulating the selection stringency and using negative selection and/or positive are used in various stages of a continuous evolution experiment.

In an embodiment, the gene of interest to be evolved encodes a DNA-binding gene product. In one embodiment, the DNA-binding gene product is an RNA polymerase. In a specific embodiment, the RNA polymerase is a T7 RNA polymerase. In an embodiment, the T7 RNA polymerase has been evolved to be specific for the T3 promoter. In an embodiment, expression of the gene required to package the selection phagemid into infectious particles is driven by a promoter comprising a desired DNA binding site for the gene product. In one embodiment, expression of the dominant negative mutant of the phage gene that decreases or abolishes packaging of the selection phagemids into infectious phage particles is driven by a promoter comprising an undesired DNA binding site for the gene product. In an embodiment, the host cells are introduced into lagoons from a chemostat. In one embodiment, the host cells are prokaryotic cells amenable to phage infection, replication, and production. In one embodiment, the host cell is bacterial. In another embodiment, the host cell is *E. coli*. In another embodiment, a gene that is required to package the selection viral vector into infectious viral particles is a gene that encodes for the pIII protein. In one embodiment, the gene that encodes for the pIII protein is gene III or a gene that is at least about 50%, 60%, 70%, 80%, 90%, or 99% homologous to gene III. In another embodiment, the selection viral vector comprises all viral genes required for the generation of viral particles, except for a full-length gene that is required to package the selection viral vector into infectious viral particles. In one embodiment, the selection viral vector is a selection phage or phagemid. In another embodiment, the selection viral vector is a filamentous phage. In one embodiment, the selection viral vector is M13 phage. In another embodiment, the undesired DNA binding site is PT7 or PT3. In an embodiment, the desired DNA binding site is PT7 or PT3.

In some embodiments, the use of selection stringency modulation methods allows the continuous directed evolution of a first evolved product containing a novel property evolved from a biomolecule with weakly active/inactive starting activity. In some embodiments, the use of intermediate substrates in the evolution is not needed. In one embodiment, a low selection stringency is used. In one embodiment, a first population of host cells carries a vector system containing a combination of a $P_{T3}$-gene III AP and a DP containing the $P_{psp-tet}$ gene III cassette and the SP-T7$_{WT}$ carries a biomolecule with inactive starting activity (i.e., T7$_{WT}$ RNAP) because it has negligible starting activity on $P_{T3}$. In one embodiment, the AP contains a reporter gene such as a luciferase gene. In one embodiment, the first evolved product is a T7 RNAP that recognizes $P_{T3}$. In some embodiments, an intermediate substrate such as a hybrid T7/T3 promoter is not needed in the evolution of toward $P_{T3}$ selection.

In some embodiments, the subsequent use of negative selection methods allows the evolution of a second evolved product containing properties that is altered or enhanced from the initial properties found in the first evolved product. In one embodiment, a second population of host cells carries the same $P_{T3}$-gene III AP, a MP without the drift cassette, and a $P_{T7}$-gene III-neg AP$_{neg}$, wherein pIII-neg expression is driven by $P_{T7}$ transcription and controlled by a theophylline-dependent riboswitch. In one embodiment, the AP contains a reporter gene such as a luciferase gene. Negative selection is activated by addition of theophylline to the lagoon. The result is a second evolved product that demonstrates specificity improvements for $P_{T3}$ and decreased specificity for $P_{T7}$.

In some embodiments, the property of the second evolved product is further altered or enhanced by increasing the stringency of the negative selection. In some embodiments, the increased stringency is enhanced by increasing the ratio of a dominant negative mutant to the positive mutant counterpart. In some embodiments, the stringency of negative selection can be controlled by varying the strength of the RBS and the AP copy number. In some embodiments, the stringency of negative selection is increased using high-stringency host cells containing the same MP without the drift cassette, a $P_{T3}$-gene III AP with a reduced RBS, and a $P_{T7}$-gene III-neg APneg containing a high-copy pUC origin and a strong RBS. In one embodiment, the AP contains a reporter gene such as a luciferase gene. The foregoing exemplary modifications increase the stringency of negative selection by increasing the ratio of pIII-neg to pIII expressed in the host cell.

Evolved Product

Some aspects of this invention provide evolved products (or evolution products) of continuous evolution processes described herein, wherein the evolved products contain evolved properties. In some embodiments, the evolved product has increased or enhanced properties (e.g., activity, specificity, stability, enantioselectivity) compared with the original product of the gene of interest. In some embodiments, the evolved product has decreased or reduced properties (e.g., activity, specificity, stability, enantioselectivity) compared with the original product of the gene of interest. Non-limiting examples of an evolved product include modified T7 RNAP, modified RNA ligase ribozymes, beta lactamase, modified zinc-finger binding domains, modified zinc-finger targeted recombinases, and modified Tn3-family serine recombinase enzymes, modified TEV protease, or modified single-chain variable fragments (scFvs).

In some embodiments, the evolved products have altered substrate specificity. In some embodiments, the evolved products have altered activity. In some embodiments, the evolved product resulting from a continuous directed evolution experiment exhibits at least a 2-fold, at least 5-fold, at least 10-fold, at least 20-fold, at least 30-fold, at least 40-fold, at least 50-fold, at least 60-fold, at least 80-fold, at least 100-fold, or at least 120-fold greater activity than that of the starting biomolecule used in to originally generate the evolved product. In some embodiments, the evolved product resulting from a continuous directed evolution experiment exhibits at least 50-fold, at least 100-fold, at least 500-fold, at least 1000-fold, at least 5000-fold, at least 10,000-fold, at least 12,000-fold, or at least 15,000-fold change in specificity for its non-native target.

For example, some embodiments provide a modified T7 RNA polymerase (T7 RNAP) having an altered substrate specificity and/or an increased transcriptional activity as compared to wild-type T7 RNAP. In some embodiments, the evolved product is a modified T7 RNAP that initiates transcription from a T3 promoter. In some embodiments, the evolved product is a modified T7 RNAP that initiates transcription from an SP6 promoter. In some embodiments, the modified T7 RNAP exhibits an at least 2-fold, at least 5-fold, at least 10-fold, at least 20-fold, at least 30-fold, at least 40-fold, or at least 50-fold greater transcription rate from its native T7 promoter than the wild-type enzyme. In some embodiments, the modified T7 RNAP exhibits an at least 2-fold, at least 5-fold, at least 10-fold, at least 20-fold, at least 30-fold, at least 40-fold, at least 50-fold, at least 60-fold, at least 80-fold, at least 100-fold, or at least 120-fold greater transcription rate from a non-native T7 RNAP promoter than the wild-type enzyme. In some embodiments, the non-native T7 RNAP promoter is a SP6 promoter. In some embodiments, the non-native T7 RNAP promoter is a T3 promoter. In some embodiments, the T7 RNA polymerase is at least about 1.5-fold, 2-fold, 5-fold, 10-fold, 20-fold, 50-fold, 80-fold, 100-fold, 500-fold, 800-fold, 1000-fold, 3,000-fold, 5,000-fold, 8,000-fold, 10,000-fold, 12,000-fold, or 15,000-fold more specific for the $P_{T3}$ over the $P_{T7}$. In some embodiments, the T7 RNA polymerase is at least about 1.5-fold to 10-fold, 10-fold to 50-fold, 50-fold to 80-fold, 80-fold to 100-fold, 100-fold to 300-fold, 300-fold to 500-fold, 500-fold to 800-fold, 1000-fold to 3,000-fold, 3,000-fold to 5,000-fold, 5,000-fold to 8,000-fold, 8,000-fold to 10,000-fold, 10,000-fold to 12,000-fold, or 12,000-fold to 15,000-fold more specific for the $P_{T3}$ over the $P_{T7}$.

In some embodiments, the evolved product from a is a $P_{T3}$-specific RNAP that exhibits a net of at least 1000-fold, at least 5,000-fold, at least 10,000-fold, or at least 15,000-fold-fold change in specificity for $P_{T3}$.

In some embodiments, the evolved product is generated using the methods described herein in at least about 1 hour, 2 hours, 4 hours, 6 hours, 8 hours, 10 hours, 12 hours, 14 hours, 16 hours, 18 hours, 20 hours, 24 hours, 30 hours, 36 hours, 40 hours, 48 hours, 60 hours, 72 hours, or 100 hours. In some embodiments the evolved product is generated in about 2-12 hours, 12-24 hours, 24-48 hours, 48-60 hours, 60-72 hours, or 72-100 hours.

In some embodiments, the evolved product is a T7 RNAP that evolved the ability to accept the T3 promoter over the T7 promoter. In some embodiments, such evolved T7 RNAP has at least 1, 2, 3, 4, 5, or 6 highly conserved mutations including those selected from R96L, K98R, E207K, E222K, N748D, and P759S/L. In some embodiments, the evolved T7 RNAP is a N748D mutant; a E222K/N748D mutant; a E207K/E222K/N748D mutant; a R96L/K98R/E207K/E222K/N748D mutant; a R96L/K98R/E207K/E222K/N748D/P759S mutant; or a R96L/K98R/E207K/E222K/N748D/P759L mutant. The properties of an evolved product can be monitored over time using a number of methods. For example, the phage population can be followed using a combination of restriction endonuclease digests and/or real-time measurements of luminescence monitoring of promoter transcriptional activity (e.g., $P_{T7}$ transcriptional activity), as further described herein. Promoter transcriptional activity can be monitored by linking the activity to the expression of a reporter gene or protein fluorescence. In some embodiments, an accessory plasmid carrying the gene III and a gene encoding a fluorescent protein (such as the luciferase gene, GFP, or other fluorescent protein described herein) are both under the control of a conditional promoter (such as a $P_{T7}$ or $P_{T3}$) and the expression of a fluorescent protein produces luminescence from the expressed luciferase when there is promoter transcriptional activity.

PACE Using Modulation of Selection Stringency and Negative Selection

Provided herein a method of using PACE with modulation of the selection stringency followed by the combination of negative and positive selection strategies to evolve a T7 RNAP with activity and specificity for a T3 promoter.

In an embodiment, provided is a method for modulating the selection stringency during phage-assisted evolution of a gene product, the method comprising: (a) introducing E. coli host cells from a chemostat into a lagoon, wherein the host cell comprises a low selection stringency plasmid and a high selection stringency plasmid, wherein the low selection stringency plasmid comprises gene III wherein gene III is expressed in response to the a concentration of anhydrotetracycline, and wherein the high selection stringency plasmid comprises a second copy of gene III, wherein gene III is expressed in response to T3 RNAP activity; (b) introducing a selection phage comprising a gene encoding T7 RNAP to be evolved into a flow of host cells through a lagoon; and (c) mutating the gene encoding T7 RNAP within the flow of host cells, wherein the host cells are introduced through the lagoon at a flow rate that is faster than the replication rate of the host cells and slower than the replication rate of the virus thereby permitting replication of the selection viral vector in the lagoon.

In one embodiment, the low selection stringency plasmid contains a Ppsp-tet drift promoter that is activated by a concentration of anhydrotetracycline and prior viral infection. In one embodiment, the high selection stringency plasmid contains a T3 promoter that is activated by a T3 RNAP or an T7 RNAP modified to have activity for a T3 promoter. In yet another embodiment, the low selection stringency plasmid comprises a mutagenesis cassette under the control of an arabinose inducible promoter. In another embodiment, the low selection stringency plasmid allows a high level of evolutionary drift to occur when the Ppsp-tet drift promoter is activated in response to a concentration anhydrotetracycline and prior viral infection. In one embodiment, the high selection stringency plasmid allows a low level of evolutionary drift to occur when the T3 promoter is activated in response to a T7 RNAP modified to have activity for a T3 promoter.

In one embodiment, the method of modulating the selection stringency further comprises the use of negative selection and/or positive selection.

In an embodiment, provided is a method of using negative selection during phage-assisted evolution of a gene product, the method comprising: (a) introducing E. coli host cells from a chemostat into a lagoon, wherein the cell comprises a negative selection gene and a dominant negative mutant gene encoding a pIIIneg protein, wherein the transcription of the dominant negative gene is driven by a PT7 promoter in response to an undesired T7 RNAP activity of the gene to be evolved or an evolution product thereof and the translation of the dominant negative mutant gene encoding a pIII-neg protein is under the control of a theophylline-inducible riboswitch, which is activated by a concentration of theophylline; (b) introducing a mixture of selection phage into a flow of host cells through a lagoon, wherein one type of selection phage comprises a PT7 as the negative selection gene comprising an undesired T7 RNAP property of the T7 RNAP gene to be evolved and wherein another type of selection phage comprises a PT3 as the positive selection gene comprising a desired T3 RNAP property of the T7 RNAP gene to be evolved; and (c) mutating the T7 RNAP gene to be evolved within the flow of host cells, wherein the host cells are introduced through the lagoon at a flow rate that is faster than the replication rate of the host cells and slower than the replication rate of the phage thereby permitting replication of the selection phage in the lagoon. In one embodiment, the PT7 negative selection gene and gene III-neg is found on an negative selection accessory plasmid. In an embodiment, the negative selection accessory plasmid further comprises a sequence encoding for a riboswitch that is activated by a concentration of theophylline. In one embodiment, the host cells further comprises a mutagenesis cassette located on a mutagenesis plasmid and is under control of an arabinose-inducible promoter. In one embodiment, the pIII-neg protein is the N-C83 variant.

In one embodiment, the method of negative selection further comprises a method of positive selection, the method comprising a positive selection accessory plasmid comprising a gene that encodes for the pIII protein and a gene encoding for luciferase, wherein the two are driven by the T3 promoter. In an embodiment, the positive selection plasmid is different from the negative selection plasmid.

In one embodiment, a new batch of host cell is subsequently fed into the lagoon from another chemostat, wherein the host cells comprise a negative selection accessory plasmid with a relatively stronger ribosome binding site and an increased origin copy number and a positive selection accessory plasmid comprising a reduced ribosome biding site PT3-gene III. In an embodiment, the positive selection accessory plasmid further comprises a gene encoding for luciferase.

Apparatus for Continued Evolution

Apparatuses for continued evolution have been previously described. Provided herein is an apparatus comprising a chemostat. A chemostat comprises a cell culture vessel in which the population of fresh host cells is situated in liquid suspension culture. A constant nutrient flow is provided into the chemostat. Unlike a turbidostat, the turbidity in a chemostat does not require monitoring. Like a turbidostat in previously described PACE apparatuses, the chemostat also comprises an outflow that is connected to an inflow of the lagoon, allowing the introduction of fresh cells from the chemostat into the lagoon.

In some embodiments, the media for the chemostat comprises a custom Davis rich media formulation prepared from anhydrous $K_2HPO_4$ (140 g), $KH_2PO_4$ (40 g), $(NH_4)_2SO_4$ (20 g), NaCl (58 g), casamino acids (100 g), Tween-80 (20 mL), L-cysteine (1 g), L-tryptophan (0.5 g), adenine (0.5 g), guanine (0.5 g), cytosine (0.5 g), uracil (0.5 g), CaCl2 (0.5 µM final). The media is allowed to cool overnight, and supplemented with a 500 mL filter-sterilized solution of MilliQ water containing: $NaHCO_3$ (16.8 g), glucose (90 g), sodium citrate (10 g), $MgSO_4$ (1 g), $FeSO_4$ (56 mg), thiamine (134 mg), calcium pantothenate (94 mg), para-aminobenzoic acid (54 mg), para-hydroxybenzoic acid (54 mg), 2,3-dihydroxybenzoic acid (62 mg), $(NH_4)_6Mo_7$ (3 nM final), $H_3BO_3$ (400 nM final), $CoCl_2$ (30 nM), $CuSO_4$ (10 nM final), $MnCl_2$ (80 nM final), and $ZnSO_4$ (10 nM final). In an embodiment, cultures are supplemented with the appropriate antibiotics such as carbenicillin, spectinomycin, chloramphenicol, streptomycin, and/or tetracycline, depending on the antibiotic resistant gene found on the accessory plasmids in the host cells. In one embodiment, the growth of the host cells is equilibrated overnight at a flow rate of about 100, 200, 300, 400, 500, or 800 mL/h. In one embodiment, the growth of the host cells is equilibrated overnight at a flow rate of 400 mL/h. In an embodiment, the chemostat volume is about 100 mL, 150 mL, 200 mL, 250 mL, 300 mL, 350 mL, 400 mL, 450 mL or 500 mL. In an embodiment, the chemostat volume is about 250 mL.

Host Cells

Some aspects of this invention relate to host cells for continuous evolution processes as described herein. In some embodiments, a host cell is provided that comprises at least one viral gene encoding a protein required for the generation of infectious viral particles under the control of a conditional promoter. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cells comprise the gene required for the generation of infectious viral particles under the control of a conditional promoter inserted into their genome, or as a cosmid, phagemid, or an artificial chromosome. In some embodiments, the host cell is a bacterial cell, for example, a bacterial cell amenable to M13 infection, such as certain E. coli cells. For M13 PACE, the host E. coli cells need to express the F-factor, for example, from an F' plasmid. Suitable F' E. coli cell lines and strains are known to those of skill in the art, and include, for example, the F'proA+B+A (lacIZY) zzf::Tn10 (TetR)/endA1 recA1 galE15 galK16 nupG rpsL ΔlacIZYA araD139 Δ(ara,leu)7697 mcrA Δ(mrr-hsdRMS-mcrBC) proBA::pir116 λ− cells described herein.

In some embodiments, the host cell provided further comprises an expression construct comprising a gene encoding a mutagenesis-inducing protein, for example, a mutagenesis plasmid comprising a pBAD promoter, as described elsewhere herein.

Kits

Some aspects of this invention provide kits for continuous evolution as described herein. In some embodiments, the kit comprise reagents, vectors, cells, software, systems, and/or apparatuses for carrying out the methods provided herein. For example, in some embodiments, a kit for controlling the selection stringency in a continuous directed evolution in a bacterial system is provided that includes a selection phage or phagemid; a drift plasmid; an accessory plasmid; optionally, a mutagenesis plasmid and/or a mutagen; and/or a host cell capable of producing infectious phage and amenable to phage infection. In some embodiments, a kit is provided that comprises a two-plasmid PACE vector system, as described in more detail elsewhere herein, for example, comprising a selection phage, a drift plasmid, an accessory plasmid, optionally, a mutagenesis plasmid, but no helper phage. In some embodiments, the kit further contains negative and/or positive selection constructs and optionally, a mutagenesis plasmid and/or a mutagen. In some embodiments, the kit optionally contains small molecule inducers. The kit typically also includes instructions for its use.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1: Evolution of RNA Polymerase Variants

Methods

Bacterial strains. All DNA cloning was performed with Mach1 cells (Invitrogen) or NEB Turbo cells (New England Biolabs). All discrete infection assays, plaque assays and PACE experiments were performed with E. coli S1030. This strain was derived from E. coli S1091 and was modified using the Lambda Red method[23] as follows: 1) scarless mutation to rpoZ to introduce a frameshift mutation to enable n-hybrid schemes;[24] 2) integration of lacI and tetR overexpression cassettes onto the F plasmid to enable small-molecule regulated transcription of various genes; 3) integration of luxCDE onto the F plasmid for the production of decanal to facilitate luciferase monitoring experiments;[25] 4) deletion of flu, pgaC, and csgABCDEFG to dramatically reduce biofilm formation in chemostat PACE experiments;[26-28] and 5) mutation of the chromosomal, low-affinity high-capacity AraE promoter to a constitutive promoter for titratable arabinose induction of the PBAD promoter on the mutagenesis plasmid.[29] The complete genotype of the resulting strain is F'proA+B+Δ(lacIZY) zzf::Tn10 (TetR) lacIQ1 PN25-tetR luxCDE/endA1 recA1 galE15 galK16 nupG rpsL (StrR) ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ-.

Plasmids. A list of plasmids used in these examples are provided in Table 1.

TABLE 1

| Name | Class | Antibiotic Resistance | Origin of Replication | Promoter | Gene |
| --- | --- | --- | --- | --- | --- |
| pJC148i2 | AP | Carb | SC101 | $P_{tet}$ | gIII-luxAB |
| pJC156a2 | AP-neg | Spect | colEI | $P_{lac}$ | C-domain-Venus |
| pJC156c2 | AP-neg | Spect | colEI | $P_{lac}$ | C83-Venus |
| pJC156j2 | AP-neg | Spect | colEI | $P_{lac}$ | N1-N2-C83-Venus |
| pJC156m2 | AP-neg | Spect | colEI | $P_{lac}$ | N2-C83-Venus |
| pJC156o2 | AP-neg | Spect | colEI | $P_{lac}$ | N1*-N2-C83-Venus |

TABLE 1-continued

| Name | Class | Antibiotic Resistance | Origin of Replication | Promoter | Gene |
|---|---|---|---|---|---|
| pJC173b | AP | Carb | SC101 | $P_{T7}$ | gIII-luxAB |
| pJC173c | AP | Carb | SC101 | $P_{T7}$ | 6xHisTag-gIII-luxAB |
| pJC173e4 | AP | Carb | SC101 | $P_{T7}$ | luxAB |
| pJC173f-R5 | AP | Spect | colEI | $P_{T7}$ | TheoRibo-6xHisTag-gIII-Venus |
| pJC173g-SD8 | AP-neg | Spect | pUC | $P_{T7}$ | N1*-N2-C83-Venus (strong RBS) |
| pJC174c-R5 | AP | Spect | colEI | $P_{T3}$ | TheoRibo-6xHisTag-gIII-Venus |
| pJC174e4 | AP | Carb | SC101 | $P_{T3}$ | luxAB |
| pJC174f | AP | Carb | SC101 | $P_{T3}$ | 6xHisTag-gIII-luxAB |
| pJC174k | AP | Carb | SC101 | $P_{T3}$ | 6xHisTag-gIII-luxAB (weak RBS) |
| pJC175e | AP | Carb | SC101 | $P_{psp}$ | gIII-luxAB |
| pJC175g | AP | Carb | SC101 | $P_{psp-tetO}$ | gIII-luxAB |
| pJC175h | AP | Carb | SC101 | $P_{psp-tet}$ | gIII-luxAB |
| pJC175k | AP | Carb | SC101 | $P_{psp-tetO3}$ | gIII-luxAB |
| pJC175m | AP | Carb | SC101 | $P_{psp-tetO5}$ | gIII-luxAB |
| pJC175n | AP | Carb | SC101 | $P_{psp-tetO6}$ | gIII-luxAB |
| pJC184 | MP | Chlor | CloDF13 | $P_{BAD}$ | dnaQ926-umuD'-umuC-recA730 |
| pJC184c-rrnB | AP | Chlor | CloDF13 | $P_{psp}$ | gIII |
| pJC184d5 | DP | Chlor | CloDF13 | $P_{BAD}/P_{psp-tet}$ | dnaQ926-umuD'-umuC-recA730/gIII |
| pJC184d-Spect | AP | Chlor | CloDF13 | $P_{psp-tet}$ | gIII |
| SP-T7$_{WT}$ | SP | Kan | fl | $P_{gIII}$ | wt T7 RNAP |
| SP-T7$_{SP}$ | SP | Kan | fl | $P_{gIII}$ | T7 RNAP mutant L2-48.3 |
| SP-T7$_{Pr}$ | SP | Kan | fl | $P_{gIII}$ | T7 RNAP mutant L1-192.2 |

Chemostat and growth media. Compared to host cell cultures maintained at constant turbidity (turbidostats),[1] host cell cultures maintained at a constant nutrient flow rate (chemostats) are simpler to set up and do not require constant turbidity monitoring. We found that chemostats using E. coli S1030 cells described above support PACE comparably to turbidostats cultures, and therefore used chemostats for the PACE experiments in this study.

Media for all chemostat PACE experiments was prepared by autoclaving a 20 L carboy of MilliQ water containing a custom Davis rich media formulation: anhydrous K2HPO4 (140 g), KH2PO4 (40 g), (NH4)2SO4 (20 g), NaCl (58 g), casamino acids (100 g), Tween-80 (20 mL), L-cysteine (1 g), Ltryptophan (0.5 g), adenine (0.5 g), guanine (0.5 g), cytosine (0.5 g), uracil (0.5 g), CaCl2 (0.5 µM final). This was allowed to cool overnight, and supplemented with a 500 mL filter-sterilized solution of MilliQ water containing: NaHCO$_3$ (16.8 g), glucose (90 g), sodium citrate (10 g), MgSO4 (1 g), FeSO4 (56 mg), thiamine (134 mg), calcium pantothenate (94 mg), para-aminobenzoic acid (54 mg), para-hydroxybenzoic acid (54 mg), 2,3-dihydroxybenzoic acid (62 mg), (NH4)6Mo7 (3 nM final), H3BO3 (400 nM final), CoCl2 (30 nM), CuSO4 (10 nM final), MnCl2 (80 nM final), and ZnSO4 (10 nM final). Cultures were supplemented with the appropriate antibiotics in the following final concentrations: carbenicillin (AP; 50 µg/mL), spectinomycin (APneg; 50 µg/mL), chloramphenicol (MP; 40 µg/mL). Streptomycin (for selection of S1030 cells carrying the rpsL marker) and tetracycline (for selection of the F plasmid) were not routinely included in culture media.

Real-time luminescence monitor. The in-line bioluminescence measurements were made by a modified luminometer. A TD-20e luminometer (Turner Designs) was installed inside a dark box in continuous reading mode. While in this mode, the luminometer outputs a DC voltage that varies between 0 and 4 V depending on the light level received by the photomultiplier fitted in the instrument (the range was set to the most sensitive one). This signal was sent to an Arduino Mega (Arduino) prototyping board through the analog input port. The Arduino board was controlled via Matlab (Mathworks), using a custom Graphical User Interface (GUI). Measurements were taken at around 100 Hz and then integrated to 1 s before being written by the software into a text file. To allow for multichannel recordings, the system was fitted with a custom tube holder that could hold up to four flow-through tubes with minimal cross talk between channels. Because the holder allows for only one tube to be observed at a time, it is mounted on a stepper motor that is in turn controlled using the Matlab GUI via the Arduino board and a Pololu A4988 stepper motor driver (Pololu R&E). The system waits until a measurement is complete before rotating the sample holder until the next tube is in position. The cycle repeats until all channels are covered, then unwinds to start a new cycle. The time between measurements of a particular channel is ~30 s. Data analysis comprised temporal binning and low-pass Fourier filtering of the raw traces.

Assay for infection-competence of recipient cells. Recipient cultures were grown to mid-log phase, and 100 µL of culture was mixed by pipetting with 2 µL of pJC126b phagemid prep (encodes R6K origin, f1 origin, pLac-YFP) totaling ~109 cfu. Reactions were incubated for 2 min and then 1 µL of the reaction was diluted into 1 mL of fresh 2×YT media. Cells were pelleted, resuspended in 1 mL fresh 2×YT, and an aliquot was diluted 10-fold into fresh media. 20 µL of the resulting media was plated on 2×YT-agar plates with 1 mM IPTG and grown overnight. Colonies were scanned on a Typhoon laser imager (488 nm laser, 520/40 filter).

Discrete assay for phage production. Cultures with candidate drift plasmids contained: $P_{T7}$ (pJC173b), pTet (pJC148i2), psp (pJC175e), psp-tet (pJC175g/h/k/m/n), psp-tet on MP (pJC184d5), psp-tet on colE1-spect plasmid (pJC184d-Sp). Cultures were grown to mid-log phase and infected with an excess of SP-T7. Cells were pelleted and washed to remove residual excess phage. Cells were reinoculated into fresh media and grown to OD600 ~0.8, and supernatants were saved for titering. OD600 values were measured to normalize phage titers.

Continuous flow experiment of PTet-gene III drift cassette. A chemostat culture of S1030 cells carrying an AP encoding PTet-gene III (pJC14812) was prepared and growth was equilibrated overnight at a flow rate of 400 mL/h in a chemostat volume of 250 mL. The next morning, two lagoons (40 mL each, flow rate from the chemostat of 100 mL/h) were seeded with 107 pfu of SP-T7. Lagoons received supplements delivered by syringe pump (flow rate 1 mL/h) consisting of either 20 μg/mL ATc (resulting in 200 ng/ml final concentration) or water only. At 4-hour intervals, 0.6-mL samples were taken from lagoons, measured discretely for luminescence, and centrifuged to remove cells. Supernatants were combined with an equal volume of 50% glycerol and stored in the freezer. Phage titers of supernatants were measured on S1030 cells containing an AP encoding $P_{T7}$-gene III (pJC173b).

Continuous flow experiment of Ppsp-gene III drift cassette. A chemostat culture of S1030 cells carrying an AP encoding Ppsp-gene III (pJC175e) was prepared and equilibrated overnight. The flow rate was 400 mL/h in a chemostat volume of 250 mL. The next morning, a lagoon (40 mL each, flow rate 100 mL/h) was started and seeded with 107 pfu of SP-T7WT. At 4-hour intervals, 0.6-mL samples were taken from the lagoon, measured discretely for luminescence, and centrifuged to remove cells. Supernatants were combined with an equal volume of 50% glycerol and stored in the freezer. Phage titers of supernatants were measured on S1030 cells containing an AP encoding $P_{T7}$-gene III (pJC173b).

Continuous flow experiment of Ppsp-tet-gene III drift cassette. A chemostat culture of S1030 cells carrying plasmid Ppsp-tet-gene III (pJC175h) was prepared equilibrated overnight. The flow rate was 400 mL/h in a chemostat volume of 250 mL. The next morning, two lagoons (40 mL each, flow rate 100 mL/h) were started and seeded with 107 pfu of $SP_{T7}$WT. Lagoons received supplements delivered by syringe pump (flow rate 1 mL/h) consisting of either 20 μg/mL ATc (resulting in 200 ng/mL final concentration) or water only. At 4-hour intervals, 0.6-mL samples were taken from the lagoon, measured discretely for luminescence, and centrifuged to remove cells. Supernatants were combined with an equal volume of 50% glycerol and stored in the freezer. Phage titers of supernatants were measured on S1030 cells containing an AP encoding $P_{T7}$-gene III (pJC173b).

Continuous flow experiment of Ppsp-tet-gene III drift cassette with ATc dose-dependent stringency. A chemostat culture of S1030 cells carrying a DP encoding Ppsp-tet-gene III with a mutagenesis cassette (pJC184d5) and an AP encoding $P_{T7}$-6×HisTag-gene III (pJC173c) was prepared and equilibrated overnight. The flow rate was 400 mL/h in a chemostat volume of 250 mL. The next morning, three lagoons (40 mL each, flow rate 100 mL/h) were started, with their waste lines diverted through the in-line luminescence monitor. Lagoons were seeded with a mixture containing 109 pfu SP-T7Dead (D812G) and 107 pfu SP-T7WT, along with ATc in an amount that brought the 40 mL lagoon to the target final ATc concentration for each lagoon. Lagoons received supplements delivered by syringe pump (flow rate 1 mL/h) consisting of either 15 μg/mL ATc (to make 150 ng/ml final concentration), 40 μg/mL ATc (to make 400 ng/mL final concentration), or no ATc (water only). At t=8 h, the lagoon receiving 40 μg/mL ATc was switched to receive water only. At timepoints t=2, 4, 6, 8, and 16 h, 0.6-mL samples were taken from the lagoon, measured individually for luminescence, and centrifuged to remove cells. Supernatants were combined with an equal volume of 50% glycerol and stored in the freezer.

Supernatants were analyzed for relative phage ratios using a PCR and analytical restriction digestion. 1 μL of each supernatant was added to a 20 μL qPCR reaction (iQ SYBR Green Mastermix, Biorad) with primers JC1480 (5'-TCCAGCACTTCTCCGCGATGCTC-3', SEQ ID NO: 3) and JC1481 (5'-GAAGTCCGACTCTAAGATGT CACG-GAGGTTCAAG-3', SEQ ID NO: 4) and amplified by PCR with SYBR Green fluorescence monitored following each amplification cycle. Samples were removed individually from the PCR block after exceeding a pre-determined fluorescence threshold, and placed on ice. Samples were then quantitated again by SYBR Green fluorescence in a plate reader, and approximately equal amounts of DNA from the reactions (normalized based on the fluorescence readings) were added to restriction digestion reactions. The digestion reactions used enzymes EcoRV and HindIII in buffer NEB2 with BSA and were performed following the manufacturer's instructions in 20 μL total volumes. Digestions were inactivated with heat, combined with 0.2 volumes of 5× loading dye containing Orange G and xylene cyanol, and analyzed by agarose gel electrophoresis (1% agarose, 0.5×TBE, 120V, 80 min). The electrophoresed gel was stained with SYBR Gold (Invitrogen) and imaged on a Typhoon laser scanner (excitation 488, emission 520/40 nm).

Continuous flow experiment of dose-dependent negative selection. A chemostat of S1030 host cells containing an AP encoding $P_{T7}$-gene III (pJC173c) and an APneg encoding $P_{T3}$-theophylline riboswitch-gene III-neg (pJC174c-R5) was prepared and equilibrated overnight at a flow rate of 400 mL/h in a chemostat volume of 250 mL. The next morning, three lagoons (40 mL each, flow rate 100 mL/h) were started, with their waste lines diverted through the in-line luminescence monitor. Lagoons were seeded with a mixture containing 1010 pfu SP-T7Prom and 104 pfu SP-T7Spec and allowed to equilibrate for 4.5 h; during this time the lagoons received 0.1 M NaOH at 0.5 mL/h by syringe pump to equilibrate the lagoons to the pH of the theophylline vehicle. After equilibration (t=0 h), lagoons received supplements delivered by syringe pump (flow rate 0.5 mL/h) consisting of either 200 mM theophylline (to make 1 mM final concentration), 15 mM theophylline (to make 75 μM final concentration), or vehicle only (0.1 M NaOH). After 16 h, the lagoon receiving vehicle only was switched to receive 200 mM theophylline (1 mM final concentration). At timepoints t=0, 2, 4, 6, 8, 10, 12, and 20 h, 0.6 mL-samples were taken from the lagoon, measured discretely for luminescence, and centrifuged to remove cells. Supernatants were combined with an equal volume of 50% glycerol and stored in the freezer.

Relative phage ratios in supernatant samples were assayed using a PCR and analytical restriction digestion. 1 μL of each supernatant was added to a 20 μL qPCR reaction (iQ SYBR Green Mastermix, Biorad) with primers JC1163 (5'-GGAGTACGCTGCATCGAGATGCTCA-3', SEQ ID NO: 5) and JC1488 (5'-GTAGAAATCAGCCAGTACAT-CACAAGACTC-3', SEQ ID NO: 6) and amplified by PCR with SYBR Green fluorescence monitored following each amplification cycle. Samples were removed individually from the PCR block after exceeding a pre-determined fluorescence threshold, then placed on ice. Samples were quantitated again by SYBR Green fluorescence in a plate reader, and approximately equal amounts of DNA from the reactions (normalized based on the fluorescence readings) were added to restriction digestion reactions. The digestion reactions used AvaII in buffer NEB4 and were performed according to manufacturer instructions in 20-μL total volumes. Digestions were combined with 0.2 volumes of 5× loading dye containing Orange G and xylene cyanol, and analyzed by agarose gel electrophoresis (1% agarose, 0.5×TBE, 120V, 80 min). The electrophoresed gel was stained with SYBR Gold (Invitrogen) and imaged on a Typhoon laser scanner (excitation 488, emission 520/40 nm).

Continuous evolution of T3-selective RNA polymerases. A chemostat culture of S1030 cells carrying a DP encoding Ppsp-tet-gene III with a mutagenesis cassette (pJC184d5) and an AP encoding $P_{T3}$-gene III (pJC174f) was prepared and equilibrated overnight at a flow rate of 400 mL/h in a chemostat volume of 250 mL. The next morning, two lagoons (50 mL each, flow rate 100 mL/h) were started, with their waste lines diverted through the in-line luminescence monitor.

Lagoons were seeded with 105 pfu of SP-T7WT. Lagoons received supplements delivered by syringe pump (flow rate 1 mL/h) consisting of either 20 μM ATc (in 500 mM L-arabinose) for lagoon 1 or vehicle alone (500 mM L-arabinose) for lagoon 2. At t=12 h, lagoon 1's supplement was changed to 2 μM ATc (in 500 mM L-arabinose). At t=28 h, the first chemostat was discontinued and both lagoons began receiving cells from a second chemostat containing S1030 cells harboring an MP (pJC184), a $P_{T3}$-gene III AP (pJC174f), and a $P_{T7}$-theophylline riboswitch-gene III-neg APneg (pJC173f-R5). Both lagoons received 500 mM L-arabinose. At t=32 h, half of lagoon 1 was transferred to a new lagoon, lagoon 3. Lagoons 1 and 3 were brought to 40 mL total volumes with culture from the chemostat, and lagoons were equilibrated for 40 min. Lagoons 1 and 2 then received 100 mM theophylline (dissolved in 0.1 M NaOH, flow rate 1 mL/h), while lagoon 3 received vehicle only (0.1 M NaOH). At t=52 h, the second chemostat was discontinued and all lagoons began receiving cells from a third chemostat containing S1030 cells harboring an MP (pJC184), a reduced RBS $P_{T3}$-gene III (pJC174k) and an enhanced RBS/copy number $P_{T7}$-gene III-neg APneg (pJC173g-SD8). All lagoon volumes were reduced to 40 mL each (flow rate maintained at 100 mL/h) and were supplemented with 500 mM L-arabinose. At t=70.5 h, lagoon volumes were reduced to 30 mL each, while the flow rate was maintained at 100 mL/h.

Periodically, 0.6 mL-samples were taken from the lagoon, measured discretely for luminescence, and centrifuged to remove cells. Supernatants were combined with an equal volume of 50% glycerol and stored in the freezer.

In vivo gene expression measurements on evolved RNA polymerases. Cells for luminescence assays were S1030 cells described above containing APs encoding Ppspgene III (pJC184c-rrnB) and either $P_{T7}$-luxAB (pJC173e4) or $P_{T3}$-luxAB (pJC174e4). Cells were grown to mid-log phase and 20-μL aliquots were distributed into a deep-well plate. 10 μL of clonal phage aliquots were added to these wells and plates were incubated at 37° C. for 15 min. Wells were supplemented with 500 μL media, grown to mid-log phase, and cells were transferred to a 96-well plate for luminescence measurement.

In vivo gene expression measurements on RNA polymerase forward mutants. Cells for luminescence assays were S1030 cells described above containing an expression plasmid (EP) expressing a subcloned forward mutant T7 RNAP and APs encoding either $P_{T7}$-luxAB (pJC173e4) or $P_{T3}$-luxAB (pJC174e4). Cultures were grown overnight and used to seed 500-μL cultures in 96-well blocks that were grown to mid-log phase, after which cells were transferred to a 96-well plate for luminescence measurement.

Discrete assays for phage production from candidate drift promoters. Cultures of S1030 E. coli cells with candidate drift plasmids containing $P_{T7}$-gene III (pJC173b), PTet-gene III (pJC14812), Ppsp-gene III (pJC175e), Ppsp-tet-gene III (pJC175g/h/k/m/n), Ppsp-tet-gene III on MP (pJC184d5), or Ppsp-tet-gene III on colE1-spect plasmid (pJC184d-Spect) were prepared and grown to mid-log phase in Davis rich media. Cultures were infected with an excess of SP-T7WT and incubated at 37° C. for 10 min. The resulting cells were pelleted and washed to remove residual excess phage. These cells were inoculated into fresh 2×YT media and grown to $OD_{600}=\sim 0.8$. Cells were removed by centrifugation. Phage supernatant was harvested from these cultures and used for titering by plaque assay on S1030 E. coli cells carrying a $P_{T7}$-gene III AP (pJC173b). Exact ODs were used to normalize phage titers.

Discrete assays for phage production from pIII-neg candidates. Cultures of S1030 E. coli cells with candidate pIII-neg plasmids containing PTet-gene III (pJC14812) and either Plac-C-domain (pJC156a2), Plac-C83 (pJC156c2), Plac-N1-N2-C83 (pJC156j2), Plac-N2-C83 (pJC156m2), or Plac-N1*-N2-C83 (pJC15602) were prepared and grown to mid-log phase in Davis rich media. Cultures were infected with an excess of SP-T7WT and incubated at 37° C. for 10 min. The resulting cells were pelleted and washed to remove residual excess phage. These cells were inoculated into fresh 2×YT media and grown in either 4 ng/ml or 20 ng/mL ATc and in the presence or absence of 2 mM IPTG. Cultures were grown to OD600=~0.9. Cells were removed by centrifugation. Phage supernatant was harvested from these cultures and used for titering by plaque assay on S1030 E. coli cells carrying a $P_{T7}$-gene III AP (pJC173b). Exact ODs were used to normalize phage titers.

Discrete assays for phage production using the theophylline-dependent negative selection. A culture of S1030 E. coli cells containing $P_{T7}$-gene III (pJC173c) and $P_{T3}$-theophylline riboswitch-gene III-neg (pJC174c-R5) were prepared and grown to mid-log phase in Davis rich media. Cultures were infected with an excess of either SP-T7192.2 or SP-T748.3 and incubated at 37° C. for 10 min. The resulting cells were pelleted and washed to remove residual excess phage. These cells were inoculated into fresh 2×YT media and grown with the indicated concentrations of theophylline. Cultures were grown to OD600=~ 0.8. Cells were removed by centrifugation. Phage supernatant was harvested from these cultures and used for titering by plaque assay on S1030 E. coli cells carrying a P17-gene III AP (pJC173b). Exact ODs were used to normalize phage titers.

Results

We hypothesized that selection stringency during PACE can be varied by providing host cells with regulated amounts of pIII in a manner independent of the desired evolving activity. To create this capability, we placed expression of gene III on an AP under the control of the small molecule-inducible TetA promoter (Ptet) and observed anhydrotetracycline (ATc) concentration-dependent gene III expression (FIG. 2). Although an AP containing Ptet-gene III supported ATc-dependent phage production in a discrete host cell culture (FIG. 2), this AP did not support robust phage propagation in a PACE format when ATc was added to a lagoon (FIG. 1c). Because even low levels of pIII render cells resistant to filamentous phage infection,[10] we hypothesized that these host cells, which begin producing pIII soon after entering a lagoon, become phage infection-resistant prior to encountering phage, thereby preventing phage propagation (FIG. 2).

To create a system in which activity-independent pIII expression requires both ATc and prior phage infection, we used the previously described *E. coli* phage shock promoter (Ppsp), which is induced by infection with filamentous phage via a pIV-dependent signaling cascade.[11] Transcription from Ppsp can also be induced by overexpression of a plasmid-encoded phage pIV gene.[12] Phage lacking gene III are known to form plaques on cells containing a Ppsp-gene III cassette.[13] We confirmed and extended this observation by showing that an AP with this cassette supports robust propagation in a PACE format (FIG. 1d).

To make phage propagation ATc-dependent, we examined the gene expression properties of Ppsp variants with TetR operators installed at positions intended to disrupt either PspF or *E. coli* RNA polymerase binding (FIG. 2). We found that placing an operator adjacent to the +1 transcription initiation site creates a promoter (Ppsp-tet) that is induced only with the combination of phage infection and ATc (FIG. 2). This AP supported robust ATc-dependent propagation of a SP with activity-independent gene III expression (FIG. 1e). High Ppsp-tet-gene III induction (200 ng/mL ATc) supported propagation with dilution rates of 2.5 vol/h, corresponding to an average of 30 phage generations per 24 hours. These results collectively demonstrate that SPs can propagate in an ATc-dependent, activity-independent manner using the Ppsp-tet-gene III AP, thus enabling selection stringency to be altered during PACE in a small molecule-regulated manner.

Tuning Selection Stringency During PACE. Next we examined how the Ppsp-tet-gene III cassette influences the enrichment of active library members over inactive library members in the context of an actual PACE selection in which an additional copy of gene III is controlled by an activity-dependent promoter. At saturating concentrations of ATc, the Ppsp-tet-gene III cassette should provide sufficient pIII to maximize phage propagation regardless of SP encoded activity, enabling genetic drift of the SP. At intermediate concentrations of ATc, SPs encoding active library members should enjoy a replicative advantage over a SP encoding an inactive variant by inducing additional pIII expression from an activity-dependent promoter. This advantage, and therefore selection stringency, should be inversely proportional to the concentration of ATc provided. In the absence of added ATc, selection stringency should be determined by the activity-dependent AP components with no assistance from the Ppsp-tet-gene III cassette.

Figure 3:
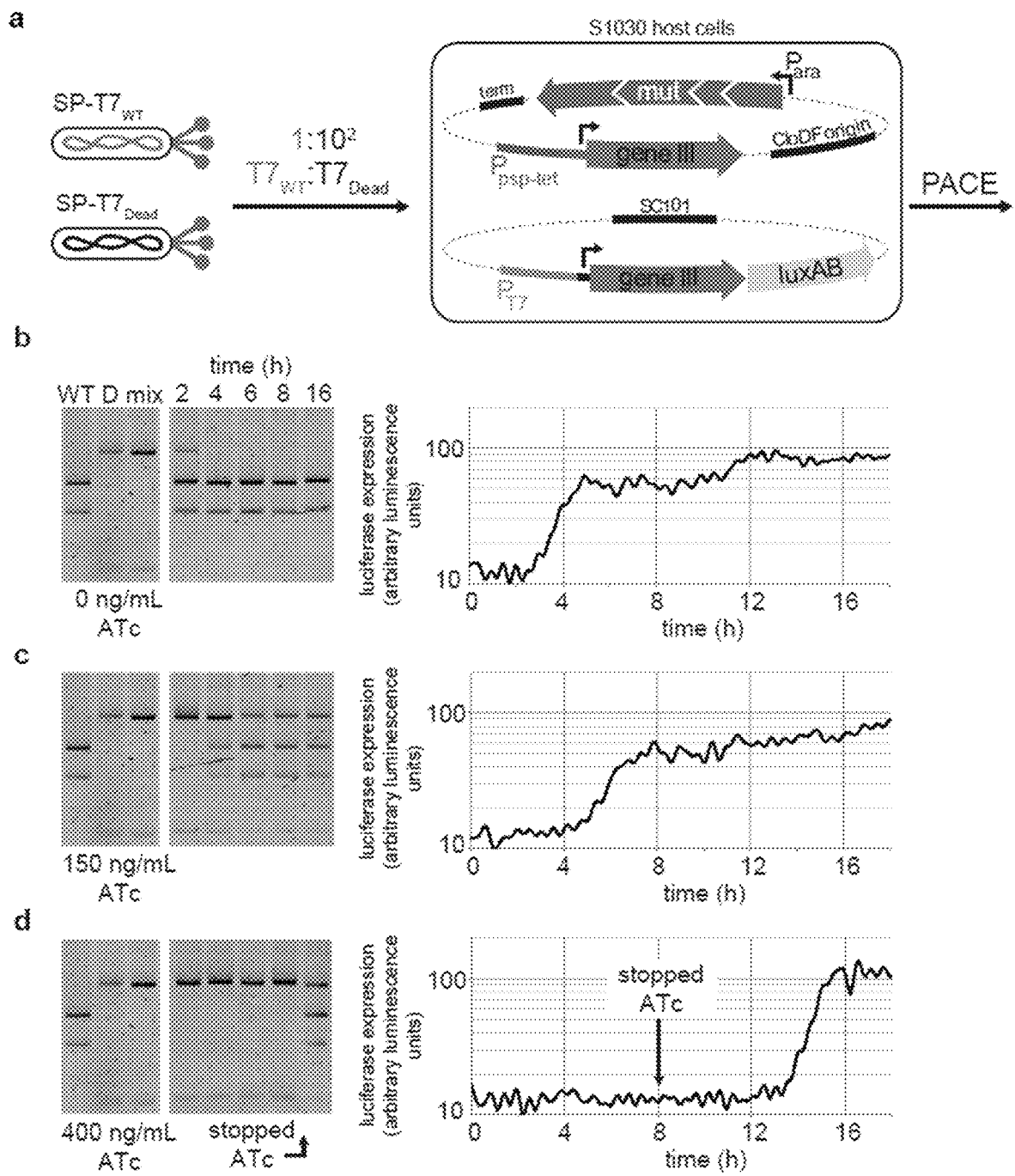
FIG. 3A-D. Drift cassette enables ATc-dependent, activity-independent phage propagation. Cells harboring APs with the indicated gene III-luxAB expression cassettes served as recipients for phage propagation experiments using SP-T7$_{WT}$. Data show representative single measurements of phage concentrations (n=1). (a) Recipient cells carrying a drift plasmid (DP) and a P$_{T7}$-gene III AP were used to propagate a mixture of SP-T7WT (wild-type T7 RNAP, high activity) and SP-T7Dead (D812G mutant T7 RNAP,[14] no activity) at a ratio of 1:10$^2$ ("Mix" in (b)). (b) In the absence of ATc, SP-T7WT (WT) is rapidly enriched over the inactive D812G mutant polymerase ("D") and a rapid increase in luciferase signal is observed. (c) At an intermediate ATc concentration (150 ng/mL), SP-T7WT is enriched at a slower rate, concurrent with a slower rise in luciferase signal. (d) At the highest ATc concentration (400 ng/mL), SP-T7WT is not enriched and baseline luciferase signal is observed. Upon ending ATc supplementation at t=8 h, SP-T7WT is rapidly enriched, and the luciferase signal rapidly rises.

To characterize the relationship between ATc concentration and selection stringency, we combined the Ppsp-tet-gene III cassette with the arabinose-inducible mutagenesis cassette[1] onto a single "drift plasmid" (DP) that is compatible with activity-dependent APs. We set up lagoons with continuously flowing host cells that contained both this DP and an AP with a $P_{T7}$-gene III cassette (FIG. 3a). We then seeded lagoons with a mixture of two SPs encoding either the highly active wild-type T7 RNAP (SP-T7WT) or the catalytically inactive mutant D812G (SP-T7Dead).[14] These phage were added in a ratio of 1:100 SP-T7WT:SP-T7Dead to each of three lagoons receiving either 0, 150, or 400 ng/ml ATc. The phage populations were followed over time using a combination of restriction endonuclease digests and real-time measurements of luminescence monitoring of $P_{T7}$ transcriptional activity.

As shown in FIG. 3b, under the highest stringency conditions (0 ng/ml ATc), SP-T7Dead washed out of the lagoon and the highly active SP-T7WT was enriched. At an intermediate concentration of ATc (150 ng/mL), SP-T7Dead again washed out in favor of SP-T7WT, but at a slower rate than in the absence of ATc (FIG. 3c). At the highest concentration of ATc (400 ng/mL), SP-T7Dead was able to propagate and no substantial enrichment of the active SP-T7WT was observed (FIG. 3d). When we stopped ATc supplementation to this lagoon, we observed very rapid enrichment of SP-T7WT consistent with the expected increase in stringency (FIG. 3d). Taken together, these results establish that Ppsp-tet-gene III supports propagation of inactive starting libraries in the presence of high ATc concentrations, and supports the selective enrichment of active mutants at a rate inversely proportional to the concentration of ATc added to the lagoon.

Development of a PACE Negative Selection. An ideal PACE negative selection inhibits infectious phage production in a manner that is tunable and proportional to the ratio of undesired (off-target) to desired (on-target) activity, rather than simply reflecting the absolute level of undesired activity. We therefore sought to develop a negative selection in which undesired activity induces expression of a protein that antagonizes the wild-type pIII induced in a positive selection.

The pIII protein consists of three domains, N1, N2, and C, that mediate initial attachment of the phage to the *E. coli* F-pilus (N2 domain), subsequent docking with the *E. coli* TolA cell-surface receptor (N1 domain), and unlocking of the particle for genome entry (C domain).[15,16] During progeny phage synthesis, five pIII molecules are attached by the C-domain to the end of each nascent phage particle.[17,18] A presumed conformational change in this C-domain then catalyzes detachment of the nascent phage from the inner membrane, thereby releasing the phage from the host cell.[16]

One pIII mutant described by Rakonjac and co-workers, N-C83, contains intact N1 and N2 domains but has a mutant C domain with an internal deletion of 70 amino acids.[16] The residual C domain is sufficient to mediate attachment to a phage particle, but its ability to catalyze detachment of nascent phage from the host cell membrane is hindered.[16] When co-expressed with a pIII variant containing only the intact C domain (which can mediate nascent phage detachment), phage particle production was found to be normal, but the infectivity of these particles was reduced.[16] These observations raised the possibility that N-C83 may function as a dominant negative mutant of wild-type pIII.

Figure 4:
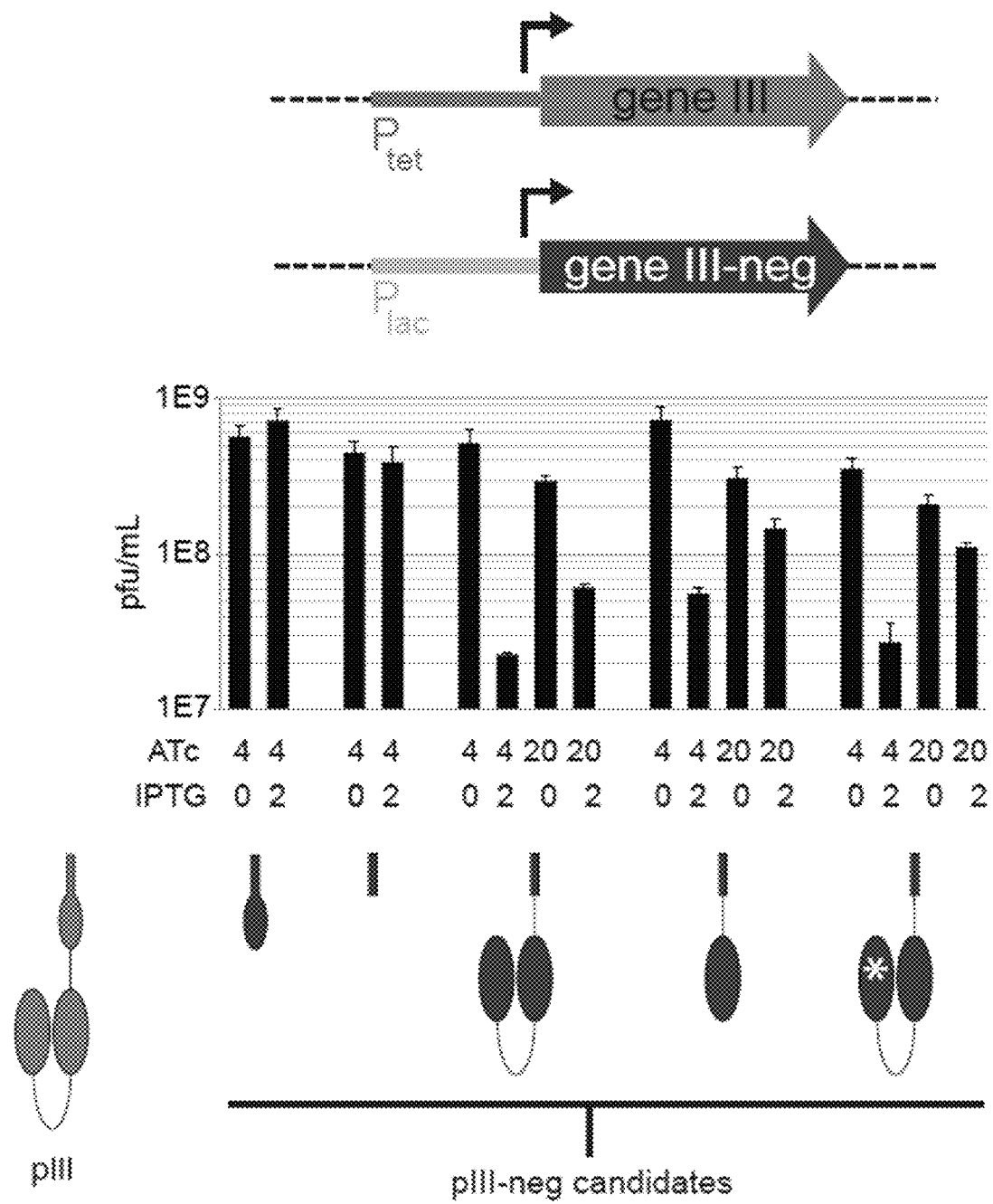
FIG. 4. Effect of pIII-neg candidate expression on infectious phage titer. Gene III expression is driven by P$_{tet}$ (induced by ATc), and the expression of a gene III-neg candidate is driven by pLac (induced by IPTG). Constructs from left to right are pJC156a2 (C-domain), pJC156c2 (C83), pJC156j2 (N-C83), pJC156m2 (N2-C83), pJC15602 (N*-C83). Amino acid sequences of the pIII-neg candidates are provided in FIG. 5. ATc was used at 4 or 20 ng/mL, and IPTG was used at 0 or 2 mM.
Figure 6:
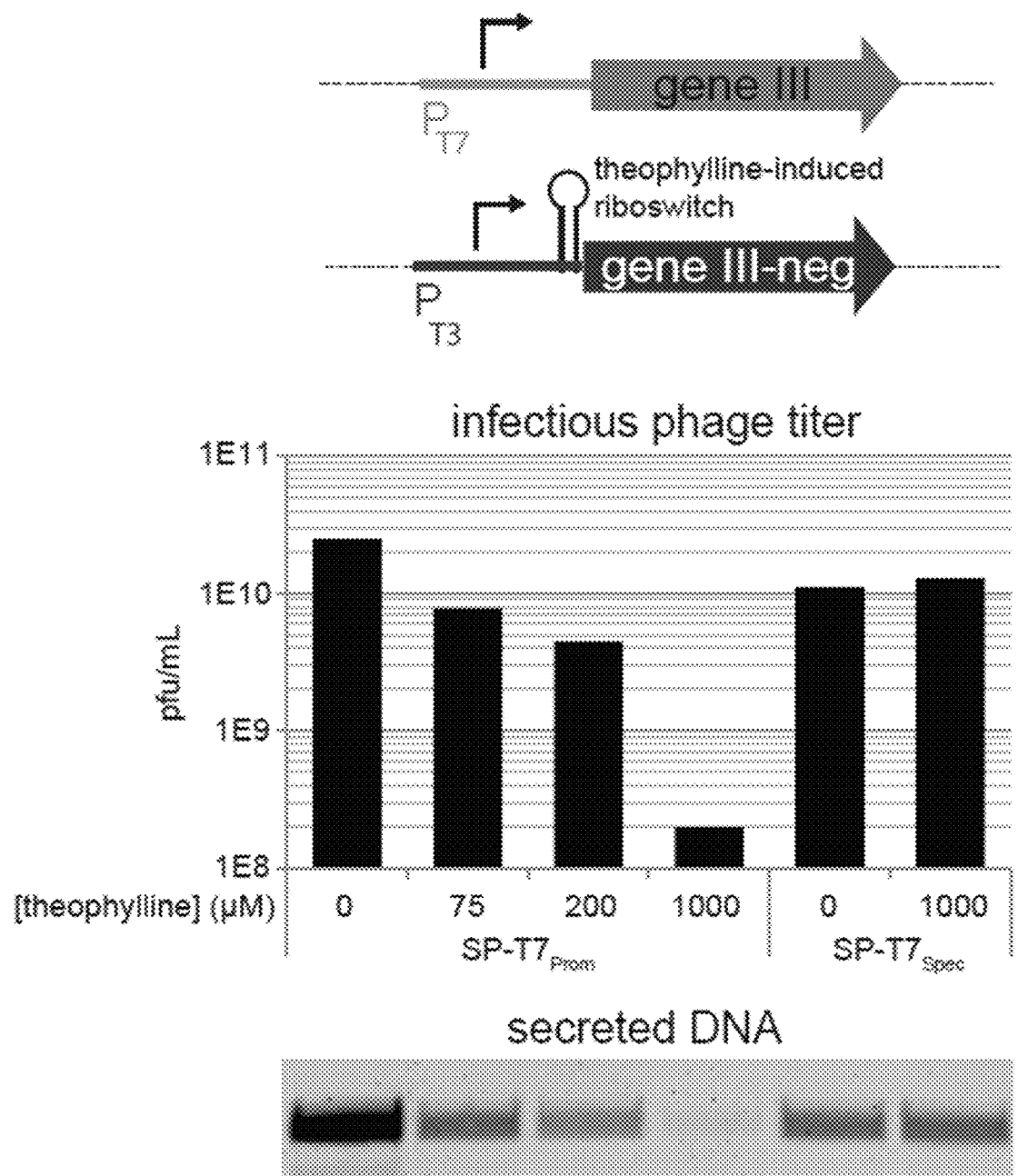
FIG. 6. Dose-dependent effect of pIII-neg expression on phage production. A selection phage (SP) encoding a promiscuous T7 RNAP variant (SP-T7$_{Prom}$) or an SP encoding a P$_{T7}$-specific RNAP variant (SP-T7$_{Spec}$) were used to infect cells harboring an AP in which P$_{T7}$ drives gene III expression and an AP-neg in which P$_{T3}$ drives gene III-neg expression in a theophylline-dependent manner. Cells were infected using excess phage for 10 min at 37° C., centrifuged and washed to remove residual phage, and resuspended in fresh Davis rich media. Infected cells were grown in the presence of the indicated concentrations of theophylline. The resulting titers of progeny phage after reaching mid-log phase are shown in the graph. SP-T7$_{Prom}$ results in fewer progeny phage only when theophylline is added. The total secreted DNA was also measured (bottom) and correlated with phage production. The X-axis numbers indicate the concentration of theophylline in micromolar (μM).

To test the suitability of N-C83 as the basis for a PACE negative selection, we created a host cell line containing an AP with a Ptet-gene III cassette induced by ATc, a second accessory plasmid (APneg) with N-C83 driven by an IPTG-inducible promoter (Plac). Discrete host cell cultures were grown in the presence or absence of ATc and IPTG, and culture broths were assayed for infectious phage titer. As expected, the addition of ATc induced expression of wild-type pIII and stimulated phage production (FIG. 4). The simultaneous addition of IPTG, which induces N-C83 expression, reduced the titer of infectious phage. This result suggests that N-C83 can act as a dominant negative form of pIII. Alternative truncation candidates of pIII did not diminish infectious phage titer to the same degree as N-C83 (FIG. 4). We also observed evidence to suggest that N-C83 may inhibit infectious phage production by blocking the release of phage from the host cell, rather than by reducing the infectivity of the released phage particles (FIG. 6). These results reveal that expression of N-C83 (pIII-neg), can form the basis of a potent negative selection.

PACE Negative Selection Can Enrich Substrate-Specific RNAP Variants. Next we tested if this negative selection could enrich a substrate-specific T7 RNAP over a promiscuous RNAP in the PACE format. For this competition experiment, we used SPs encoding two RNAP variants that we recently described: L2-48.3 (specific for $P_{T7}$, expressed from SP-T7Spec) and L1-192.2 (active on both $P_{T7}$ and $P_{T3}$, expressed from SP-T7Prom).[1] We prepared a host cell strain containing both a positive selection AP ($P_{T7}$-gene III AP) and a negative selection AP ($P_{T3}$-gene III-neg APneg) in which pIII-neg translation is controlled by a theophylline-activated riboswitch (FIG. 7a).[19] During PACE with this host cell strain, the propagation of SP-T7Prom should be impaired, relative to SP-T7Spec, in the presence of theophylline.

Figure 7:
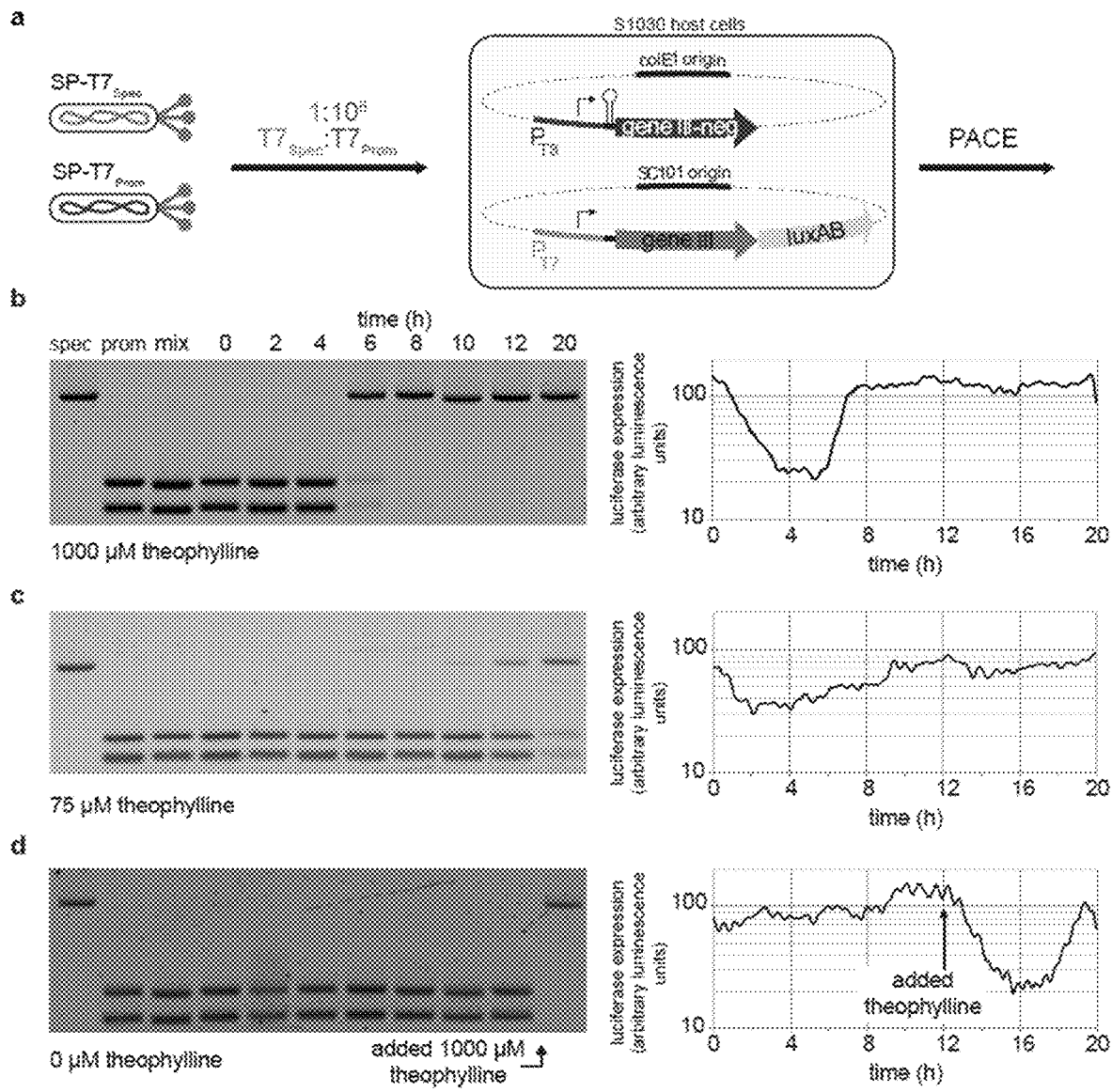
FIG. 7A-D. Dominant negative pIII-neg is a potent inhibitor of phage propagation. (a) Recipient cells carrying a P$_{T7}$-gene III AP and a P$_{T3}$-gene III-neg APneg in which the theophylline riboswitch controls gene III-neg expression were used to propagate a 1:10$^6$ mixture ("mix" in (b)) of SP-T7$_{Spec}$ (specific for P$_{T7}$, "spec") and SP-T7$_{Prom}$ (promiscuous on both P$_{T7}$ and P$_{T3}$, "prom"), respectively. (b) At a high theophylline concentration (1000 μM), the promiscuous T7 RNAP SP is rapidly depleted, and the specific T7 RNAP SP quickly takes over the lagoon, concomitant with a sharp rise in luciferase signal from P$_{T7}$. (c) At an intermediate theophylline concentration, the promiscuous T7 RNAP SP slowly washes out and is gradually replaced by the specific T7 RNAP SP, accompanied by a less drastic drop then gradual recovery of luciferase signal. (d) In the absence of theophylline, the promiscuous T7 RNAP SP propagates unhindered, and the lagoon maintains the starting ratio of the inoculated phage. Upon addition of high concentrations of theophylline to this lagoon at t=12 h, a rapid washout of the promiscuous T7 RNAP SP takes place, with a rebound in luciferase signal consistent with specific T7 RNAP SP enrichment. In (b)-(d), data show representative single measurements (n=1).

Three lagoons containing these host cells were each seeded with a $10^6$:1 ratio of SP-T7Prom:SP$_{T7}$Spec and allowed to equilibrate for about 4.5 hours. We treated the lagoons with 0, 75, or 1000 µM theophylline and followed the concentrations of the two SP species over time. In the presence of 1000 µM theophylline, SP-T7Prom was rapidly depleted from the lagoon and the SP-T7Spec population expanded into the predominant species after about 6 hours of PACE (FIG. 7b). Furthermore, the rate of enrichment was dependent on the concentration of theophylline added to the lagoon, where lower concentrations of theophylline resulted in slower enrichment rates (FIGS. 7c and 7d). These results demonstrate that pIII-neg can serve as the basis of a potent and dose-dependent negative selection that can effect the rapid enrichment of substrate-selective enzymes in a PACE format.

Figure 8:
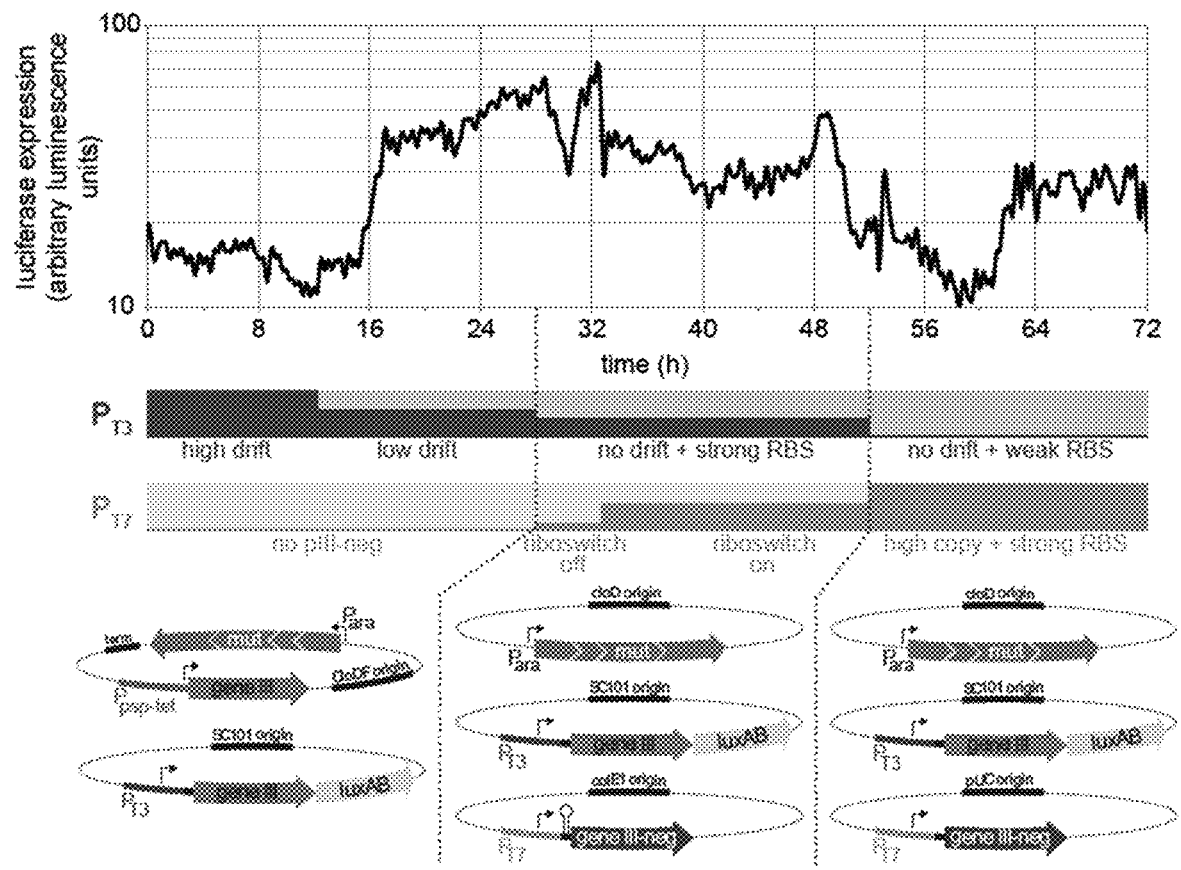
FIG. 8. Schedule for the continuous evolution of T3-specific RNAP variants. PACE of T7 RNAP variants that recognize P$_{T3}$ and reject P$_{T7}$ was performed in three contiguous stages of differing stringency, using three host cell strains carrying the combinations of plasmids shown (bottom). Arabinose was added to the lagoons at all timepoints to induce high levels of mutagenesis from the drift plasmid (DP) or mutagenesis plasmid (MP). The P$_{T3}$ and P$_{T7}$ bars conceptually represent amounts of gene III (red) or gene III-neg (blue) expressed from the respective promoters for a given amount of polymerase activity; therefore, fewer pIII molecules are generated from P$_{T3}$ and more pIII-neg molecules are generated from P$_{T7}$ for a given amount of polymerase activity as the experiment progresses. At t=0, host cells with the DP and a P$_{T3}$-gene III AP are fed into the lagoon. For the first 12 hours, 200 ng/mL ATc was added to the lagoon to reduce selection stringency to zero, thereby enabling drift. At t=12 h, the concentration of ATc was reduced to 20 ng/ml, resulting in an increase in selection stringency that allows weakly active variants to propagate. At t=28 h, host cells harboring an MP, a P$_{T3}$-gene III AP and a riboswitch-controlled P$_{T7}$-gene III-neg APneg were fed into the lagoons, initiating selection for variants capable of high levels of activity on P$_{T3}$. In the absence of theophylline, transcription through the theophylline riboswitch-P$_{T7}$ results in low levels of pIII-neg production and therefore low negative selection pressure against P$_{T7}$ recognition. At t=32, high levels of added theophylline (1 mM) was added to increase negative selection stringency, inducing a rapid reduction in luciferase signal consistent with the loss of promiscuous RNAP variants. At t=52 host cells containing an MP, a P$_{T3}$-gene III AP with a weaker ribosome binding site (RBS), and a P$_{T7}$-gene III-neg APneg with enhanced RBS/higher origin of replication copy number were fed into the lagoons to further increase negative and positive selection stringency. The in-line luminescence monitor was used throughout to infer population fitness (top). The luciferase signal again dropped, consistent with the loss of intermediate specificity variants from the pool, followed by rebound consistent with enrichment of highly P$_{T3}$-specific RNAP variants.

Continuous Evolution of RNAPs with Altered Promoter Specificities. We integrated both the tunable selection stringency and the negative selection developments described above to rapidly evolve enzymes with dramatically altered substrate specificity without the use of intermediate substrates. We prepared two lagoons with host cells containing a $P_{T3}$-gene III AP and the DP containing the Ppsp-tet-gene III cassette, and seeded these lagoons with SP-T7WT, which has negligible starting activity on $P_{T3}$. To one lagoon, we added no ATc and observed that phage quickly washed out.[1] To the second lagoon, we added 200 ng/mL ATc, which allowed even inactive phage to propagate. After 12 hours (t=12 h), the phage in this lagoon increased in concentration dramatically, but still encoded RNAPs with negligible activity on $P_{T3}$. We then reduced the concentration of ATc to 20 ng/mL, thus increasing the selection stringency for recognition of $P_{T3}$ (FIG. 8).

After an additional six hours of propagation in 20 ng/mL ATc (t=18 h), a $P_{T3}$-active population overtook the lagoon as indicated by an increase in signal from the in-line luminescence monitor. This signal continued to increase over the next 10 hours. RNAP clones isolated from the 28-hour time point evolved an ~100-fold increase in activity on $P_{T3}$ (FIG. 9) and converged on two mutations, E222K and N748D, that we[1] and others[20] previously found to broaden the substrate scope of T7 RNAP (FIG. 10). These results demonstrate that selection stringency modulation can be used to directly evolve a novel activity from an inactive starting gene without the use of intermediate substrates as evolutionary stepping-stones, as was previously used to evolve T3 promoter recognition without selection stringency modulation.[1]

Figure 9:
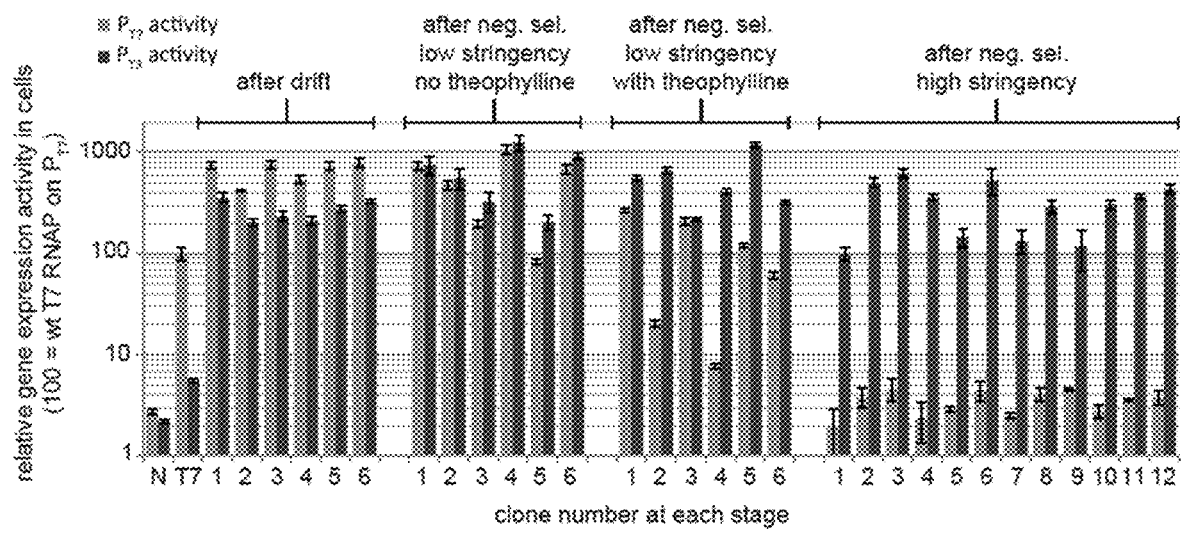
FIG. 9. Activities of continuously evolved RNAP variants with altered substrate specificities. Gene expression activities of randomly chosen RNAP clones (numbered along the X-axis in stages) isolated at the end of the drift stage (left, t=28 h), the low-stringency negative selection without theophylline (center left, t=32 h), the low-stringency negative selection with theophylline (center right, t=52 h), and the high-stringency negative selection (right, t=70.5 h) are shown. See FIG. 10 for mutations present in each clone. N=no RNAP; T7=wild-type T7 RNAP. Gene expression activities on the T7 and T3 promoters of randomly chosen clones from each stage were measured (bottom). Gene expression data show mean values±s.e.m. for two replicates. A list of mutations present in each clone is in FIG. 10. N, no RNAP; T7, wild-type T7 RNAP; NS, negative selection; mut, the arabinose-induced mutagenesis-enhancing genes.
Figure 10:
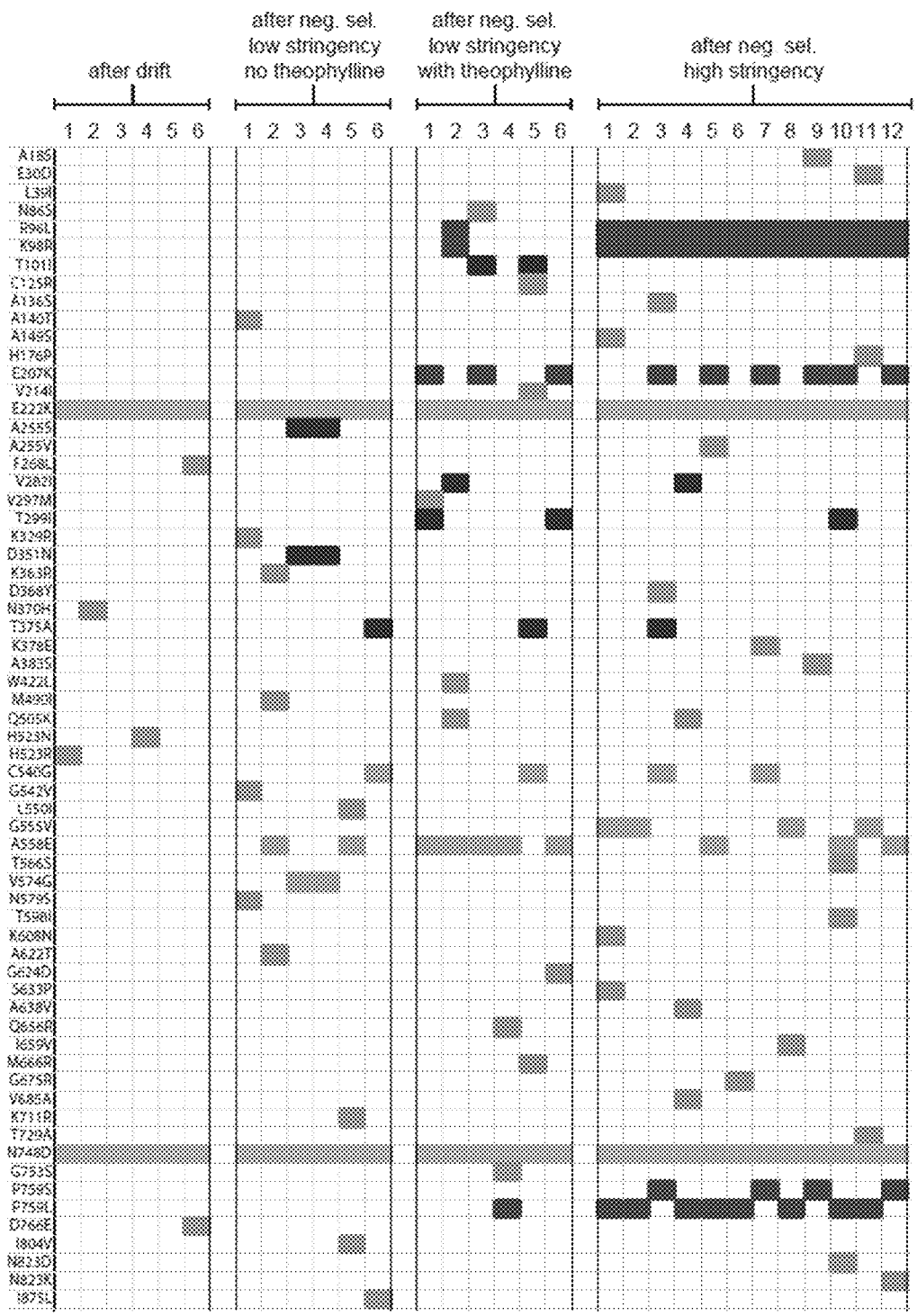
FIG. 10. Genotypes of continuously evolved RNAP variants. Mutations present in clones isolated following the drift stage (left, t=28 hrs), low-stringency negative selection without theophylline (center left, t=32 hrs), low-stringency negative selection with theophylline (center right, t=52 hrs), and high stringency negative selection (right, t=70.5 hrs). Mutations in blue are conserved in all clones and were found to confer activity on $P_{T3}$. Mutations in red are conserved in clones with high specificity for $P_{T3}$ over $P_{T7}$. Mutations in magenta are, as a group, conserved and predicted based on the structure of T7 RNAP 30 to be physically clustered, but mutually exclusive of each other (negatively epistatic). Mutations in grey or black are isolated or modestly conserved, respectively.

As shown in FIG. 9, the RNAPs recovered from this stage of the selection still retained high activity on $P_{T7}$. To initiate negative selection against recognition of $P_{T7}$, we used host cells containing the same $P_{T3}$-gene III AP, the MP (lacking the drift cassette), and a $P_{T7}$-gene III-neg APneg in which pIII-neg expression is driven by $P_{T7}$ transcription, and controlled by a theophylline-dependent riboswitch (FIG. 8). The 28-hour lagoon described above was divided into two new lagoons, each of which received these host cells for 4 hours. Theophylline was added to the first lagoon to activate the negative selection (t=32 h), whereas the second lagoon did not receive any theophylline. After 24 hours (t=52 h), several RNAPs isolated from the first lagoon showed clear improvements in specificity for $P_{T3}$ (FIG. 9) and contained a variety of mutations at residues proximal to the promoter in the initiation complex and known to be relevant to substrate selectivity. In contrast, clones isolated from the second lagoon, which did not receive theophylline, did not show clear changes in specificity.

In an effort to further enhance the specificity of the evolving RNAPs, we increased the stringency of the negative selection in two ways. First, we weakened the ribosome binding site driving translation of pIII from the AP, with the expectation that evolved RNAPs would compensate with increased (but still $P_{T3}$-selective) transcriptional activity. Second, we installed a high-copy pUC origin into APneg, and replaced the theophylline riboswitch with a very strong ribosome-binding site driving pIII-neg translation (FIG. 8). Together, these modifications should increase the stringency of the negative selection by increasing the ratio of pIII-neg to pIII produced for a given ratio of $P_{T7}$:$P_{T3}$ activity.

Figure 11:
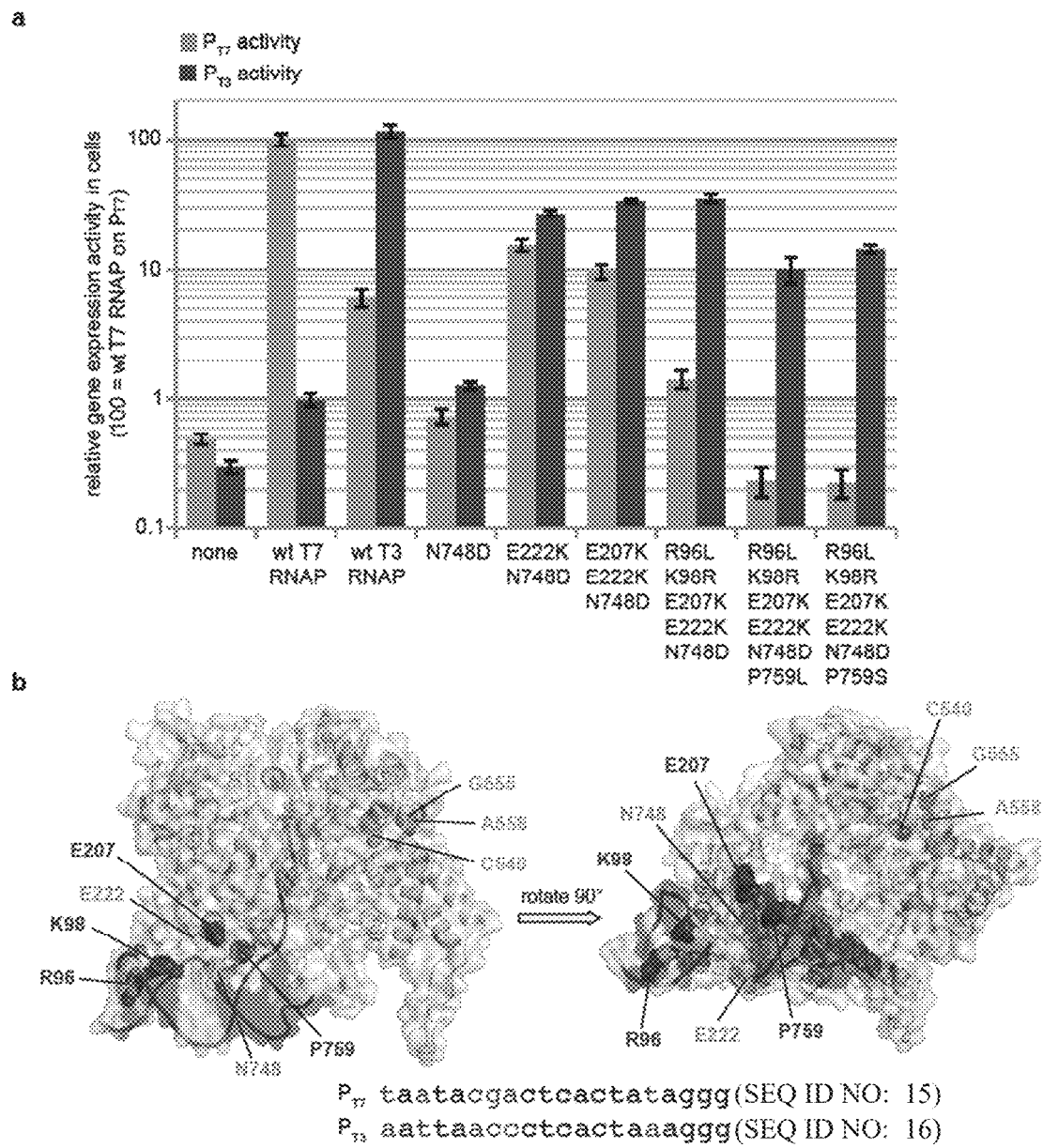
FIG. 11A-B. Analysis of evolved T7 RNAP mutations that confer $P_{T3}$ specificity. (a) The gene expression activity in cells of T7 RNAP variants containing subsets of mutations found in evolved clones described in FIG. 5 are shown on the T7 promoter (blue bars) and the T3 promoter (red bars). (b) Location of evolved mutations.[21] The T7 promoter DNA is rendered as dark blue and light purple surfaces, with light purple denoting nucleotide differences between the T7 and T3 promoters. Cyan spheres identify evolved mutations that enable $P_{T3}$ recognition. Red spheres identify mutations that evolved during negative selection that contribute to specific recognition of $P_{T3}$ over $P_{T7}$. Magenta spheres represent a conserved cluster of mutually exclusive mutations evolved in clones following negative selection. The sequences of the T7 and T3 promoters are shown at the bottom, with the differences in red (correspond to SEQ ID NOs: 15 and 16, respectively).

The phage population from the previous stage (t=52 h) was transferred to lagoons fed by these high-stringency host cells and a substantial decline and rebound of the phage population was observed (FIG. 8). Evolved RNAPs isolated following this recovery (t=70 h) exhibited dramatically improved specificity for $P_{T3}$ over $P_{T7}$ of up to 100-fold and strongly converged on mutations observed in the previous stage (R96L, K98R, E207K, P759S/L) (FIGS. 9 and 10). A forward mutational analysis of these mutations in the E222K/N748D background highlighted the role of each of these changes in conferring strong specificity for $P_{T3}$ (FIG. 11). The degree of specificity evolved using stringency control and negative selection PACE rivals or exceeds that of naturally occurring wild-type T7 or T3 RNA polymerase enzymes; for example, wild-type T7 RNAP exhibits a $P_{T7}$:$P_{T3}$ activity ratio of ~100-fold, and wild-type T3 RNAP exhibits a $P_{T3}$:$P_{T7}$ activity ratio of ~20-fold (FIG. 11). Compared to the wild-type T7 RNAP enzyme, the most $P_{T3}$-specific evolved RNAP clones exhibited a net ~10,000-fold change in specificity for $P_{T3}$. This remarkable degree of specificity did not evolve at the expense of activity, and all assayed clones retained levels of transcriptional activity on $P_{T3}$ that are comparable to or higher than that of wild-type T7 RNAP on its cognate T7 promoter (FIG. 9). Collectively, these results establish that the PACE negative selection can be used to explicitly evolve enzymes with altered specificity.

DISCUSSION

Traditional directed evolution techniques, while valuable and successful, require frequent researcher intervention throughout each round of mutation, screening or selection, and replication to access biomolecules with desired properties. By mapping the essential components of the directed evolution cycle onto the very rapid M13 filamentous bacteriophage lifecycle, PACE can dramatically accelerate laboratory evolution. In this work we have expanded the capabilities of PACE by developing a general strategy to modulate selection stringency—to zero if needed—with a small molecule, and by developing a negative selection that links undesired activities to the inhibition of phage propagation. Together, these capabilities were used to evolve RNA polymerase variants with ~10,000-fold altered promoter specificity (rather than merely broadened), in a PACE experiment lasting about three days.

T7 RNA polymerases that evolved the ability to accept the T3 promoter and reject the T7 promoter acquired a suite of highly conserved mutations, including R96L, K98R, E207K, E222K, N748D, and P759S/L. The mutations at positions 98 and 748 change each residue to the amino acid found in wild-type T3 RNAP, and the R96L mutation is at a position that also differs between wild-type T7 and T3 RNAPs (although it is K96 in T3 RNAP). These residues are predicted to be proximal to the promoter bases (FIG. 11b), and their role in promoter recognition has been previously appreciated.[21] The occurrence of these mutations in our selections suggests that the evolved mutants may use a mode of $P_{T3}$-selective promoter recognition similar to that of wild-type T3 RNAP at these positions. In contrast, residues 207, 222, and 759 are conserved between T7 and T3 RNAPs, and the significant role of mutations at these residues in conferring selectivity (particularly P759S/L, FIG. 11a) suggests the evolution of some novel determinants of promoter recognition that may not be used by the native enzymes. E207 modestly increases selectivity for $P_{T3}$ (FIG. 11a) and is within 4 Å of the RNAP specificity loop (residues 739-770), a major determinant of promoter specificity[22] that includes P759.

The negative selection uses a dominant negative variant of pIII, the protein that is the basis of the positive selection of PACE, and does not rely on the property of the gene or gene product being evolved. Therefore, we anticipate that the negative selection will be general in its compatibility with a variety of activities that can be evolved using PACE, provided that the selection scheme can link undesired activity to expression of pIII-neg (and not pIII). For many potential proteins that can be evolved with PACE, including DNA-binding proteins, recombinases, protein-protein interfaces, proteases, and other enzymes, a suitable dual selection scheme can be created by localizing undesired substrates upstream of pIII-neg production.[1] In most cases, such a negative selection can operate simultaneously with pIII-mediated positive selection. Likewise, since the method to modulate selection stringency developed here is affected by providing pIII in a regulated manner that is also independent of the evolving gene, this stringency modulation capability should also be applicable to other PACE experiments.

Example 2: Development of a PACE System for DNA-Binding Activity

Engineered proteins containing programmable DNA-binding domains (DBDs) can be used for targeted modification of nucleic acid molecules in vitro and in vivo and have the potential to become human therapeutics. The specificity of a DNA-binding domain is crucial to the efficacy and safety of the resulting DNA-binding proteins, such as nucleases or DNA-editing proteins. This disclosure illustrates a general approach for the continuous directed evolution of DNA-binding activity and specificity.

A general system for the continuous evolution of DNA-binding domains is presented. The system was validated by evolving restored DNA-binding activity in zinc fingers. The data presented here establish a new strategy for tuning the affinity and specificity of DBDs.

Results

To develop a PACE-compatible DNA-binding selection, a DNA-binding domain of interest was linked to a subunit of bacterial RNA polymerase III (RNAP). Binding of this fusion protein to operator sequences upstream of a minimal lac promoter induces transcription of a downstream gene III-luciferase reporter through recruitment or stabilization of the RNAP holoenzyme (FIG. 12, upper panel). To validate this strategy, an assay was developed that transduces cognate DNA-binding of the DBD from Zif268 (residues 333-420, see Choo, Y. & Klug, A. Toward a code for the interactions of zinc fingers with DNA: selection of randomized fingers displayed on phage. *Proc Natl Acad Sci USA* 91, 11163-7 (1994).), expressed from a tetracycline-inducible promoter, into activation of pIII-luciferase expression. This assay was used to evaluate a variety of DNA operator locations (at −55 and −62 bp with respect to the transcription initiation site, see Hu, J. C., Kornacker, M. G. & Hochschild, A. *Escherichia coli* one- and two-hybrid systems for the analysis and identification of protein-protein interactions. *Methods* 20, 80-94 (2000); and Durai, S., Bosley, A., Abulencia, A. B., Chandrasegaran, S. & Ostermeier, M. A bacterial one-hybrid selection system for interrogating zinc finger-DNA interactions. *Comb Chem High Throughput Screen* 9, 301-11 (2006).) and RNA polymerase fusion architectures.

Figure 13:
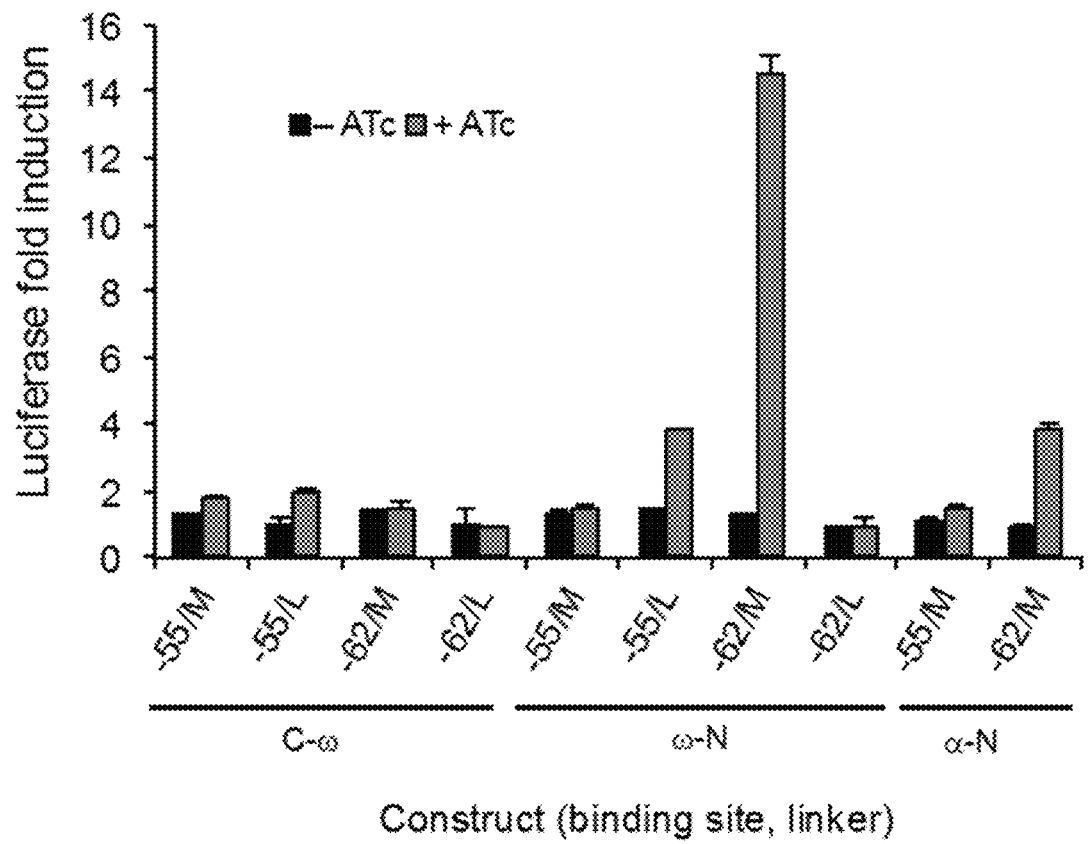
FIG. 13. Optimization of a one-hybrid architecture for PACE. Comparison of pIII-luciferase fold induction (ATc-induced Zif268 expression/non-induced luminescence) resulting from binding of a Zif268 fusion with either the a or @ subunit of RNAP to a Zif268 operator sequence (5'-GCGTGGGCG-3') centered at either −55 or −62. M refers to a medium-length linker between Zif268 and the RNAP subunit (AAATSGGGGAA, SEQ ID NO: 1), and L refers to a longer linker (AAGGGGSGGGGSGGGG-STAAA, SEQ ID NO: 2). Data represent mean±s.d. (n=3).

Fusing the RNAP ω-subunit to the N-terminus of Zif268 with an 11-residue linker resulted in ≥10-fold increase in pIII-luciferase production when the consensus Zif268 binding site (5'-GCGTGGGCG-3') was positioned at −62 (FIG. 13). To test the DNA specificity of this system, a control construct was created with an off-target Zif268 binding site in which the middle triplet of the target DNA site was changed to 5'-TTA-3'. Only *E. coli* containing the reporter downstream of the on-target sequence, but not those containing the off-target sequence, produced pIII-luciferase (FIG. 12, middle panel), establishing sequence-specific, DNA binding-dependent gene expression.

A series of negative selection APs (APNegs) was designed in which binding of a DBD to an off-target DNA sequence induces expression of gene III-neg (encoding pIII-neg) fused to yellow fluorescent protein (YFP) from a minimal lac promoter (FIG. 12, lower panel). To enable tuning of negative selection stringency, a theophylline-inducible riboswitch was placed upstream of gene III-neg-YFP. It was confirmed that phage propagation could be suppressed in a DNA-binding activity- and theophylline-dependent manner. Together, these results establish a negative selection system for DNA-binding PACE.

To integrate this system into PACE, the positive DNA operator-gene III-luciferase cassette and the negative DNA operator-gene IIIneg-YFP cassette was moved to accessory plasmids (APs), and the RNAP @-Zif268 protein was moved to a selection plasmid (SP).

Figure 14:
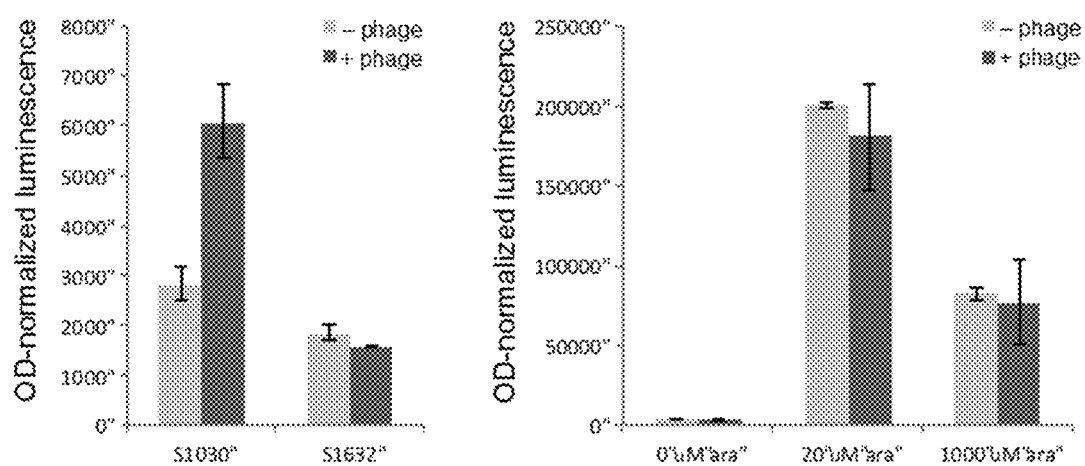
FIG. 14. Chromosomal pspBC deletion enables small-molecule control of the phage shock promoter response. Left panel: Comparison of phage-shock promoter response between S1030 and S1632 cells. Upon phage infection, activation of a phage shock promoter (PSP) induces bacterial luciferase expression, and can be measured as an increase in luminescence. The phage shock response sensors pspBC were deleted from S1632 cells, resulting in no transcriptional activation in the absence or presence of infecting phage. Right panel: Over-expression of pspBC from an arabinose-controlled promoter (PBAD) results in activation of the PSP in a manner independent of phage infection, eliminating variability in transcriptional activation of the promoter. Data represent mean±s.d. (n=3).
Figure 15:
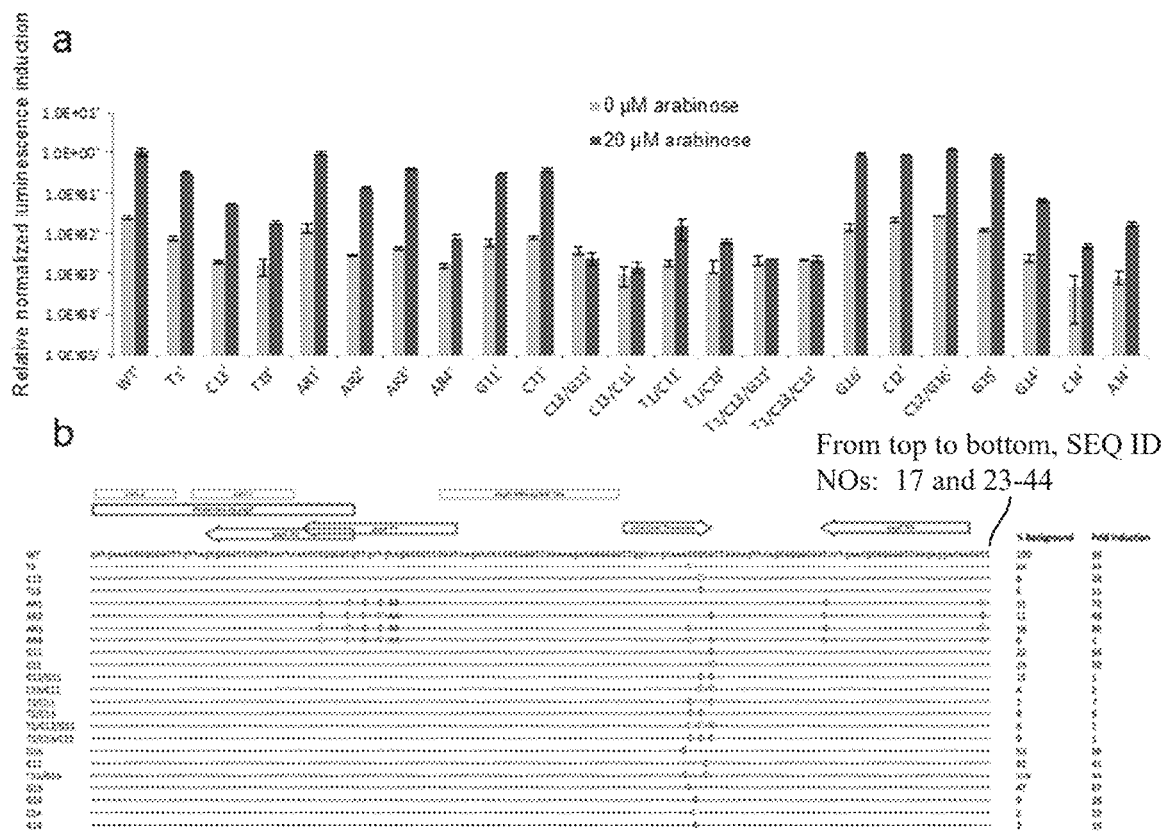
FIG. 15A-B. Generation of mutant PSP variants with altered dynamic range. Mutants abrogating the efficiency or background transcription of the PSP were constructed and tested through low-level expression of the phage shock sensors pspBC, which are master inducers of the phage shock response. Generally, mutations were focused on the σ 54 core promoter. The "AR" series carried additional mutations to reduce the strength of σ 70 cryptic promoters that may influence background transcription levels. (a) Luminescence signal in in the presence or absence of 20 µM arabinose from wild-type and mutant PSP promoters. All readings were normalized to wild-type PSP, which was set to 1. Data represent mean±s.d. (n=3). (b) Summary of activity, background levels, and genotypes of mutant promoters assayed in (a). Background levels of all mutant promoters are listed relative to wild-type. Sequences from top to bottom correspond to SEQ ID NOs: 17 and 23-44.
Figure 16:
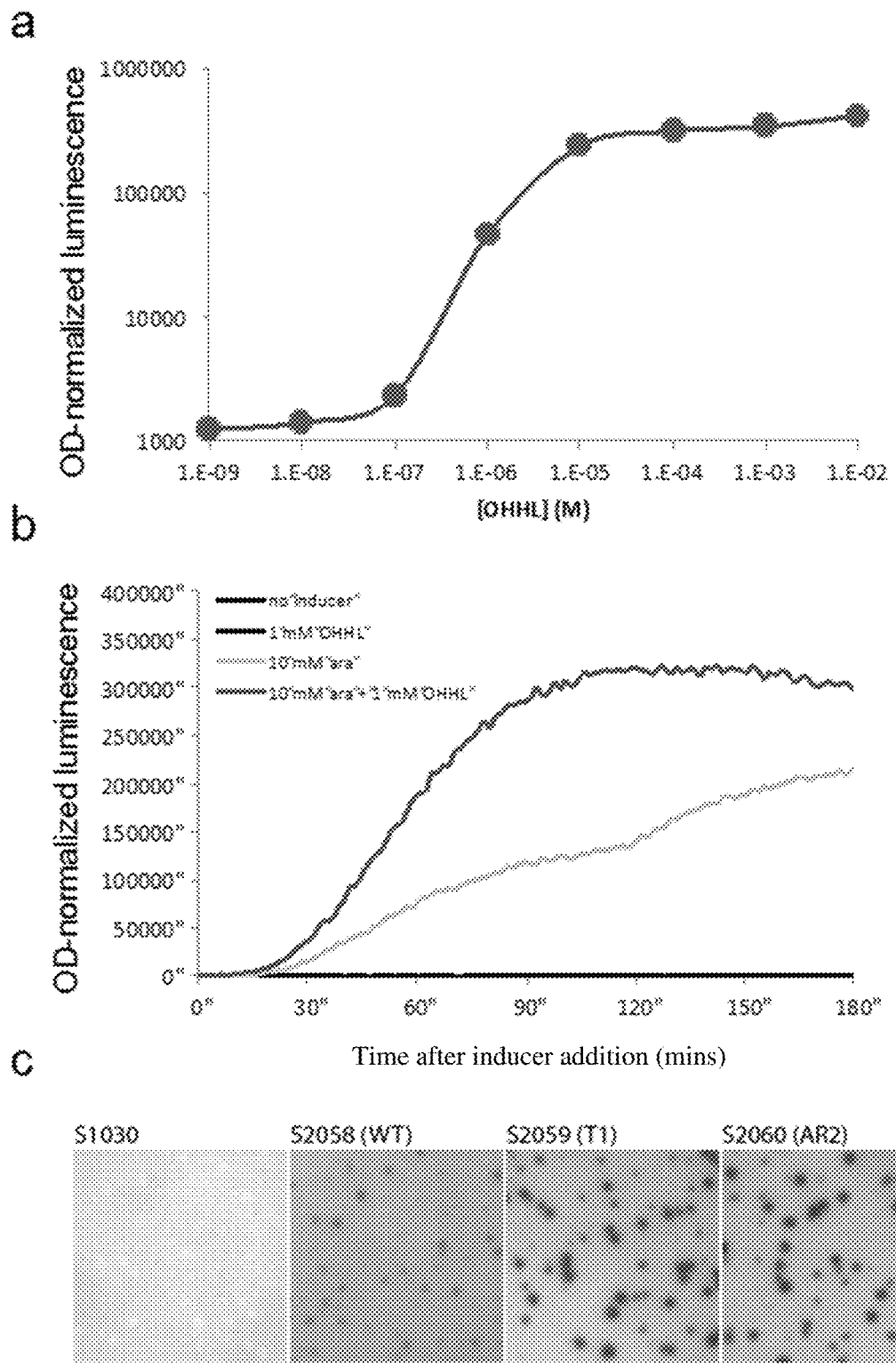
FIG. 16A-C. Generation of S2060, a bacterial strain for chaperone overexpression and robust visualization of phage plaques. (a) Luminescence resulting from induction of a bacterial luciferase (luxAB) cassette driven by the $P_{lux}$ promoter in response to the indicated doses of N-(3-oxohexanoyl)-1-homoserine lactone (OHHL) (the LuxR transcriptional regulator is also controlled by the $P_{lux}$ promoter, only in the opposite direction). Data represent mean±s.d. (n=3). (b) Kinetic analysis of OHHL-mediated expression of GroESL (cassette: luxR-$P_{lux}$-groESL) on the folding of LuxAB (cassette: araC-$P_{BAD}$-LuxAB), a known substrate for GroESL. Increased in vivo concentrations of GroESL result in improved folding of LuxAB and rapid saturation of the luminescence response. (c) Comparison of the ability to visualize plaque formation using S1030, S2058, S2059, and S2060 cells. Chromosomally identical strains lacking (S1030) or carrying the lacZ and groESL cassettes (S2058, S2059, S2060) were infected with WT M13 bacteriophage. The modified strains carry the wild-type (WT) PSP, PSP-T1 or PSP-AR2, respectively. The reduced background and maintained transcriptional activation of the T1 and AR2 variants enables the visualization of phage plaques in top agar supplemented with Bluo-Gal, an X-Gal derivative.

An *E. coli* strain designated S2060 was developed that is capable of inducing LacZ in response to activation of the phage shock promoter, a transcriptional regulatory element that responds to a number of environmental signals including filamentous phage infection (FIGS. 14-16). This strain can be used in combination with colorimetric LacZ substrates such as X-gal to stain bacteria that have been infected with phage.

Figure 17:
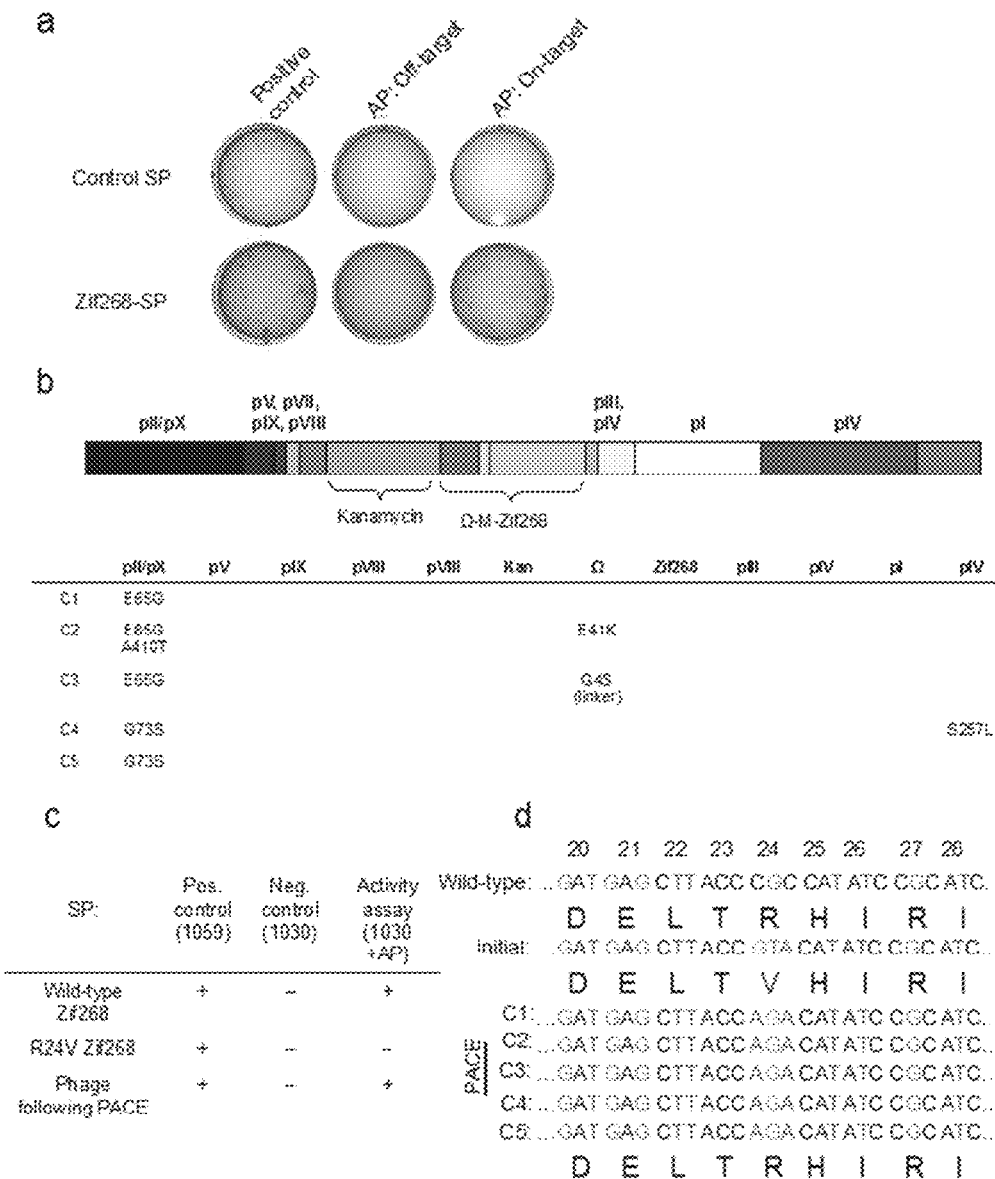
FIG. 17A-D. Continuous propagation of Zif268 in PACE, and reversion of an inactive Zif268 mutant to wild-type. (a) Plaque assays of Zif268-SP or a control SP encoding T7 RNAP instead of Zif268 on S2060 cells containing APs encoding either the on- or off-target sequence, or S2208 cells (positive control; see Example 2 for genotype information). (b) Schematic of the relative location of genes in the Zif268-SP, and a summary of mutations arising following 24 h of PACE to optimize the phage backbone and one-hybrid system. (c) Plaque assay results for wild-type Zif268-SP, inactive mutant Zif268-R24V-SP, and evolved SPs derived from a 24 h drift/24 h PACE experiment in the presence of mutagenesis. '+' denotes the presence of plaques, while '−' denotes the absence of plaques. Sequences from top to bottom correspond to SEQ ID NOs: 18, 21, 19, 22, 20, 20, 20, 20, 20, and 21. (d) Genotypes of five phage clones isolated following PACE, all displaying reversion of V24 to R.

It was tested whether ω-Zif268-SP could propagate in a DNA binding activity-dependent manner on S2060 cells containing an AP with the cognate Zif268 binding sequence, or a mutated binding sequence. Robust formation of colored plaques was observed, indicative of phage propagation, on cells harboring the on-target AP, but not on cells harboring an AP containing the off-target sequence (FIG. 17a). These observations demonstrate DNA binding activity-dependent phage propagation.

An initial PACE experiment was performed to optimize the SP backbone. SPs encoding Zif268 were propagated in PACE over 24 h on host cells carrying the cognate AP plasmid and a mutagenesis plasmid (MP, see Esvelt, K. M., Carlson, J. C. & Liu, D. R. A system for the continuous directed evolution of biomolecules. Nature 472, 499-503 (2011). After 24 h of PACE, the surviving SPs contained mutations in the phage genes encoding pII/X and pIV, and the fusion protein linker (FIG. 17b). These results collectively establish a basis for the continuous evolution of DBDs using PACE.

To validate the ability of this positive selection PACE system to improve DNA-binding activity, the system was used to evolve DNA binding in an inactive Zif268 mutant protein. Mutation of Arg24 in Zif268 to a small hydrophobic residue is known to abrogate DNA binding (Elrod-Erickson, M. & Pabo, C. O. Binding studies with mutants of Zif268. Contribution of individual side chains to binding affinity and specificity in the Zif268 zinc finger-DNA complex. J Biol Chem 274, 19281-5 (1999).). A lagoon was seeded with inactive ω-Zif268 SP containing an R24V mutation. After 24 h of neutral drift (mutation in the absence of any selection pressure) followed by 24 h of PACE on host cells containing the cognate AP, the evolved SPs were capable of propagating on the target AP (FIG. 17c). All of the sequenced phage clones at the end of the 24-h PACE experiment contained the V24R reversion mutation using an Arg codon not present in the wild-type gene (AGA vs. CGC) (FIG. 17d). Collectively, these results validate that this system can rapidly evolve proteins with DNA-binding activity.

The DNA-binding PACE system developed in this work can be used to rapidly tune the activity and specificity of a variety of DNA binding proteins. A distinguishing feature of DNA-binding PACE is that it does not require the use of pre-defined selection libraries that can constrain or bias evolutionary outcomes. The unconstrained manner in which mutations arise during PACE facilitates the discovery of evolved solutions with desired properties that could not be rationalized a priori.

Materials and Methods

Phage-assisted continuous evolution (PACE) of DNA-binding domains. In general, PACE setup was performed as previously described (Carlson, J. C., Badran, A. H., Guggiana-Nilo, D. A. & Liu, D. R. Negative selection and stringency modulation in phage-assisted continuous evolution. Nat Chem Biol 10, 216-22 (2014)). E. coli were maintained in chemostats containing 200 mL of Davis' Rich Media (DRM) using typical flow rates of 1-1.5 vol/h. DRM media was supplemented with appropriate antibiotics to select for transformed plasmids: APs (50 µg/mL carbenicillin), APNegs (75 µg/mL spectinomycin), MPs (25 µg/mL chloramphenicol). Lagoon dilution rates were 1.3-2 vol/h. In all PACE experiments S1030 cells carried an MP, either the previously reported pJC184 (Carlson et al., 2014, see above), or a variant of this plasmid lacking RecA. Mutagenesis was induced by continuously injecting arabinose (500 mM) at a rate of 1 mL/h into each 40-mL lagoon. Typical phage titers during each PACE experiment were $10^6$-$10^8$ p.f.u./mL.

Reversion of Zif268-V24R. A lagoon receiving host cell culture from a chemostat containing S1059 cells transformed with an MP was inoculated with Zif268-V24R phage. The lagoon flow rate during drift was 2 vol/h. After 24 h of drift, phage were isolated and used to inoculate a PACE experiment with S1030 host cells carrying pAP-Zif268 and an MP. Evolved phage were isolated after 24 h and characterized using plaque assays.

Luciferase assay. pOH plasmids were transformed by electroporation into S1030 cells, and grown overnight at 37° C. on LB-agar plates supplemented with 50 µg/mL carbenicillin. Single colonies were used to inoculate cultures which were allowed to grow for ~12 h at 37° C. in DRM supplemented with 50 µg/mL carbenicillin in a shaker. Cultures were diluted to an $OD_{600}$ of ~0.3 and allowed to grow for an additional 2 h at 37° C. Next, each culture was diluted 1:15 into 300 µL of DRM supplemented with 50 µg/mL carbenicillin in the presence or absence of 200 ng/mL anhydrotetracycline and incubated in a 96-well plate for an additional 4-6 h (shaking). 200 µL aliquots of each sample were then transferred to 96-well opaque plates and luminescence and $OD_{600}$ readings were taken using a Tecan Infinite Pro instrument. Luminescence data were normalized to cell density by dividing by the $OD_{600}$ value.

Plaque assays. S1030 cells were transformed with the appropriate plasmids via electroporation and grown in LB media to an $OD_{600}$ of 0.8-1.0. Diluted phage stock samples were prepared ($10^{-4}$, $10^{-5}$, $10^{-6}$, or $10^{-1}$-fold dilution) by adding purified phage stock to 250 µL of cells in Eppendorf tubes. Next, 750 µL of warm top agar (0.75% agar in LB, maintained at 55° C. until use) was added to each tube. Following mixing by pipette, each 1 mL mixture was pipetted onto one quadrant of a quartered petri plate that had previously been prepared with 2 mL of bottom agar (1.5% agar in LB). Following solidification of the top agar, plates were incubated overnight at 37° C. prior to analysis. Colorimetric plaque assays were performed in parallel with regular plaque assays using S2060 cells instead of S1030 cells, and used S-Gal/LB agar blend (Sigma) in place of regular LB-agar.

YFP assays. pTet plasmids were co-transformed with pAPNeg plasmids by electroporation into S1030 cells, and grown overnight at 37° C. on LB-agar plates supplemented with 50 µg/mL carbenicillin and 100 µg/mL spectinomycin. Single colonies were used to inoculate cultures which were allowed to grow for ~12 h in antibiotic-supplemented DRM in a bacterial shaker. Cultures were diluted to an $OD_{600}$ of ~0.3 and allowed to grow for an additional 2 h at 37° C. Next, each culture was diluted 1:15 into 300 µL of DRM supplemented with antibiotics and 5 mM theophylline in the presence or absence of 50 ng/mL anhydrotetracycline and incubated in a 96-well deep well plate for an additional 4-6 h (shaking). 200 µL aliquots of each sample were then transferred to 96-well opaque plates and YFP fluorescence ($\lambda_{ex}$=514 nm, $\lambda_{em}$=527 nm) and $OD_{600}$ readings were taken using a Tecan Infinite Pro instrument. Fluorescence data were normalized to cell density by dividing by the $OD_{600}$ value.

| \multicolumn{7}{c}{Plasmid constructs} |
|---|---|---|---|---|---|---|
| Name | Class | Res. | Ori. | Promoter | Binding Site | Gene |
| pOHZif268-1 | One-hybrid test plasmid | Carb | SC101 | $P_{lac}$ (pIII-luc) $P_{tet}$ (Zif268 fusion) | −55 (Zif268) | pIII-luxAB Zif268 DBD-(M)-rpoZ |
| pOHZif268-2 | One-hybrid test plasmid | Carb | SC101 | $P_{lac}$ (pIII-luc) $P_{tet}$ (Zif268 fusion) | −55 (Zif268) | pIII-luxAB Zif268 DBD-(L)-rpoZ |
| pOHZif268-3 | One-hybrid test plasmid | Carb | SC101 | $P_{lac}$ (pIII-luc) $P_{tet}$ (Zif268 fusion) | −62 (Zif268) | pIII-luxAB Zif268 DBD-(M)-rpoZ |
| pOHZif268-4 | One-hybrid test plasmid | Carb | SC101 | $P_{lac}$ (pIII-luc) $P_{tet}$ (Zif268 fusion) | −62 (Zif268) | pIII-luxAB Zif268 DBD-(L)-rpoZ |
| pOHZif268-5 | One-hybrid test plasmid | Carb | SC101 | $P_{lac}$ (pIII-luc) $P_{tet}$ (Zif268 fusion) | −55 (Zif268) | pIII-luxAB rpoZ Zif268 DBD |
| pOHZif268-6 | One-hybrid test plasmid | Carb | SC101 | $P_{lac}$ (pIII-luc) $P_{tet}$ (Zif268 fusion) | −55 (Zif268) | pIII-luxAB rpoZ L)-Zif268 DBD |
| pOHZif268-7 | One-hybrid test plasmid | Carb | SC101 | $P_{lac}$ (pIII-luc) $P_{tet}$ (Zif268 fusion) | −62 (Zif268) | pIII-luxAB rpoZ Zif268 DBD |
| pOHZif268-7: TTA | One-hybrid test plasmid | Carb | SC101 | $P_{lac}$ (pIII-luc) $P_{tet}$ (Zif268 fusion) | −62 5'GCGTTA GCG3' | pIII-luxAB rpoZ Zif268 DBD |
| pOHZif268-8 | One-hybrid test plasmid | Carb | SC101 | $P_{lac}$ (pIII-luc) $P_{tet}$ (Zif268 fusion) | −62 (Zif268) | pIII-luxAB rpoZ L)-Zif268 DBD |
| pOHZif268-9 | One-hybrid test plasmid | Carb | SC101 | $P_{lac}$ (pIII-luc) $P_{tet}$ (Zif268 fusion) | −55 (Zif268) | pIII-luxAB rpoA Zif268 DBD |
| pOHZif268-10 | One-hybrid test plasmid | Carb | SC101 | $P_{lac}$ (pIII-luc) $P_{tet}$ (Zif268 fusion) | −62 (Zif268) | pIII-luxAB rpoA Zif268 DBD |
| SPZif268 | SP | Kan | F1 | $P_{gIII}$ | — | rpoZ-(M)-Zif268 DBD |
| SPZif268-R24V | SP | Kan | F1 | $P_{gIII}$ | — | rpoZ-(M)-Zif268 DBD-R24V |
| pAPZif268 | AP | Carb | SC101 | $P_{lac}$ | −62 (Zif268) | pIII-luxAB |
| pAPZif268: TTA | AP | Carb | SC101 | $P_{lac}$ | −62 5'GCGTTA GCG3' | pIII-luxAB |

| \multicolumn{2}{c}{Genotypes of bacterial strains used} | |
|---|---|
| Strain | Genotype |
| S1030 | F' proA+B+ Δ(lacIZY) zzf::Tn10 lacI$^{Q1}$ $P_{N25}$-tetR luxCDE/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ⁻ |
| S1059 | F' proA+B+ Δ(lacIZY) zzf::Tn10 lacI$^{Q1}$ $P_{N25}$-tetR luxCDE/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ λ⁻ pJC175e |
| S1632 | F' proA+B+ Δ(lacIZY) zzf::Tn10 lacI$^{Q1}$ $P_{N25}$-tetR luxCDE/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC ΔpspBC λ⁻ |
| S2058 | F' proA+B+ Δ(lacIZY) zzf::Tn10 lacI$^{Q1}$ $P_{N25}$-tetR luxCDE $P_{psp}$ lacZ luxR $P_{lux}$ groESL/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ⁻ |
| S2059 | F' proA+B+ Δ(lacIZY) zzf::Tn10 lacI$^{Q1}$ $P_{N25}$-tetR luxCDE $P_{psp}$(T1) lacZ luxR $P_{lux}$ groESL/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ⁻ |
| S2060 | F' proA+B+ Δ(lacIZY) zzf::Tn10 lacI$^{Q1}$ $P_{N25}$-tetR luxCDE $P_{psp}$(AR2) lacZ luxR $P_{lux}$ groESL/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ⁻ |

| Genotypes of bacterial strains used | |
|---|---|
| Strain | Genotype |
| S2208 | F' proA+B+ Δ(lacIZY) zzf::Tn10 lacI^Q1 P_N25-tetR luxCDE P_psp(AR2) lacZ luxR P_lux groESL/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ⁻ pJC175e |

DNA Sequence of ω-Zif268-DBD fusion protein. Bases 997-1260 of *M. musculus* Zif268, corresponding the zinc finger DNA-binding domain (residues 333-420, see Wolfe, S. A., Nekludova, L. & Pabo, C. O. DNA recognition by Cys2His2 zinc finger proteins. *Annu Rev Biophys Biomol Struct* 29, 183-212 (2000)), were cloned downstream of the RNAP ω subunit:

```
                                              (SEQ ID NO: 7)
atggcacgcgtaactgttcaggacgctgtagagaaaattggtaaccgttt tgacctggtactggtcgccgcgcgtcgcgctcgtcagatgcaggtaggcg gaaaggatccgctggtaccggaagaaaacgataaaaccactgtaatcgcg ctgcgcgaaatcgaagaaggtctgatcaacaaccagatcctcgacgttcg cgaacgccaggaacagcaagagcaggaagccgctgaattacaagccgtta ccgctattgctgaaggtcgtcgtgcggcgggcggcggcggcagcaccgcg gcggctgaacgcccatatgcttgccctgtcgagtcctgcgatcgccgctt ttctcgctcggatgagcttacccgccatatccgcatccacacaggccaga agcccttccagtgtcgaatctgcatgcgtaacttcagtcgtagtgaccac cttaccacccacatccgcacccacacaggcgagaagccttttgcctgtga catttgtgggaggaagtttgccaggagtgatgaacgcaagaggcatacca aaatccatttaagacagaagtaa
```

Coding Sequence for ω-Zif268-DBD fusion protein. The protein sequence of the ω-Zif268-DBD fusion protein is shown below. The residues highlighted in bold correspond to the @ subunit, while the underlined residues correspond to the 11-amino acid linker. Residues downstream of the linker comprise the Zif268-DBD (residues 333-420).

```
                                              (SEQ ID NO: 8)
M A R V T V Q D A V E K I G N R F D L V L V A A R

R A R Q M Q V G G K D P L V P E E N D K T T V I A

L R E I E E G L I N N Q I L D V R E R Q E Q Q E Q

E A A E L Q A V T A I A E G R R A A G G G S T A

A A E R P Y A C P V E S C D R R F S R S D E L T R

H I R I H T G Q K P F Q C R I C M R N F S R S D H

L T T H I R T H T G E K P F A C D I C G R K F A R

S D E R K R H T K I H L R Q K
```

REFERENCES

1. Esvelt, K. M., Carlson, J. C. & Liu, D. R. A system for the continuous directed evolution of biomolecules. *Nature* 472, 499-503 (2011)
2. Nelson, F. K., Friedman, S. M. & Smith, G. P. Filamentous phage DNA cloning vectors: a noninfective mutant with a nonpolar deletion in gene III. *Virology* 108, 338-350 (1981)
3. Calendar, R. *The bacteriophages.* 2nd edn, (Oxford University Press, 2006).
4. Sergeeva, A., Kolonin, M. G., Molldrem, J. J., Pasqualini, R. & Arap, W. Display technologies: application for the discovery of drug and gene delivery agents. *Adv Drug Deliv Rev* 58, 1622-1654, (2006)
5. Yuan, L., Kurek, I., English, J. & Keenan, R. Laboratory-directed protein evolution. *Microbiol Mol Biol Rev* 69, 373-392
6. Leconte, A. M. et al. A population-based experimental model for protein evolution: effects of mutation rate and selection stringency on evolutionary outcomes. *Biochemistry* 52, 1490-1499 (2013)
7. Dickinson, B. C., Leconte, A. M., Allen, B., Esvelt, K. M. & Liu, D. R. Experimental interrogation of the path dependence and stochasticity of protein evolution using phage-assisted continuous evolution. *Proc Natl Acad Sci USA* 110, 9007-9012 (2013)
8. Doyon, J. B., Pattanayak, V., Meyer, C. B. & Liu, D. R. Directed evolution and substrate specificity profile of homing endonuclease I-SceI. *J Am Chem Soc* 128, 2477-2484 (2006)
9. Tracewell, C. A. & Arnold, F. H. Directed enzyme evolution: climbing fitness peaks one amino acid at a time. *Curr Opin Chem Biol* 13, 3-9 (2009)
10. Boeke, J. D., Model, P. & Zinder, N. D. Effects of bacteriophage f1 gene III protein on the host cell membrane. *Mol Gen Genet* 186, 185-192 (1982)
11. Brissette, J. L., Weiner, L., Ripmaster, T. L. & Model, P. Characterization and sequence of the *Escherichia coli* stress-induced psp operon. *J Mol Biol* 220, 35-48 (1991)
12. Brissette, J. L., Russel, M., Weiner, L. & Model, P. Phage shock protein, a stress protein of *Escherichia coli*. *Proc Natl Acad Sci USA* 87, 862-866 (1990)
13. Rakonjac, J., Jovanovic, G. & Model, P. Filamentous phage infection-mediated gene expression: construction and propagation of the gIII deletion mutant helper phage R408d3. *Gene* 198, 99-103 (1997)
14. Bonner, G., Lafer, E. M. & Sousa, R. Characterization of a set of T7 RNA polymerase active site mutants. *J Biol Chem* 269, 25120-25128 (1994)
15. Rakonjac, J., Feng, J. & Model, P. Filamentous phage are released from the bacterial membrane by a two-step mechanism involving a short C-terminal fragment of pIII. *J Mol Biol* 289, 1253-1265 (1999)
16. Bennett, N. J. & Rakonjac, J. Unlocking of the filamentous bacteriophage virion during infection is mediated by the C domain of pIII. *J Mol Biol* 356, 266-273 (2006)
17. Grant, R. A., Lin, T. C., Konigsberg, W. & Webster, R. E. Structure of the filamentous bacteriophage f1. Location of the A, C, and D minor coat proteins. *J Biol Chem* 256, 539-546 (1981)

18. Lopez, J. & Webster, R. E. Minor coat protein composition and location of the A protein in bacteriophage f1 spheroids and I-forms. *J Virol* 42, 1099-1107 (1982)
19. Lynch, S. A. & Gallivan, J. P. A flow cytometry-based screen for synthetic riboswitches. *Nucleic Acids Res* 37, 184-192 (2009)
20. Raskin, C. A., Diaz, G., Joho, K. & McAllister, W. T. Substitution of a single bacteriophage T3 residue in bacteriophage T7 RNA polymerase at position 748 results in a switch in promoter specificity. *J Mol Biol* 228, 506-515 (1992)
21. Cheetham, G. M., Jeruzalmi, D. & Steitz, T. A. Structural basis for initiation of transcription from an RNA polymerase-promoter complex. *Nature* 399, 80-83 (1999)
22. Imburgio, D., Rong, M., Ma, K. & McAllister, W. T. Studies of promoter recognition and start site selection by T7 RNA polymerase using a comprehensive collection of promoter variants. *Biochemistry* 39, 10419-10430 (2000)
23. Datsenko, K. A. & Wanner, B. L. One-step inactivation of chromosomal genes in *Escherichia coli* K-12 using PCR products. *Proc Natl Acad Sci USA* 97, 6640-6645 (2000)
24. Dove, S. L. & Hochschild, A. Conversion of the omega subunit of *Escherichia coli* RNA polymerase into a transcriptional activator or an activation target. *Genes Dev* 12, 745-754 (1998)
25. Xi, L., Cho, K. W. & Tu, S. C. Cloning and nucleotide sequences of lux genes and characterization of luciferase of *Xenorhabdus luminescens* from a human wound. *J Bacteriol* 173, 1399-1405 (1991)
26. Hammar, M., Arnqvist, A., Bian, Z., Olsen, A. & Normark, S. Expression of two csg operons is required for production of fibronectin- and congo red-binding curli polymers in *Escherichia coli* K-12 *Mol Microbiol* 18, 661-670 (1995)
27. Danese, P. N., Pratt, L. A., Dove, S. L. & Kolter, R. The outer membrane protein, antigen 43, mediates cell-to-cell interactions within *Escherichia coli* biofilms. *Mol Microbiol* 37, 424-432 (2000)
28. Wang, X., Preston, J. F., 3rd & Romeo, T. The pgaABCD locus of *Escherichia coli* promotes the synthesis of a polysaccharide adhesin required for biofilm formation. *J Bacteriol* 186, 2724-2734 (2004)
29. Khlebnikov, A., Datsenko, K. A., Skaug, T., Wanner, B. L. & Keasling, J. D. Homogeneous expression of the P(BAD) promoter in *Escherichia coli* by constitutive expression of the low-affinity high-capacity AraE transporter. Microbiology 147, 3241-3247 (2001).
30. Cheetham, G. M., Jeruzalmi, D. & Steitz, T. A. Structural basis for initiation of transcription from an RNA polymerase-promoter complex. *Nature* 399, 80-83, doi: 10.1038/19999 (1999).

All publications, patents and sequence database entries mentioned herein, including those items listed in the Summary, Brief Description of the Drawings, Detailed Description, and Examples sections, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A vector system comprising: a selection phagemid, a low selection stringency plasmid, and a high selection stringency plasmid, wherein
    the low selection stringency plasmid comprises a first nucleic acid encoding a first pIII protein that is operably linked to a small molecule inducible promoter;
    the high selection stringency plasmid comprises a second nucleic acid encoding a second pIII protein that is operably linked to an activity-dependent promoter comprising a binding site for a DNA-binding gene product; and
    the selection phagemid comprises a third nucleic acid encoding the DNA-binding gene product.

2. The vector system of claim 1, wherein binding of the DNA-binding gene product to the DNA-binding gene product binding site activates the activity-dependent promoter.

3. The vector system of claim 1, wherein the small molecule inducible promoter is a drift promoter.

4. The vector system of claim 1, wherein the low selection stringency plasmid comprises a mutagenesis cassette under the control of a second small-molecule inducible promoter.

5. The vector system of claim 1, wherein the activity-dependent promoter comprises a T7 promoter.

6. The vector system of claim 3, wherein the drift promoter is a $P_{psp-tet}$ promoter.

7. The vector system of claim 1 further comprising an E. coli host cell comprising a negative selection gene and a dominant negative mutant gene of a pIII protein.

8. The vector system of claim 1, wherein the selection phagemid comprises all viral genes required for the generation of viral particles, except for a full-length pIII gene that is required to package the selection phagemid into infectious viral particles.

9. The vector system of claim 7, wherein the E. coli host cell is of the genotype F'proA+B+Δ(lacIZY) zzf::Tn10 (TetR) lacIQ1 PN25-tetR luxCDE/endA1 recA1 galE15 galK16 nupG rpsL(StrR) ΔlacIZYA araD139 Δ(ara,leu)7697 mcrA Δ(mrr-hsdRMS-mcrBC) proBA::pir116 araE201 ΔrpoZ Δflu ΔcsgABCDEFG ΔpgaC λ-.

10. The vector system of claim 1, wherein the DNA-binding gene product is selected from the group consisting of polymerases, transcription factors, nucleases, and methylases.

11. The vector system of claim 10, wherein the DNA-binding gene product is an RNA polymerase.

12. The vector system of claim 1, wherein the expression of the pIII protein is required to package the selection viral phagemid into infectious viral particles.

13. The vector system of claim 1, wherein the pIII protein comprises the amino acid sequence set forth in SEQ ID NO: 9.

14. The vector system of claim 7, wherein the dominant negative mutant gene of the pIII protein is situated on an accessory plasmid.

15. The vector system of claim 7, wherein the dominant negative mutant gene of the pIII protein is under the control of a riboswitch.

16. The vector system of claim 15, wherein the riboswitch is a theophylline-activated riboswitch.

17. The vector system of claim 7, wherein the negative selection gene comprises a negative selection promoter.

18. The vector system of claim 17, wherein the negative selection promoter is a T3 or T7 promoter.

19. The vector system of claim 7, wherein the dominant negative pIII protein comprises any one of the amino acid sequences set forth in SEQ ID NOs.: 10-14.

20. The vector system of claim 18, wherein the dominant negative pIII protein comprises the amino acid sequence set forth in SEQ ID NO: 10.

* * * * *

```
                         SEQUENCE LISTING

<160> NUMBER OF SEQ ID NOS: 44

<210> SEQ ID NO 1
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 1
aaatsgggga a                                                         11

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 2
aaggggsggg gsggggstaa a                                              21

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
tccagcactt ctccgcgatg ctc                                            23

<210> SEQ ID NO 4
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 4
gaagtccgac tctaagatgt cacggaggtt caag                                34

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 5
ggagtacgct gcatcgagat gctca                                          25

<210> SEQ ID NO 6
<211> LENGTH: 30
<212> TYPE: DNA
<213> ORGANISM: Artificial Sequence
<220> FEATURE:
<223> OTHER INFORMATION: Synthetic polynucleotide
```

<400> SEQUENCE: 6
gtagaaatca gccagtacat cacaagactc         30

<210> SEQ ID NO 7
<211> LENGTH: 573
<212> TYPE: DNA
<213> ORGANISM: Artificial Sequence
<220> FEATURE:
<223> OTHER INFORMATION: Synthetic polynucleotide

<400> SEQUENCE: 7
atggcacgcg taactgttca ggacgctgta gagaaaattg gtaaccgttt tgacctggta         60
ctggtcgccg cgcgtcgcgc tcgtcagatg caggtaggcg gaaaggatcc gctggtaccg        120
gaagaaaacg ataaaaccac tgtaatcgcg ctgcgcgaaa tcgaagaagg tctgatcaac        180
aaccagatcc tcgacgttcg cgaacgccag gaacagcaag agcaggaagc cgctgaatta        240
caagccgtta ccgctattgc tgaaggtcgt cgtgcggcgg gcggcggcgg cagcaccgcg        300
gcggctgaac gcccatatgc ttgccctgtc gagtcctgcg atcgccgctt ttctcgctcg        360
gatgagctta cccgccatat ccgcatccac acaggccaga agcccttcca gtgtcgaatc        420
tgcatgcgta acttcagtcg tagtgaccac cttaccaccc acatccgcac ccacacaggc        480
gagaagcctt ttgcctgtga catttgtggg aggaagtttg ccaggagtga tgaacgcaag        540
aggcatacca aaatccattt aagacagaag taa                                     573

<210> SEQ ID NO 8
<211> LENGTH: 190
<212> TYPE: PRT
<213> ORGANISM: Artificial Sequence
<220> FEATURE:
<223> OTHER INFORMATION: Synthetic polypeptide

<400> SEQUENCE: 8

Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Gln Glu Ala Ala Glu Leu
65                  70                  75                  80

Gln Ala Val Thr Ala Ile Ala Glu Gly Arg Arg Ala Ala Gly Gly Gly
                85                  90                  95

Gly Ser Thr Ala Ala Ala Glu Arg Pro Tyr Ala Cys Pro Val Glu Ser
            100                 105                 110

Cys Asp Arg Arg Phe Ser Arg Ser Asp Glu Leu Thr Arg His Ile Arg
        115                 120                 125

Ile His Thr Gly Gln Lys Pro Phe Gln Cys Arg Ile Cys Met Arg Asn
    130                 135                 140

Phe Ser Arg Ser Asp His Leu Thr Thr His Ile Arg Thr His Thr Gly
145                 150                 155                 160

Glu Lys Pro Phe Ala Cys Asp Ile Cys Gly Arg Lys Phe Ala Arg Ser
                165                 170                 175

Asp Glu Arg Lys Arg His Thr Lys Ile His Leu Arg Gln Lys

<210> SEQ ID NO 9
<211> LENGTH: 424
<212> TYPE: PRT
<213> ORGANISM: Escherichia coli

<400> SEQUENCE: 9

```
Met Lys Lys Leu Leu Phe Ala Ile Pro Leu Val Val Pro Phe Tyr Ser
1               5                   10                  15
His Ser Ala Glu Thr Val Glu Ser Cys Leu Ala Lys Pro His Thr Glu
            20                  25                  30
Asn Ser Phe Thr Asn Val Trp Lys Asp Asp Lys Thr Leu Asp Arg Tyr
        35                  40                  45
Ala Asn Tyr Glu Gly Cys Leu Trp Asn Ala Thr Gly Val Val Val Cys
    50                  55                  60
Thr Gly Asp Glu Thr Gln Cys Tyr Gly Thr Trp Val Pro Ile Gly Leu
65                  70                  75                  80
Ala Ile Pro Glu Asn Glu Gly Gly Ser Glu Gly Gly Gly Ser Glu
                85                  90                  95
Gly Gly Gly Ser Glu Gly Gly Thr Lys Pro Pro Glu Tyr Gly Asp
            100                 105                 110
Thr Pro Ile Pro Gly Tyr Thr Tyr Ile Asn Pro Leu Asp Gly Thr Tyr
        115                 120                 125
Pro Pro Gly Thr Glu Gln Asn Pro Ala Asn Pro Asn Pro Ser Leu Glu
    130                 135                 140
Glu Ser Gln Pro Leu Asn Thr Phe Met Phe Gln Asn Asn Arg Phe Arg
145                 150                 155                 160
Asn Arg Gln Gly Ala Leu Thr Val Tyr Thr Gly Thr Val Thr Gln Gly
                165                 170                 175
Thr Asp Pro Val Lys Thr Tyr Tyr Gln Tyr Thr Pro Val Ser Ser Lys
            180                 185                 190
Ala Met Tyr Asp Ala Tyr Trp Asn Gly Lys Phe Arg Asp Cys Ala Phe
        195                 200                 205
His Ser Gly Phe Asn Glu Asp Pro Phe Val Cys Glu Tyr Gln Gly Gln
    210                 215                 220
Ser Ser Asp Leu Pro Gln Pro Val Asn Ala Gly Gly Ser Gly
225                 230                 235                 240
Gly Gly Ser Gly Gly Gly Ser Glu Gly Gly Ser Glu Gly Gly
                245                 250                 255
Ser Glu Gly Gly Gly Ser Glu Gly Gly Gly Ser Glu Gly Gly Ser Gly
            260                 265                 270
Ser Gly Asp Phe Asp Tyr Glu Lys Met Ala Asn Ala Asn Lys Gly Ala
        275                 280                 285
Met Thr Glu Asn Ala Asp Glu Asn Ala Leu Gln Ser Asp Ala Lys Gly
    290                 295                 300
Lys Leu Asp Ser Val Ala Thr Asp Tyr Gly Ala Ala Ile Asp Gly Phe
305                 310                 315                 320
Ile Gly Asp Val Ser Gly Leu Ala Asn Gly Asn Gly Ala Thr Gly Asp
                325                 330                 335
Phe Ala Gly Ser Asn Ser Gln Met Ala Gln Val Gly Asp Gly Asp Asn
            340                 345                 350
Ser Pro Leu Met Asn Asn Phe Arg Gln Tyr Leu Pro Ser Leu Pro Gln
        355                 360                 365
```

Ser Val Glu Cys Arg Pro Phe Val Gly Ala Gly Lys Pro Tyr Glu
370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
            405                 410                 415

Asn Ile Leu Arg Asn Lys Glu Ser
            420

<210> SEQ ID NO 10
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 10

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
                20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Cys
50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Gly Ser Glu
                85                  90                  95

Gly Gly Gly Ser Glu Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
            130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Ser Gly
225                 230                 235                 240

Gly Gly Ser Gly Gly Gly Ser Glu Gly Gly Gly Ser Glu Gly Gly Gly
                245                 250                 255

Ser Glu Gly Gly Gly Ser Glu Gly Gly Gly Ser Gly Gly Gly Ser Ser
            260                 265                 270

Gln Met Ala Gln Val Gly Asp Gly Asp Asn Ala Gln Val Gly Asp Gly
        275                 280                 285

Asp Asn Gln Tyr Leu Pro Ser Leu Pro Gln Ser Val Glu Cys Arg Pro
    290                 295                 300

```
Phe Val Phe Gly Ala Gly Lys Pro Tyr Glu Phe Ser Ile Asp Cys Asp
305                 310                 315                 320

Lys Ile Asn Leu Phe Arg Gly Val Phe Ala Phe Leu Leu Tyr Val Ala
                325                 330                 335

Thr Phe Met Tyr Val Phe Ser Thr Phe Ala Asn Ile Leu Arg Asn Lys
                340                 345                 350

Glu Ser

<210> SEQ ID NO 11
<211> LENGTH: 351
<212> TYPE: PRT
<213> ORGANISM: Artificial Sequence
<220> FEATURE:
<223> OTHER INFORMATION: Synthetic Polypeptide

<400> SEQUENCE: 11

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
                20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Val Cys
    50                  55                  60

Thr Gly Asp Glu Thr Gln Cys Trp Val Pro Ile Gly Leu Ala Ile Pro
65                  70                  75                  80

Glu Asn Glu Gly Gly Gly Ser Glu Gly Gly Gly Ser Glu Gly Gly Gly
                85                  90                  95

Ser Glu Gly Gly Gly Thr Lys Pro Pro Glu Tyr Gly Asp Thr Lys Pro
                100                 105                 110

Pro Glu Tyr Gly Asp Ile Asn Pro Leu Asp Gly Thr Tyr Pro Pro Gly
            115                 120                 125

Thr Glu Gln Asn Pro Ala Asn Pro Asn Pro Ser Leu Glu Glu Ser Gln
    130                 135                 140

Pro Leu Asn Thr Phe Met Phe Gln Asn Asn Arg Phe Arg Asn Arg Gln
145                 150                 155                 160

Gly Ala Leu Thr Val Tyr Thr Gly Thr Val Thr Gln Gly Thr Asp Pro
                165                 170                 175

Val Lys Thr Tyr Tyr Gln Tyr Thr Pro Val Ser Ser Lys Ala Met Tyr
                180                 185                 190

Asp Ala Tyr Trp Asn Gly Lys Phe Arg Asp Cys Ala Phe His Ser Gly
            195                 200                 205

Phe Asn Glu Asp Pro Phe Val Cys Glu Tyr Gln Gly Gln Ser Ser Asp
    210                 215                 220

Leu Pro Gln Pro Pro Val Asn Ala Gly Gly Gly Ser Gly Gly Gly Ser
225                 230                 235                 240

Gly Gly Gly Ser Glu Gly Gly Ser Glu Gly Gly Ser Glu
                245                 250                 255

Gly Gly Ser Glu Gly Gly Gly Ser Gly Gly Gly Ser Ser Gln Met Ala
                260                 265                 270

Gln Val Gly Asp Gly Asp Asn Ser Pro Leu Met Asn Asn Phe Arg Gln
            275                 280                 285

Tyr Leu Pro Ser Leu Pro Gln Ser Val Glu Cys Arg Pro Phe Val Phe
    290                 295                 300

Gly Ala Gly Lys Pro Tyr Glu Phe Ser Ile Asp Cys Asp Lys Ile Asn
```

```
                305                 310                 315                 320
Leu Phe Arg Gly Val Phe Ala Phe Leu Leu Tyr Val Ala Thr Phe Met
                    325                 330                 335
Tyr Val Phe Ser Thr Phe Ala Asn Ile Leu Arg Asn Lys Glu Ser
                340                 345                 350

<210> SEQ ID NO 12
<211> LENGTH: 280
<212> TYPE: PRT
<213> ORGANISM: Artificial Sequence
<220> FEATURE:
<223> OTHER INFORMATION: Synthetic Polypeptide

<400> SEQUENCE: 12

Met Lys Lys Leu Leu Phe Ala Ile Pro Leu Val Val Pro Phe Tyr Ser
1               5                   10                  15
His Ser Ala Glu Thr Val Gly Gly Ser Glu Gly Gly Thr Lys
            20                  25                  30
Pro Pro Glu Tyr Gly Asp Thr Pro Ile Pro Gly Tyr Thr Tyr Ile Asn
        35                  40                  45
Pro Leu Asp Gly Thr Tyr Pro Pro Gly Thr Glu Gln Asn Pro Ala Asn
    50                  55                  60
Pro Asn Pro Ser Leu Glu Glu Ser Gln Pro Leu Asn Thr Phe Met Phe
65                  70                  75                  80
Gln Asn Asn Arg Phe Arg Asn Arg Gln Gly Ala Leu Thr Val Tyr Thr
                85                  90                  95
Gly Thr Val Thr Gln Gly Thr Asp Pro Val Lys Thr Tyr Tyr Gln Tyr
            100                 105                 110
Thr Pro Val Ser Ser Lys Ala Met Tyr Asp Ala Tyr Trp Asn Gly Lys
        115                 120                 125
Phe Arg Asp Cys Ala Phe His Ser Gly Phe Asn Glu Asp Pro Phe Val
    130                 135                 140
Cys Glu Tyr Gln Gly Gln Ser Ser Asp Leu Pro Gln Pro Pro Val Asn
145                 150                 155                 160
Ala Gly Gly Gly Ser Gly Gly Gly Ser Gly Gly Gly Ser Glu Gly Gly
                165                 170                 175
Gly Ser Glu Gly Gly Ser Glu Gly Gly Ser Glu Gly Gly
            180                 185                 190
Ser Gly Gly Gly Ser Ser Gln Met Ala Gln Val Gly Asp Gly Asp Asn
        195                 200                 205
Ser Pro Leu Met Asn Asn Phe Arg Gln Tyr Leu Pro Ser Leu Pro Gln
    210                 215                 220
Ser Val Glu Cys Arg Pro Phe Val Phe Gly Ala Gly Lys Pro Tyr Glu
225                 230                 235                 240
Phe Ser Ile Asp Cys Asp Lys Ile Asn Leu Phe Arg Gly Val Phe Ala
                245                 250                 255
Phe Leu Leu Tyr Val Ala Thr Phe Met Tyr Val Phe Ser Thr Phe Ala
            260                 265                 270
Asn Ile Leu Arg Asn Lys Glu Ser
        275                 280

<210> SEQ ID NO 13
<211> LENGTH: 172
<212> TYPE: PRT
<213> ORGANISM: Artificial Sequence
<220> FEATURE:
<223> OTHER INFORMATION: Synthetic Polypeptide
```

<400> SEQUENCE: 13

Met Lys Lys Leu Leu Phe Ala Ile Pro Leu Val Val Pro Phe Tyr Ser
1               5                   10                  15

His Ser Ala Glu Thr Val Asp Phe Asp Tyr Glu Lys Met Ala Asn Ala
            20                  25                  30

Asn Lys Gly Ala Met Thr Glu Asn Ala Asp Glu Asn Ala Leu Gln Ser
        35                  40                  45

Asp Ala Lys Gly Lys Leu Asp Ser Val Ala Thr Asp Tyr Gly Ala Ala
    50                  55                  60

Ile Asp Gly Phe Ile Gly Asp Val Ser Gly Leu Ala Asn Gly Asn Gly
65                  70                  75                  80

Ala Thr Gly Asp Phe Ala Gly Ser Asn Ser Gln Met Ala Gln Val Gly
                85                  90                  95

Asp Gly Asp Asn Ser Pro Leu Met Asn Asn Phe Arg Gln Tyr Leu Pro
            100                 105                 110

Ser Leu Pro Gln Ser Val Glu Cys Arg Pro Phe Val Phe Gly Ala Gly
        115                 120                 125

Lys Pro Tyr Glu Phe Ser Ile Asp Cys Asp Lys Ile Asn Leu Phe Arg
    130                 135                 140

Gly Val Phe Ala Phe Leu Leu Tyr Val Ala Thr Phe Met Tyr Val Phe
145                 150                 155                 160

Ser Thr Phe Ala Asn Ile Leu Arg Asn Lys Glu Ser
                165                 170

<210> SEQ ID NO 14
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 14

Met Lys Lys Leu Leu Phe Ala Ile Pro Leu Val Val Pro Phe Tyr Ser
1               5                   10                  15

His Ser Ala Glu Thr Val Ser Gln Met Ala Gln Val Gly Asp Gly Asp
            20                  25                  30

Asn Ser Pro Leu Met Asn Asn Phe Arg Gln Tyr Leu Pro Ser Leu Pro
        35                  40                  45

Gln Ser Val Glu Cys Arg Pro Phe Val Phe Gly Ala Gly Lys Pro Tyr
    50                  55                  60

Glu Phe Ser Ile Asp Cys Asp Lys Ile Asn Leu Phe Arg Gly Val Phe
65                  70                  75                  80

Ala Phe Leu Leu Tyr Val Ala Thr Phe Met Tyr Val Phe Ser Thr Phe
                85                  90                  95

Ala Asn Ile Leu Arg Asn Lys Glu Ser
            100                 105

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
taatacgact cactataggg                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
aattaaccct cactaaaggg    20

<210> SEQ ID NO 17
<211> LENGTH: 166
<212> TYPE: DNA
<213> ORGANISM: Escherichia coli

<400> SEQUENCE: 17
gatgaaattc gccacttgtt agtgtaattc gctaactcat cctggcatgt tgctgttgat    60
tcttcaatca gatctttata aatcaaaaag ataaaaaatt ggcacgcaaa ttgtattaac    120
agttcagcag gacaatcctg aacgcagaaa tcaagaggac aacatt    166

<210> SEQ ID NO 18
<211> LENGTH: 27
<212> TYPE: DNA
<213> ORGANISM: Escherichia coli

<400> SEQUENCE: 18
gatgagctta cccgccatat ccgcatc    27

<210> SEQ ID NO 19
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 19
gatgagctta ccgtacatat ccgcatc    27

<210> SEQ ID NO 20
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 20
gatgagctta ccagacatat ccgcatc    27

<210> SEQ ID NO 21
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 21

Asp Glu Leu Thr Arg His Ile Arg Ile
1               5

<210> SEQ ID NO 22
<211> LENGTH: 9
<212> TYPE: PRT
<213> ORGANISM: Artificial Sequence
<220> FEATURE:

<223> OTHER INFORMATION: Synthetic Polypeptide

<400> SEQUENCE: 22

Asp Glu Leu Thr Val His Ile Arg Ile
1               5

<210> SEQ ID NO 23
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 23
gatgaaattc gccacttgtt agtgtaattc gctaactcat cctggcatgt tgctgttgat    60
tcttcaatca gatctttata aatcaaaaag ataaaaaatt ggcacgcaaa ctgtattaac   120
agttcagcag gacaatcctg aacgcagaaa tcaagaggac aacatt                  166

<210> SEQ ID NO 24
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 24
gatgaaattc gccacttgtt agtgtaattc gctaactcat cctggcatgt tgctgttgat    60
tcttcaatca gatctttata aatcaaaaag ataaaaaatt ggcacgcaaa ttctattaac   120
agttcagcag gacaatcctg aacgcagaaa tcaagaggac aacatt                  166

<210> SEQ ID NO 25
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 25
gatgaaattc gccacttgtt agtgtaattc gctaactcat cctggcatgt tgctgttgat    60
tcttcaatca gatctttata aatcaaaaag ataaaaaatt ggcacgcaaa ttttattaac   120
agttcagcag gacaatcctg aacgcagaaa tcaagaggac aacatt                  166

<210> SEQ ID NO 26
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 26
gatgaaattc gccacttgtt agtgtaattc gctaactcat cccggcacgt ggccgaagat    60
tcttcaatca gatctttata aatcaaaaag ataaaaaatt ggcacgcaaa ttgtattaac   120
agttcagcag gacaagcctg aacgcagaaa tcaagaggac aacagt                  166

<210> SEQ ID NO 27
<211> LENGTH: 166
<212> TYPE: DNA
<213> ORGANISM: Artificial Sequence
<220> FEATURE:
<223> OTHER INFORMATION: Synthetic Polynucleotide -continued

<400> SEQUENCE: 27

| gatgaaattc gccacttgtt agtgtaattc gctaactcat cccggcacgt ggccgaagat | 60 |
| tcttcaatca gatctttata aatcaaaaag ataaaaaatt ggcacgcaaa ttgtgttaac | 120 |
| agttcagcag acaagcctg aacgcagaaa tcaagaggac aacagt | 166 |

<210> SEQ ID NO 28
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 28

| gatgaaattc gccacttgtt agtgtaattc gctaactcat cccggcacgt ggccgaagat | 60 |
| tcttcaatca gatctttata aatcaaaaag ataaaaaatt ggcacgcaaa ctgtattaac | 120 |
| agttcagcag acaagcctg aacgcagaaa tcaagaggac aacagt | 166 |

<210> SEQ ID NO 29
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 29

| gatgaaattc gccacttgtt agtgtaattc gctaactcat cccggcacgt ggccgaagat | 60 |
| tcttcaatca gatctttata aatcaaaaag ataaaaaatt ggcacgcaaa ctgtgttaac | 120 |
| agttcagcag acaagcctg aacgcagaaa tcaagaggac aacagt | 166 |

<210> SEQ ID NO 30
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 30

| gatgaaattc gccacttgtt agtgtaattc gctaactcat cctggcatgt tgctgttgat | 60 |
| tcttcaatca gatctttata aatcaaaaag ataaaaaatt ggcacgcaaa ttgtgttaac | 120 |
| agttcagcag acaatcctg aacgcagaaa tcaagaggac aacatt | 166 |

<210> SEQ ID NO 31
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 31

| gatgaaattc gccacttgtt agtgtaattc gctaactcat cctggcatgt tgctgttgat | 60 |
| tcttcaatca gatctttata aatcaaaaag ataaaaaatt ggcacgcaaa ttgtcttaac | 120 |
| agttcagcag acaatcctg aacgcagaaa tcaagaggac aacatt | 166 |

<210> SEQ ID NO 32
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 32

```
gatgaaattc gccacttgtt agtgtaattc gctaactcat cctggcatgt tgctgttgat    60
tcttcaatca gatctttata aatcaaaaag ataaaaaatt ggcacgcaaa ttctgttaac   120
agttcagcag gacaatcctg aacgcagaaa tcaagaggac aacatt                  166
```

<210> SEQ ID NO 33
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 33

```
gatgaaattc gccacttgtt agtgtaattc gctaactcat cctggcatgt tgctgttgat    60
tcttcaatca gatctttata aatcaaaaag ataaaaaatt ggcacgcaaa ttctcttaac   120
agttcagcag gacaatcctg aacgcagaaa tcaagaggac aacatt                  166
```

<210> SEQ ID NO 34
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 34

```
gatgaaattc gccacttgtt agtgtaattc gctaactcat cctggcatgt tgctgttgat    60
tcttcaatca gatctttata aatcaaaaag ataaaaaatt ggcacgcaaa ctgtcttaac   120
agttcagcag gacaatcctg aacgcagaaa tcaagaggac aacatt                  166
```

<210> SEQ ID NO 35
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 35

```
gatgaaattc gccacttgtt agtgtaattc gctaactcat cctggcatgt tgctgttgat    60
tcttcaatca gatctttata aatcaaaaag ataaaaaatt ggcacgcaaa ctctattaac   120
agttcagcag gacaatcctg aacgcagaaa tcaagaggac aacatt                  166
```

<210> SEQ ID NO 36
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 36

```
gatgaaattc gccacttgtt agtgtaattc gctaactcat cctggcatgt tgctgttgat    60
tcttcaatca gatctttata aatcaaaaag ataaaaaatt ggcacgcaaa ctctgttaac   120
agttcagcag gacaatcctg aacgcagaaa tcaagaggac aacatt                  166
```

<210> SEQ ID NO 37
<211> LENGTH: 166
<212> TYPE: DNA
<213> ORGANISM: Artificial Sequence
<220> FEATURE:

<223> OTHER INFORMATION: Synthetic Polynucleotide

<400> SEQUENCE: 37
gatgaaattc gccacttgtt agtgtaattc gctaactcat cctggcatgt tgctgttgat    60
tcttcaatca gatctttata aatcaaaaag ataaaaaatt ggcacgcaaa ctctcttaac   120
agttcagcag gacaatcctg aacgcagaaa tcaagaggac aacatt                  166

<210> SEQ ID NO 38
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 38
gatgaaattc gccacttgtt agtgtaattc gctaactcat cctggcatgt tgctgttgat    60
tcttcaatca gatctttata aatcaaaaag ataaaaaatt ggcacgcaag ttgtattaac   120
agttcagcag gacaatcctg aacgcagaaa tcaagaggac aacatt                  166

<210> SEQ ID NO 39
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 39
gatgaaattc gccacttgtt agtgtaattc gctaactcat cctggcatgt tgctgttgat    60
tcttcaatca gatctttata aatcaaaaag ataaaaaatt ggcacgcaaa ttgcattaac   120
agttcagcag gacaatcctg aacgcagaaa tcaagaggac aacatt                  166

<210> SEQ ID NO 40
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 40
gatgaaattc gccacttgtt agtgtaattc gctaactcat cctggcatgt tgctgttgat    60
tcttcaatca gatctttata aatcaaaaag ataaaaaatt ggcacgcaag ttgcattaac   120
agttcagcag gacaatcctg aacgcagaaa tcaagaggac aacatt                  166

<210> SEQ ID NO 41
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 41
gatgaaattc gccacttgtt agtgtaattc gctaactcat cctggcatgt tgctgttgat    60
tcttcaatca gatctttata aatcaaaaag ataaaaaatt ggcacgcaaa gtgtattaac   120
agttcagcag gacaatcctg aacgcagaaa tcaagaggac aacatt                  166

<210> SEQ ID NO 42
<211> LENGTH: 166
<212> TYPE: DNA
<213> ORGANISM: Artificial Sequence

```
<220> FEATURE:
<223> OTHER INFORMATION: Synthetic Polynucleotide

<400> SEQUENCE: 42
gatgaaattc gccacttgtt agtgtaattc gctaactcat cctggcatgt tgctgttgat    60
tcttcaatca gatctttata aatcaaaaag ataaaaaatt ggcacgcaaa tggtattaac   120
agttcagcag gacaatcctg aacgcagaaa tcaagaggac aacatt                  166

<210> SEQ ID NO 43
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 43
gatgaaattc gccacttgtt agtgtaattc gctaactcat cctggcatgt tgctgttgat    60
tcttcaatca gatctttata aatcaaaaag ataaaaaatt ggcacgcaaa tcgtattaac   120
agttcagcag gacaatcctg aacgcagaaa tcaagaggac aacatt                  166

<210> SEQ ID NO 44
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 44
gatgaaattc gccacttgtt agtgtaattc gctaactcat cctggcatgt tgctgttgat    60
tcttcaatca gatctttata aatcaaaaag ataaaaaatt ggcacgcaaa tagtattaac   120
agttcagcag gacaatcctg aacgcagaaa tcaagaggac aacatt                  166
```